(12) United States Patent
Smith et al.

(10) Patent No.: US 8,524,869 B2
(45) Date of Patent: Sep. 3, 2013

(54) HUMANIZED ANTIBODIES AGAINST LIGHT AND USES THEREOF

(75) Inventors: Rodger Smith, Jefferson, MD (US); Palanisamy Kanakaraj, Germantown, MD (US); Bridget A. Cooksey, Gaithersburg, MD (US); Viktor Roschke, Bethesda, MD (US); Craig Rosen, Pasadena, MD (US)

(73) Assignee: Teva Biopharmaceuticals USA, Inc., Rockville, MD (US)

( * ) Notice: Subject to any disclaimer, the term of this patent is extended or adjusted under 35 U.S.C. 154(b) by 0 days.

(21) Appl. No.: 13/256,425

(22) PCT Filed: Mar. 22, 2010

(86) PCT No.: PCT/US2010/028144
§ 371 (c)(1),
(2), (4) Date: Dec. 22, 2011

(87) PCT Pub. No.: WO2010/111180
PCT Pub. Date: Sep. 30, 2010

(65) Prior Publication Data
US 2012/0100074 A1   Apr. 26, 2012

Related U.S. Application Data

(60) Provisional application No. 61/202,661, filed on Mar. 24, 2009.

(51) Int. Cl.
*C07K 16/00* (2006.01)
*A61K 39/395* (2006.01)
*C07H 21/04* (2006.01)

(52) U.S. Cl.
USPC ............... 530/387.1; 514/21.2; 536/23.53

(58) Field of Classification Search
None
See application file for complete search history.

(56) References Cited

U.S. PATENT DOCUMENTS

| | | | |
|---|---|---|---|
| 4,444,887 A | 4/1984 | Hoffmann | |
| 4,694,778 A | 9/1987 | Learn et al. | |
| 4,716,111 A | 12/1987 | Osband et al. | |
| 4,741,900 A | 5/1988 | Alvarez et al. | |
| 4,816,397 A | 3/1989 | Boss et al. | |
| 4,816,567 A | 3/1989 | Cabilly et al. | |
| 4,946,778 A | 8/1990 | Ladner et al. | |
| 4,980,286 A | 12/1990 | Morgan et al. | |
| 5,116,964 A | 5/1992 | Capon et al. | |
| 5,122,464 A | 6/1992 | Wilson et al. | |
| 5,225,538 A | 7/1993 | Capon et al. | |
| 5,225,539 A | 7/1993 | Winter | |
| 5,258,498 A | 11/1993 | Huston et al. | |
| 5,314,995 A | 5/1994 | Fell, Jr. et al. | |
| 5,413,923 A | 5/1995 | Kucherlapati et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,585,089 A | 12/1996 | Queen et al. | |
| 5,591,669 A | 1/1997 | Krimpenfort et al. | |
| 5,625,126 A | 4/1997 | Lonberg et al. | |
| 5,633,425 A | 5/1997 | Lonberg et al. | |
| 5,658,570 A | 8/1997 | Newman et al. | |
| 5,661,016 A | 8/1997 | Lonberg et al. | |
| 5,693,761 A | 12/1997 | Queen et al. | |
| 5,693,762 A | 12/1997 | Queen et al. | |
| 5,693,780 A | 12/1997 | Newman et al. | |
| 5,736,137 A | 4/1998 | Anderson et al. | |
| 5,756,096 A | 5/1998 | Newman et al. | |
| 5,807,715 A | 9/1998 | Morrison et al. | |
| 5,811,524 A | 9/1998 | Brams et al. | |
| 5,814,318 A | 9/1998 | Lonberg et al. | |
| 5,892,019 A | 4/1999 | Schlom et al. | |
| 5,939,598 A | 8/1999 | Kucherlapati et al. | |
| 6,075,181 A | 6/2000 | Kucherlapati et al. | |
| 6,150,584 A | 11/2000 | Kucherlapati et al. | |
| 6,180,370 B1 | 1/2001 | Queen et al. | |
| 6,190,370 B1 | 2/2001 | Tsui | |
| 6,193,980 B1 | 2/2001 | Efstathiou et al. | |
| 6,413,777 B1 | 7/2002 | Reff et al. | |
| 6,420,140 B1 | 7/2002 | Hori et al. | |
| 6,458,592 B1 | 10/2002 | Jakobovits et al. | |
| 6,632,927 B2 * | 10/2003 | Adair et al. ............... | 530/387.3 |
| 2002/0123057 A1 | 9/2002 | Zauderer et al. | |
| 2003/0157641 A1 | 8/2003 | Reff et al. | |
| 2003/0215442 A1 * | 11/2003 | Fraser et al. ............... | 424/131.1 |

FOREIGN PATENT DOCUMENTS

| | | |
|---|---|---|
| EP | 0 519 596 A1 | 12/1992 |
| EP | 0 396 387 B1 | 12/1993 |
| EP | 0 592 106 B1 | 11/2004 |
| WO | WO 86/05807 A1 | 10/1986 |
| WO | WO 89/01036 A1 | 2/1989 |

(Continued)

OTHER PUBLICATIONS

Rudikoff et al. 1982, Proc. Natl. Acad. Sci. USA, , 79: 1979-1983.*
Panka et al., 1988, Proc. Natl. Acad. Sci. USA, 85: 3080-3084.*
Sanofi Aventis Press Dept., "Anti Light fully Human Monoclonal Antibody," May 14, 2009, 2 pages.
Wang et al., Dysregulated Light expression on T cells mediates intestinal inflammation and contributes to IgA nephropathy, *The Journ. of Clin. Invest.*, pp. 826-835 (2004).
Yu et al., "Priming of naïve T cells inside tumor leads to eradication of established tumors," *Nature Immunology*, vol. 5, No. 2, pp. 141-149 (2004).
Morel et al., "Reciprocal Expression of the TNF Family Receptor Herpes Virus Entry Mediator and Its Ligand LIGHT on Activated T Cells: LIGHT Down-Regulates Its Own Receptor," *The Amer. Assoc. of Immunologies*, pp. 4397-4404 (2000).
Harrop et al., "Herpesvirus Entry Mediator Ligand (HVEM-L), a Novel Ligand for HVEM/TR2, Stimulates Proliferation of T Cells and Inhibits HT29 Cell Growth," *The Journ. of Biological Chemistry*, pp. 27548-27556 (1998).

(Continued)

*Primary Examiner* — Ilia Ouspenski
(74) *Attorney, Agent, or Firm* — Foley & Lardner LLP

(57) ABSTRACT

The present invention is directed to antigen-binding polypeptides, or variants or derivatives thereof which specifically bind the LIGHT polypeptide. The invention is also directed to methods of making and using such antibodies specifically in the treatment or diagnosis of immune, inflammatory and malignant diseases or conditions (e.g. inflammatory bowel disease; Crohn's disease, ulcerative colitis, multiple sclerosis, rheumatoid arthritis and transplantation).

19 Claims, 20 Drawing Sheets

(56) References Cited

FOREIGN PATENT DOCUMENTS

| WO | WO 89/12624 A2 | 12/1989 |
|----|----|----|
| WO | WO 91/09967 A1 | 7/1991 |
| WO | WO 91/10741 A1 | 7/1991 |
| WO | WO 91/14438 A1 | 10/1991 |
| WO | WO 92/08495 A1 | 5/1992 |
| WO | WO 96/33735 A1 | 10/1996 |
| WO | WO 96/34096 A1 | 10/1996 |
| WO | WO 98/16654 A1 | 4/1998 |
| WO | WO 98/24893 A2 | 6/1998 |
| WO | WO 98/46645 A2 | 10/1998 |
| WO | WO 98/50433 A2 | 11/1998 |
| WO | WO 98/52976 A1 | 11/1998 |
| WO | WO 00/34317 A2 | 6/2000 |
| WO | WO 03/089575 A2 | 10/2003 |
| WO | WO 2008/027338 A2 | 3/2008 |

OTHER PUBLICATIONS

Mauri et al., "LIGHT, a New Member of the TNF Superfamily and Lymphotoxin α Are Ligands for Herpesvirus Entry Mediator," *Immunity*, vol. 8, pp. 21-30 (1998).

International Search Report cited in related International Patent Application No. PCT/US2010/028144, completed Jun. 29, 2010.

Written Opinion cited in related International Patent Application No. PCT/US2010/028144, completed Jun. 29, 2010.

Arnon et al., "Monoclonal Antibodies For immunotargeting Of Drugs In Cancer Therapy", *Monoclonal Antibodies And Cancer Therapy*, pp. 243-256 (1985).

Ashkenazi et al., "Protection against endotoxic shock by a tumor necrosis factor receptor immunoadhesin," *Proc. Natl. Acad. Sci.*, vol. 88, pp. 10535-10539 (1991).

Ausubel, F. M. et al., eds., "Current Protocols in Molecular Biology," vol. I, *Green Publishing Associates, Inc. and John Wiley & Sons, Inc., New York* at pp. 6.3.1-6.3.6 and 2.10.3), (1989).

Baldwin et al., "Analysis, Results, And Future Prospective Of The Therapeutic Use Of Radiolabeled Antibody In Cancer Therapy", in *Monoclonal Antibodies For Cancer Detection And Therapy*, pp. 303-316 (Academic Press) (1985).

Bebbington et al., "High-level Expression of a Recombinant Antibody from Myeloma Cells using a Glutamine Synthetase Gene as an Amplifiable Selectable Marker," *Bio/Techniques*, vol. 10, pp. 169-175 (1992).

Buchwald et al., "Long-term, continuous intravenous heparin administration by an implantable infusion pump in ambulatory patients with recurrent venous thrombosis," *Surgery*, vol. 88, pp. 507-516 (1980).

Chothia et al., "Canonical Structures for the Hypervariable Regions of Immunoglobulins," *J. Mol. Biol.*, vol. 196, pp. 901-917 (1987).

Cockett et al., "High-Level Expression of Tissue Inhibotor of Metalloproteinases in Chinese Hamster Ovary Cells Using Glutamine Synthetase Gene Amplification," *Bio/Technology*, vol. 8, pp. 662-667 (1990).

Colberre-Garapin et al., A new Dominant Hybrid Selective Marker for Higher Eukaryotic Cells, *J. Mol. Biol.*, No. 150, pp. 1-14 (1981).

Creighton, "Proteins: Structures and Molecular Principles," W.H. Freeman & Co., NY, pp. 28-60 (1983).

During et al., "Controlled Release of Dopamine from a Polymeric Brain Implant: In Vivo Characterization," *Ann. Neurol.*, pp. 351-356 (1989).

Foecking et al., "Powerful and versatile enhancer-promoter unit for mammalian expression vectors," *Gene*, No. 45, pp. 101-105 (1986).

Gentz et al., "Bioassay for trans-activation using purified human immunodeficiency virus tat-encoded protein: Trans-activation requires mRNA synthesis," *Proc. Natl. Acad. Sci.*, No. 86, pp. 821-824 (1989).

Gillies et al., "High-level expression of chimeric antibodies using adapted cDNA variable region cassettes," *J. Immunol. Methods*, No. 125, pp. 191-202 (1989).

Goodson, "Medical Applications of Controlled Release," supra, vol. 2, pp. 115-138 (1984).

Howard et al., "Intracerebral drug delivery in rats with lesion-induced memory deficits," *J. Neurosurg.* No. 71, pp. 105-112 (1989).

Inouye et al., "Up-promoter mutations in the lpp gene of *Escherichia coli*,", *Nucleic Acids Res.*, No. 13, pp. 3101-3109 (1985).

Joliot et al., "Antennapedia homeobox peptide regulates neural morphogenesis," *Proc. Natl. Acad. Sci.* USA, vol. 88, pp. 1864-1868 (1991).

Kohler, "Immunoglobulin chain loss in hybridoma lines," *Proc. Natl. Acad. Sci.*, vol. 77, No. 4, pp. 2197-2199 (1980).

Levy et al., "Inhibition of Calcification of Bioprosthetic Heart Valves by Local Controlled-Release Diphosphonate," *Science*, vol. 228, pp. 190-192 (1985).

Lopez-Berestein, "Treatment of Systemic Fungal Infections with Liposomal-Amphotericin B," pp. 317-327 (1989).

Lowy et al., "Isolation of Transforming DNA: Cloning the Hamster aprt Gene," *Cell*, No. 22, pp. 817-823 (1980).

Proudfoot, "Transcriptional interference and termination between duplicated a-globin gene constructs suggests a novel mechanism for gene regulation," *Nature* 322, pp. 562-565 (1986).

Rattan et al., Protein Synthesis, Posttranslational Modifications, and Aging, *Ann. N.Y., Acad Sci.*, 663, pp. 48-62 (1992).

Riechmann et al., "Reshaping human antibodies for therapy," *Nature* 352, pp. 323-327 (1988).

Roguska et al., "Humanization of murine monoclonal antibodies through variable domain resurfacing," *PNAS* 91, pp. 969-973 (1994).

Santerre et al., "Expression of prokaryotic genes for hygromycin B and G418 resistance as dominant-selection markers in mouse L cells," *Gene* 30, pp. 147-156 (1984).

Saudek et al., "A preliminary trial of the programmable implantable medication system for insulin delivery," N. Engl. J. Med. 321, pp. 574-580 (1989).

Sefton, "Implantable Pumps," *CRC Crit. Ref. Biomed. Eng.*, No. 14, pp. 201-240 (1987).

Seifter et al., "Analysis for Protein Modifications and Nonprotein Cofactors," *Meth Enzymol* 182, pp. 626-646 (1990).

Studnicka et al., "Human-engineered monoclonal antibodies retain full specific binding activity by preserving non-CDR complementarity-modulating residues," *Protein Engineering* 7(6), pp. 805-814 (1994).

Szybalska et al., "Genetics of Human Cell Lins, IV. DNA-Mediated Heritable Transformation of a Biochemical Trait," *Proc. Natl. Acad. Sci.*, USA 48, pp. 2026-2034 (1992).

Thorpe et al., "The Preparation And Cytotoxic Properties Of Antibody-Toxin Conjugates", *Immunol. Rev.* 62, pp. 119-158 (1982).

Traunecker et al. "Bispecific single chain molecules (Janusins) target cytotoxic lymphocytes on HIV infected cells" *EMBO J.*, 10, pp. 3655-3659 (1991).

Traunecker et al. "Janusin: new molecular design for bispecific reagents," *Int J Cancer Suppl* 7, pp. 51-52 (1992).

Traunecker et al., "Soluble CD4 molecules neutralize human immunodeficiency virus type 1," *Nature* 331, pp. 84-86 (1988).

Treat et al., "Liposome encapsulated doxorubicin preliminary results of Phase I and Phase II Trials," in Liposomes in the Therapy of Infectious Disease and Cancer, Lopez-Berestein and Fidler (eds.), Liss, N.Y., pp. 353-365 (1989).

Van Heeke et al., "Expression of Human Asparagine Synthetase in *Escherichia coli*," *J. Biol. Chem.* 24, pp. 5503-5509 (1989).

Wigler et al., "Transfer of Purified Herpes Virus Thymidine Kinase Gene to Cultured Mouse Cells," *Cell* 11, pp. 223-232 (1977).

Wilson et al., "The Structure of an Antigentic Determinant in a Protein," *Cell* 37, pp. 767-778 (1984).

Wu et al., "Delivery systems for gene therapy," *Biotherapy* 3, pp. 87-95 (1991).

Wu and Wu, "Receptor-mediated in Vitro Gene Transformation by a Soluble DNA Carrier System," *J. Biol. Chem.*, 262, pp. 4429-4432 (1987).

* cited by examiner

Inhibition LIGHT binding to plate-bound receptors by LIGHT antibody 10D11

Inhibition of LIGHT-induced HT-29 cell killing by
LIGHT antibody compared to LTβR-Fc Inhibition of human LIGHT induced HT-29 cell killing
by purified LIGHT antibodies Inhibition of cynomolgus LIGHT-induced HT-29 cell killing by purified LIGHT antibodies

Figure 6A

Hum 10D11 VH #1, a fully humanized LIGHT antibody VH domain

```
              10              20              30
 1  Q V Q L V Q S G A E V K K P G A S V K V S C K A S G Y T F T   Hum 10D11VH#1
 1  E I Q L Q Q S G P D L V K P G A S V K V S C K A S G Y S F T   Mu 10D11 VH
 1  Q V Q L V Q S G A E V K K P G A S V K V S C K A S G Y T F T   VH1-02

40              50              60
31  D Y Y I Y W V R Q A P G Q G L E W I G Y I D P Y N G G T K Y   Hum 10D11VH#1
31  D Y Y I Y W V R Q S H G K S L E W I G Y I D P Y N G G T K Y   Mu 10D11 VH
31  G Y Y M H W V R Q A P G Q G L E W M G W I N P N S G G T N Y   VH1-02

70              80              90
61  N Q K F K D R V T M T R D T S I S T A Y M E L S R L R S D D   Hum 10D11VH#1
61  N Q K F K D T A S L T V D K S S S T A F M H L N S L T S E D   Mu 10D11 VH
61  A Q K F Q G R V T M T R D T S I S T A Y M E L S R L R S D D   VH1-02

100             110
91  T A V Y Y C A R T S G S S W F P Y W G Q G T L V T V S S       Hum 10D11VH#1
91  S A V Y Y C A R T S G S S W F P Y W G Q G T L V T V S A       Mu 10D11 VH
91  T A V Y Y C A R                                               VH1-02
```

Figure 6B

Hum 10D11 VH #2, a partially humanized LIGHT antibody VH domain

```
            10                  20                  30
 1  Q V Q L V Q S G A E V K K P G A S V K V S C K A S G Y T F T   Hum 10D11VH#2
 1  E I Q L Q Q S G P D L V K P G A S V K V S C K A S G Y S F T   Mu 10D11 VH
 1  Q V Q L V Q S G A E V K K P G A S V K V S C K A S G Y A F T   CAI54212

40                  50                  60
31  D Y Y I Y W V R Q A P G Q G L E W I G Y I D P Y N G G T K Y   Hum 10D11VH#2
31  D Y Y I Y W V R Q S H G K S L E W I G Y I D P Y N G G T K Y   Mu 10D11 VH
31  S Y N M Y W V R Q A P G Q G L E W I G Y I D P Y N G D T F Y   CAI54212

70                  80                  90
61  N Q K F K D K A T L T V D K S T S T A Y M E L S S L R S E D   Hum 10D11VH#2
61  N Q K F K D T A S L T V D K S S S T A F M H L N S L T S E D   Mu 10D11 VH
61  N Q K F K G K A T L T V D K S T S T A Y M E L S S L R S E D   CAI54212

100                 110
91  T A V Y Y C A R T S G S S H F P Y W G Q G T L V T V S S       Hum 10D11VH#2
91  S A V Y Y C A R T S G S S H F P Y W G Q G T L V T V S A       Mu 10D11 VH
91  T A V Y Y C A R Q N Y G S - F A Y W G Q G T L V T V S S       CAI54212
```

Figure 6C

Hum 10D11 VK #1, a fully humanized LIGHT antibody VK domain

```
          10                  20                  30
 1  E I V L T Q S P D F Q S V T P K E K V T I T C R A S Q S I S    Hum 10D11VK#1
 1  D I V L T Q S P A T L S V T P G D S V S L S C R A S Q S I S   Mu 10D11 VK
 1  E I V L T Q S P D F Q S V T P K E K V T I T C R A S Q S I G    A26 VK 40                  50                  60
31  N N L H W Y Q Q K P D Q S P K L L I K Y T Y Q S I S G V P S    Hum 10D11VK#1
31  N N L H W Y Q Q K S H E S P R L L I K Y T Y Q S I S G I P S   Mu 10D11 VK
31  S S L H W Y Q Q K P D Q S P K L L I K Y A S Q S F S G V P S    A26 VK 70                  80                  90
61  R F S G S G S G T D F T L T I N S L E A E D A A T Y Y C Q Q    Hum 10D11VK#1
61  R F S G S G S G T D F T L T I N S V E T E D F G M Y F C Q Q   Mu 10D11 VK
61  R F S G S G S G T D F T L T I N S L E A E D A A T Y Y C H Q    A26 VK 100
91  S N R H P L T F G Q G T K V E I K R                            Hum 10D11VK#1
91  S N R H P L T F G A G T K L E L K R                           Mu 10D11 VK
91  S S S L P                                                     A26 VK
```

Inhibition of LIGHT-induced HT-29 cell killing
by humanized LIGHT antibody

**Inhibition of LIGHT-induced HT-29 killing
by humanized LIGHT antibodies**

Inhibition of cynomolgus LIGHT-induced HT-29
killing by humanized LIGHT antibody Binding of LIGHT antibodies to
PMA/Ionomycin activated Th17 cells

**Binding of humanized LIGHT antibody
to activated T cells**

Figure 11A

Alignment of VH domains from 4 lead candidate
mouse anti-LIGHT mAbs

Alignment of VK domains from 4 lead candidate mouse
anti-LIGHT mAbs

Alignment of mouse anti-LIGHT 5E10 VH to 3 closest human germline VH domains

Alignment of mouse anti-LIGHT 5E10 VK to 3 closest
human germline VK domains

```
              10                  20                  30
 1  A I R M T Q S P S S F S A S T G D R V T I T C R A S Q G I S      VK L9
 1  D I Q L T Q S P S F L S A S V G D R V T I T C R A S Q G I S      VK L8
 1  D I Q M T Q S P S S L S A S V G D R V T I T C R A S Q G I S      VK A20
 1  D I V M T Q S H K F M S T S V G D R V S I T C K A S Q D V G      5E10 VK AA 40                  50                  60
31  S Y L A W Y Q Q K P G K A P K L L I Y A A S T L Q S G V P S      VK L9
31  S Y L A W Y Q Q K P G K A P K L L I Y A A S T L Q S G V P S      VK L8
31  N Y L A W Y Q Q K P G K V P K L L I Y A A S T L Q S G V P S      VK A20
31  T A V A W Y Q Q K P G Q S P K L L I Y W A S T R H T G V P D      5E10 VK AA 70                  80                  90
61  R F S G S G S G T D F T L T I S C L Q S E D F A T Y Y C Q Q      VK L9
61  R F S G S G S G T E F T L T I S S L Q P E D F A T Y Y C Q Q      VK L8
61  R F S G S G S G T D F T L T I S S L Q P E D F A T Y Y C Q H      VK A20
61  R F T G S G S G P D F T L T I S N V Q S E D L A D Y F C Q Q C    5E10 VK AA 100
91  Y Y S Y P                                                        VK L9
91  L N S Y P                                                        VK L8
91  Y N S A P                                                        VK A20
91  Y S S Y P L T F G S G T K L E I K R                              5E10 VK AA
```

HUMANIZED ANTIBODIES AGAINST LIGHT AND USES THEREOF

The present application claims the benefit of U.S. Provisional Application No. 61/202,661 filed on Mar. 24, 2009. The contents of U.S. Provisional Application No. 61/202,661 is hereby incorporated by reference in their entirety.

BACKGROUND OF THE INVENTION

The present invention is directed to antigen-binding polypeptides which specifically bind the LIGHT polypeptide, and methods of making and using such antibodies. Specifically the invention is directed to humanized antigen-binding polypeptides which specifically bind the LIGHT polypeptide. The antigen-binding polypeptides are useful in treating and diagnosing immune, inflammatory and malignant diseases and conditions such as inflammatory bowel disease, Crohn's disease, ulcerative colitis, multiple sclerosis, rheumatoid arthritis and transplantation.

Proteins that are structurally related to tumor necrosis factor (TNF) are collectively referred to as the TNF super family. LIGHT, a TNF super family member, is expressed on activated T-cells and immature dendritic cells (Tamada et al., *J. Immunology*. 2000). LIGHT is a type II transmembrane protein and has been designated as TNF superfamily member 14 (TNFSF14) and is also called TL5, LTg, CD258 and HVEML. LIGHT is a T costimulatory molecule and induces T-cell proliferation and cytokine production (Tamada K. et al., *Nat. Med.* 2000). LIGHT also induces an inflammatory response in monocytes and endothelial cells (Otterdal et al., *Blood* 2006; Chang et al., *J. Biomed. Sci.* 2005).

LIGHT binds to 3 distinct receptors expressed on different cell types: herpes virus entry mediator (HVEM) expressed on T-cells and B cells (Kwon et al., *J. Biol. Chem* 1997)), lymphotoxin β receptor (LTβR) expressed on stromal cells and non-hematopoietic cells (Ettinger et al., *Curr Top Microbiol Immunol.* 2000) and decoy receptor 3/TR6. LIGHT on both dendridic cells and T-cells augments T-cell proliferation and cytokine production. rLIGHT can directly costimulate T-cell responses (Tamada K. et al., *Nat. Med.* 2000).

The role of LIGHT in various inflammatory and disease conditions has been demonstrated by various models using LIGHT deficient models and LIGHT overexpressing transgenic animals. Over expression of LIGHT in mice results in a hyper activated peripheral T-cell population and spontaneous development of severe autoimmune disease. (Wang et al., *Clin. Invest.* 2001). Targeted disruption of LIGHT causes a defect in co-stimulatory activation of T-cells and Th1 type immune response. (Scheu et al., *J. Exp. Med.* 2002; Xu et al. *J Immunol.* 2007).

Because of its potent stimulatory activity on T-cells, LIGHT is an important component of chronic inflammation. Thus, antibodies to LIGHT, in particular LIGHT antagonist antibodies, would be useful in treating diseases associated with chronic inflammation. Such disease include, but are not limited to those discussed below.

Dysregulated immune response to gut flora is the main cause of inflammatory bowel disease (IBD). T helper cells play an essential role in the aberrant immune repose in IBD. In particular, Th1 cells have been linked to Crohn's disease. The critical role of LIGHT in intestinal inflammation has been demonstrated by several studies. LIGHT over-expressing transgenic mice are susceptible to T-cell mediated autoimmune diseases and LIGHT transgenic mice exhibit severe T-cell mediated intestinal inflammation and develop colitis (Wang J. et al., *J. Clin. Invest.* 2004; Wang J. et al., *J. Immunol* 2005; Wang et al., *J. Clin. Invest* 2001; Shaikh et al., *J. Immunol.* 2001). Additionally, blocking the interaction of LIGHT to its receptor by soluble LTβR-Fc ameliorates TNBS-induced colitis (An, M M et al., *Pharmacol. Res.* 2005). LIGHT maps to the region overlapping a susceptibility locus for IBD on human chromosome 19p13.312-14 (Rioux et al., *Am. Hum. Genet.* (2000); Bonen et al., *Gastroenterology* (2003)).

High levels of LIGHT protein have been detected in the synovial fluid of patients with rheumatoid arthritis (RA). See for example, Recombinant LIGHT-induced inflammatory mediators in synovial fibroblasts from RA patients (Pierer et al., *Rheumatology* (2007); Kang et al., *Arthritis & Rheumatism* (2007)) and Blocking LIGHT-receptor interaction prevents development of Collagen-Induced Arthritis (Fava et al., *J. Immunol.* (2003)). Finally, in November 2007, Biogen IDEC announced the use of baminercept (LTβR-Fc fusion protein) in Phase IIa clinical trials for RA patients (Biogen IDEC Press Release dated Nov. 9, 2007).

LIGHT is upregulated in experimental models of hepatitis. Blocking interaction of LIGHT with LIGHT receptors, by treatment with antibody or soluble LTβR, significantly attenuated hepatic inflammation and reduced the production of inflammatory cytokines and protected mice from lethal hepatitis (Anand et al., *J. Clin. Invest.* (2006); An et al. *Biol. Pharm. Bull.* (2006)).

Several studies have demonstrated that blockade of LIGHT-receptor interaction prevents graft-versus-host disease (GVHD) and prolongs allograft survival in animal models (Xu et al., *Blood* (2007); Ye et al., *J. Exp. Med.* (2002); Fan et al., *Transplantation* (2007)).

In addition to the studies mentioned above, blocking of LIGHT receptors (LTβR and HVEM) dramatically reduce signs of disease in different animal models such as Collagen-Induced Arthritis (CIA) and Experimental Autoimmune Encephalomyelitis (EAE), which is an animal model for multiple sclerosis (MS) (Fava et al., *J Immunol.* (2003) and Suen et al., *J. Exp. Med.* (1997)). LIGHT knockout mice are also deficient in production of IL-12 and, as a result, lack the ability to develop IFNγ mediated, antigen specific Th1 responses to inflammatory stimuli.

Thus, there is a need in the art to create antigen-binding polypeptides and antagonist antigen-binding polypeptides which specifically bind to LIGHT to treat inflammatory, malignant and autoimmune diseases and conditions such as multiple-sclerosis, IBD and RA as well as other disease described above or known in the art. Antigen-binding polypeptides and antagonist antigen-binding polypeptides which specifically bind LIGHT have a number of advantages compared to the use of a soluble receptor such as: 1) antibodies have a longer half-life in the bloodstream compared to Fc-fusion proteins; 2) antibodies have higher efficacy as the antibody can be designed to have a higher affinity for LIGHT compared to soluble receptors; and 3) antibodies are a safer alternative to soluble receptors because of the specificity to LIGHT. LIGHT antagonist antibodies would only block LIGHT mediated signaling, thus ameliorating the local inflammatory process without systemic depletion of the secondary lymphoid tissue architecture caused by soluble receptors which can eventually lead to immunosuppresion.

SUMMARY OF THE INVENTION

The present invention is based on the role of the LIGHT polypeptide in inflammatory diseases. Specifically, the invention is based on the ability of LIGHT to stimulate proinflammatory cytokines such as IFN-γ and IL-8 as well as being a potent stimulator of IL-17 production by CD3 costimulated Th17 cells. The link between LIGHT and the production of IL-17 is particularly important, as it has been recently discovered that Th17 cells are the critical driver of the inflammatory process causing sustained inflammation and tissue damage in all major autoimmune conditions such as multiple-sclerosis (MS), inflammatory bowel disease (IBD) and rheumatoid arthritis (RA).

The invention relates generally to antigen-binding polypeptides which bind specifically to the TNF-like cytokine TL5, also known as LIGHT (see GenBank accession no. AF036581, incorporated herein by reference in its entirety). In certain embodiments the antigen-binding polypeptides of the present invention include a humanized heavy chain variable region (VH) and a humanized light chain variable region (VK). For example, in certain embodiments the antigen-binding polypeptides of the present invention include the framework (FR) regions of the light and heavy chain variable regions of a human antibody, while retaining substantially the antigen-binding specificity of a parental monoclonal antibody (i.e. the complementary-determining regions (CDRs)). The humanized heavy chain variable region and/or the humanized light chain variable region are at least about 87% humanized, at least about 90% humanized, at least about 95% humanized, at least about 98% humanized, or at least about 100% humanized, excluding the CDRs. The antigen-binding polypeptides molecules are derived from monoclonal antibody donors (e.g., mouse monoclonal antibody donors) and include CDRs from the monoclonal antibodies (e.g., mouse monoclonal CDRs). In certain embodiments, the antigen-binding polypeptides of the present invention are antagonists of LIGHT activity and/or LIGHT interaction with LIGHT receptors.

Certain embodiments of the invention include an antigen-binding polypeptide which specifically binds to the LIGHT polypeptide comprising a humanized antibody heavy chain variable region comprising: (1) a CDR-H1 comprising an amino acid sequence of $X_1Y\ X_2X_3X_4$ (SEQ ID NO:18); wherein $X_1$ is the amino acid D, S, T or N; $X_2$ is the amino acid Y, L or W; $X_3$ is the amino acid I or M; and $X_4$ is the amino acid Y, H, E or N; (2) a CDR-H2 comprising an amino acid sequence of $X_5IX_6PX_7X_8X_9X_{10}X_{11}X_{12}X_{13}NX_{14}X_{15}FX_{16}X_{17}$ (SEQ ID NO:19); wherein $X_5$ is the amino acid Y, M, V or W; $X_6$ is the amino acid D, N, H or F; $X_7$ is the amino acid Y, G or S; $X_8$ is the amino acid N, S, T or D; $X_9$ is the amino acid G, S or D; $X_{10}$ is the amino acid G, D, E or I; $X_{11}$ is the amino acid T or S; $X_{12}$ is the amino acid K or R; and $X_{13}$ is the amino acid Y or L; $X_{14}$ is the amino acid Q or E; $X_{15}$ is the amino acid K or N; $X_{16}$ is the amino acid K, I or R; and $X_{17}$ is the amino acid G, A or D; and (3) a CDR-H3 comprising an amino acid sequence selected from the group consisting of: (i) $WX_{18}X_{19}$ (SEQ ID NO:20); (ii) $X_{20}X_{21}X_{22}X_{23}X_{24}X_{25}X_{26}X_{27}X_{28}$ (SEQ ID NO:21); and (iii) $X_{20}X_{21}X_{22}X_{23}X_{24}X_{25}X_{26}X_{27}X_{28}$AMDF (SEQ ID NO:22); wherein $X_{18}$ is the amino acid D or N; $X_{19}$ is the amino acid R or Y; $X_{20}$ is the amino acid E, T or G; $X_{21}$ is the amino acid D, S or N; $X_{22}$ is the amino acid Y or G; $X_{23}$ is the amino acid G, S or V; $X_{24}$ is the amino acid I, S or W; $X_{25}$ is the amino acid S, W or A; $X_{26}$ is the amino acid T, F or M; $X_{27}$ is the amino acid Y, P or D; and $X_{28}$ is the amino acid S or Y.

Certain embodiments of the invention include an antigen-binding polypeptide which specifically binds to the LIGHT polypeptide comprising a humanized antibody light chain variable region comprising: (1) a CDR-L1 comprising an amino acid sequence selected from the group consisting of: (i) $X_{29}X_{30}SX_{31}X_{32}X_{33}X_{34}X_{35}X_{36}X_{37}X_{38}$ (SEQ ID NO:38); (ii) $X_{29}X_{30}SX_{31}X_{32}X_{33}X_{34}X_{35}X_{36}X_{37}X_{38}X_{39}X_{40}X_{41}X_{42}$ (SEQ ID NO:39); and (iii) $X_{29}X_{30}SX_{31}X_{32}X_{33}X_{34}X_{35}X_{36}X_{37}X_{38}X_{39}X_{40}X_{41}X_{42}H$ (SEQ ID NO:40); wherein $X_{29}$ is the amino acid K or R; $X_{30}$ is the amino acid A or S; $X_{31}$ is the amino acid Q or K; $X_{32}$ is the amino acid D, S or N; $X_{33}$ is the amino acid V, I or L; $X_{34}$ is the amino acid G, S, V or L; $X_{35}$ is the amino acid T, N or H; $X_{36}$ is the amino acid A, N or S; $X_{37}$ is the amino acid V, L, N or G; $X_{38}$ is the amino acid A, H, G or Y; $X_{39}$ is the amino acid N or T; $X_{40}$ is the amino acid T or Y; $X_{41}$ is the amino acid Y or M; $X_{42}$ is the amino acid F or H; (2) a CDR-L2 comprising an amino acid sequence of $X_{43}X_{44}X_{45}X_{46}X_{47}X_{48}X_{49}$ (SEQ ID NO:41); wherein $X_{43}$ is the amino acid W, Y, K or I; $X_{44}$ is the amino acid A, T or V; $X_{45}$ is the amino acid S or Y; $X_{46}$ is the amino acid T, Q or N; $X_{47}$ is the amino acid R, S or L; $X_{48}$ is the amino acid H, I, F or E; and $X_{49}$ is the amino acid T or S; and (3) a CDR-L3 comprising an amino acid sequence of $X_{50}X_{51}X_{52}X_{53}X_{54}X_{55}PX_{56}T$ (SEQ ID NO:42); wherein $X_{50}$ is the amino acid Q or S; $X_{51}$ is the amino acid Q or H; $X_{52}$ is the amino acid S or Y; $X_{53}$ is the amino acid S, N, T or R; $X_{54}$ is the amino acid S, R, H or E; $X_{55}$ is the amino acid Y, W, V or L; and $X_{56}$ is the amino acid L or Y.

Certain embodiments of the invention include an antigen-binding polypeptide which specifically binds to the LIGHT polypeptide comprising a humanized antibody heavy chain variable region comprising: (1) a CDR-H1 comprising an amino acid sequence of $X_1Y\ X_2X_3X_4$ (SEQ ID NO:18); wherein $X_1$ is the amino acid D, S, T or N; $X_2$ is the amino acid Y, L or W; $X_3$ is the amino acid I or M; and $X_4$ is the amino acid Y, H, E or N; (2) a CDR-H2 comprising an amino acid sequence of $X_5IX_6PX_7X_8X_9X_{10}X_{11}X_{12}X_{13}NX_{14}X_{15}FX_{16}X_{17}$ (SEQ ID NO:19); wherein $X_5$ is the amino acid Y, M, V or W; $X_6$ is the amino acid D, N, H or F; $X_7$ is the amino acid Y, G or S; $X_8$ is the amino acid N, S, T or D; $X_9$ is the amino acid G, S or D; $X_{10}$ is the amino acid G, D, E or I; $X_{11}$ is the amino acid T or S; $X_{12}$ is the amino acid K or R; and $X_{13}$ is the amino acid Y or L; $X_{14}$ is the amino acid Q or E; $X_{15}$ is the amino acid K or N; $X_{16}$ is the amino acid K, I or R; and $X_{17}$ is the amino acid G, A or D; and (3) a CDR-H3 comprising an amino acid sequence selected from the group consisting of: (i) $WX_{18}X_{19}$ (SEQ ID NO:20); (ii) $X_{20}X_{21}X_{22}X_{23}X_{24}X_{25}X_{26}X_{27}X_{28}$ (SEQ ID NO:21); and (iii) $X_{20}X_{21}X_{22}X_{23}X_{24}X_{25}X_{26}X_{27}X_{28}$AMDF (SEQ ID NO:22); wherein $X_{18}$ is the amino acid D or N; $X_{19}$ is the amino acid R or Y; $X_{20}$ is the amino acid E, T or G; $X_{21}$ is the amino acid D, S or N; $X_{22}$ is the amino acid Y or G; $X_{23}$ is the amino acid G, S or V; $X_{24}$ is the amino acid I, S or W; $X_{25}$ is the amino acid S, W or A; $X_{26}$ is the amino acid T, F or M; $X_{27}$ is the amino acid Y, P or D; and $X_{28}$ is the amino acid S or Y; and a humanized antibody light chain variable region comprising: (1) a CDR-L1 comprising an amino acid sequence selected from the group consisting of: (i) $X_{29}X_{30}SX_{31}X_{32}X_{33}X_{34}X_{35}X_{36}X_{37}X_{38}$ (SEQ ID NO:38); (ii) $X_{29}X_{30}SX_{31}X_{32}X_{33}X_{34}X_{35}X_{36}X_{37}X_{38}X_{39}X_{40}X_{41}X_{42}$ (SEQ ID NO:39); and (iii) $X_{29}X_{30}SX_{31}X_{32}X_{33}X_{34}X_{35}X_{36}X_{37}X_{38}X_{39}X_{40}X_{41}X_{42}H$ (SEQ ID NO:40); wherein $X_{29}$ is the amino acid K or R; $X_{30}$ is the amino acid A or S; $X_{31}$ is the amino acid Q or K; $X_{32}$ is the amino acid D, S or N; $X_{33}$ is the amino acid V, I or L; $X_{34}$ is the amino acid G, S, V or L; $X_{35}$ is the amino acid T, N or H; $X_{36}$ is the amino acid A, N or S; $X_{37}$ is the amino acid V, L, N or G; $X_{38}$ is the amino acid A, H, G or Y; $X_{39}$ is the amino acid N or T; $X_{40}$ is the amino acid T or Y; $X_{41}$ is the amino acid Y or M; $X_{42}$ is the amino acid F or H; (2) a CDR-L2 comprising an amino acid sequence of $X_{43}X_{44}X_{45}X_{46}X_{47}X_{48}X_{49}$ (SEQ ID NO:41); wherein $X_{43}$ is the amino acid W, Y, K or I;

$X_{44}$ is the amino acid A, T or V; $X_{45}$ is the amino acid S or Y; $X_{46}$ is the amino acid T, Q or N; $X_{47}$ is the amino acid R, S or L; $X_{48}$ is the amino acid H, I, F or E; and $X_{49}$ is the amino acid T or S; and (3) a CDR-L3 comprising an amino acid sequence of $X_{50}X_{51}X_{52}X_{53}X_{54}X_{55}PX_{56}T$ (SEQ ID NO:42); wherein $X_{50}$ is the amino acid Q or S; $X_{51}$ is the amino acid Q or H; $X_{52}$ is the amino acid S or Y; $X_{53}$ is the amino acid S, N, T or R; $X_{54}$ is the amino acid S, R, H or E; $X_{55}$ is the amino acid Y, W, V or L; and $X_{56}$ is the amino acid L or Y.

Certain embodiments of the present invention include an antigen-binding polypeptide, which specifically binds to the LIGHT polypeptide, comprising a humanized antibody heavy chain variable region comprising: (1) a CDR-H1 comprising an amino acid sequence selected from the group consisting of: (i) SSYIH (SEQ ID NO:23); (ii) DYYIY (SEQ ID NO:26); (iii) TYLIE (SEQ ID NO:29); (iv) TYWMN (SEQ ID NO:32); and (v) NYLIE (SEQ ID NO:35); (2) a CDR-H2 comprising an amino acid sequence selected from the group consisting of: (i) WIFPGSDITKYNEKFKG (SEQ ID NO:24); (ii) YIDPYNGGTKYNQKFKD (SEQ ID NO:27); (iii) VINPGTGETKYNENFRA (SEQ ID NO:30); (iv) MIHPSDSESRLNQKFID (SEQ ID NO:33); and (v) VINPGSGDTKYNENFKG (SEQ ID NO:36); and (3) a CDR-H3 comprising an amino acid sequence selected from the group consisting of: (i) EDYGISTYSAMDF (SEQ ID NO:25); (ii) TSGSSWFPY (SEQ ID NO:28); (iii) WDR (SEQ ID NO:31); (iv) GNYVWAMDY (SEQ ID NO:34); and (v) WNY (SEQ ID NO:37).

Certain embodiments of the present invention include an antigen-binding polypeptide, which specifically binds to the LIGHT polypeptide, comprising a humanized antibody light chain variable region comprising: (1) a CDR-L1 comprising an amino acid sequence selected from the group consisting of: (i) KASQDVGTAVA (SEQ ID NO:43); (ii) RASQSISNNLH (SEQ ID NO:46); (iii) RSSQNLVHSNGNTYFH (SEQ ID NO:49); (iv) RASKSVSTSGYTYMH (SEQ ID NO:52); and (v) RSSQSLLHSNGNTYFH (SEQ ID NO:55); (2) a CDR-L2 comprising an amino acid sequence selected from the group consisting of: (i) WASTRHT (SEQ ID NO:44); (ii) YTYQSIS (SEQ ID NO:47); (iii) KVSNRFS (SEQ ID NO:50); and (iv) ITSNLES (SEQ ID NO:53); and (3) a CDR-L3 comprising an amino acid sequence selected from the group consisting of: (i) QQYSSYPLT (SEQ ID NO:45); (ii) QQSNRWPLT (SEQ ID NO:48); (iii) SQSTHVPYT (SEQ ID NO:51); and (iv) QHSRELPYT (SEQ ID NO:54).

Additional embodiments of the present invention include an antigen-binding polypeptide, which specifically binds to the LIGHT polypeptide, comprising a humanized antibody heavy chain variable region comprising (1) a CDR-H1 comprising the amino acid sequence SYYIH (SEQ ID NO:23); (2) a CDR-H2 comprising the amino acid sequence WIFPGSDITKYNEKFKG (SEQ ID NO:24); and (3) a CDR-H3 comprising the amino acid sequence EDYGISTYSAMDF (SEQ ID NO:25); and/or a humanized antibody light chain variable region comprising (1) a CDR-L1 comprising the amino acid sequence KASQDVGTAVA (SEQ ID NO:43); (2) a CDR-L2 comprising the amino acid sequence WASTRHT (SEQ ID NO:44); and (3) a CDR-L3 comprising the amino acid sequence QQYSSYPLT (SEQ ID NO:45).

Embodiments of the present invention also include an antigen-binding polypeptide, which specifically binds to the LIGHT polypeptide, comprising a humanized antibody heavy chain variable region comprising the amino acid sequence selected from the group consisting of:
(1) QVQLVQSGAEVKKPGASVKVSCKASGYTFTX$_1$-YX$_2$X$_3$X$_4$WVRQAPGQX'$_1$LEWX'$_2$G X$_5$IX$_6$PX$_7$X$_8$X$_9$X$_{10}$X$_{11}$X$_{12}$X$_{13}$NX$_{14}$X$_{15}$FX$_{16}$X$_{17}$X'$_3$X'$_4$-TX'$_5$TX'$_6$DX'$_7$SX'$_8$STX'$_9$YMELSX'$_{10}$LRSX'$_{11}$DTAVYYCARWX$_{18}$X$_{19}$WGQGTLVTVSS (SEQ ID NO:1);
(2) QVQLVQSGAEVKKPGASV KVSCKASGYTFTX$_1$YX$_2$X$_3$X$_4$WVRQAPGQX'$_1$LEWX'$_2$GX$_5$IX$_6$PX$_7$X$_8$X$_9$X$_{10}$X$_{11}$X$_{12}$X$_{13}$NX$_{14}$X$_{15}$F X$_{16}$X$_{17}$X'$_3$X'$_4$TX'$_5$TX'$_6$DX'$_7$SX'$_8$STX'$_9$YMELSX'$_{10}$LR-SX'$_{11}$DTAVYYCARX$_{20}$X$_{21}$X$_{22}$X$_{23}$X$_{24}$X$_{25}$X$_{26}$X$_{27}$X$_{28}$-WGQGTLVTVSS (SEQ ID NO:2); and (3) QVQLVQS-GAEVKKPGASVK VSCKASGYTFTX$_1$YX$_2$X$_3$X$_4$W-VRQAPGQX'$_1$LEWX'$_2$GX$_5$IX$_6$PX$_7$X$_8$X$_9$X$_{10}$X$_{11}$X$_{12}$X$_{13}$-NX$_{14}$X$_{15}$FX$_{16}$X$_{17}$X'$_3$X'$_4$TX'$_5$TX'$_6$DX'$_7$SX'$_8$STX'$_9$YMEL-SX'$_{10}$LRSX'$_{11}$DTAVYYCARX$_{20}$X$_{21}$X$_{22}$X$_{23}$X$_{24}$X$_{25}$X$_{26}$-X$_{27}$X$_{28}$AMDFWGQGTLVTVSS (SEQ ID NO:3), wherein X$_1$ is the amino acid D, S, T or N; X$_2$ is the amino acid Y, L or W; X$_3$ is the amino acid I or M; X$_4$ is the amino acid Y, H, E or N; X$_5$ is the amino acid Y, M, V or W; X$_6$ is the amino acid D, N, H or F; X$_7$ is the amino acid Y, G or S; X$_8$ is the amino acid N, S, T or D; X$_9$ is the amino acid G, S or D; X$_{10}$ is the amino acid G, D, E or I; X$_{11}$ is the amino acid T or S; X$_{12}$ is the amino acid K or R; and X$_{13}$ is the amino acid Y or L; X$_{14}$ is the amino acid Q or E; X$_{15}$ is the amino acid K or N; X$_{16}$ is the amino acid K, I or R; and X$_{17}$ is the amino acid G, A or D; wherein X$_{18}$ is the amino acid D or N; X$_{19}$ is the amino acid R or Y; X$_{20}$ is the amino acid E, T or G; X$_{21}$ is the amino acid D, S or N; X$_{22}$ is the amino acid Y or G; X$_{23}$ is the amino acid G, S or V; X$_{24}$ is the amino acid I, S or W; X$_{25}$ is the amino acid S, W or A; X$_{26}$ is the amino acid T, F or M; X$_{27}$ is the amino acid Y, P or D; X$_{28}$ is the amino acid S or Y; and wherein X'$_1$ is the amino acid R or G; X'$_2$ is the amino acid M or I; X'$_3$ is the amino acid K or R; X'$_4$ is the amino acid V or A; X'$_5$ is the amino acid M, L or I; X'$_6$ is the amino acid V or R; X'$_7$ is the amino acid T or K; X'$_8$ is the amino acid A, I or T; X'$_9$ is the amino acid V or A; X'$_{10}$ is the amino acid R or S; and X'$_{11}$ is the amino acid D or E.

Certain embodiments of the present invention include an antigen-binding polypeptide, which specifically binds to the LIGHT polypeptide, comprising a humanized antibody heavy chain variable region comprising the amino acid sequence selected from the group consisting of:

```
                                              (SEQ ID NO: 4)
QVQLVQSGAEVKKPGASVKVSCKASGYTFTSYYIHWVRQAPGQRLEWMG

WIFPGSDITKYNEKFKGRVTITRDTSASTAYMELSSLRSEDTAVYYCAR

EDYGISTYSAMDFWGQGTLVTVSS;

(SEQ ID NO: 5)
QVQLVQSGAEVKKPGASVKVSCKASGYTFTDYYIYWVRQAPGQGLEWIG

YIDPYNGGTKYNQKFKDRVTMTRDTSISTAYMELSRLRSDDTAVYYCAR

TSGSSWFPYWGQGTLVTVSS;

(SEQ ID NO: 6)
QVQLVQSGAEVKKPGASVKVSCKASGYTFTDYYIYWVRQAPGQGLEWIG

YIDPYNGGTKYNQKFKDKATLTVDKSTSTAYMELSSLRSEDTAVYYCAR

TSGSSWFPYWGQGTLVTVSS;

(SEQ ID NO: 7)
QVQLVQSGAEVKKPGASVKVSCKASGYTFTTYLIEWVRQAPGQGLEWMG

VINPGTGETKYNENFRARVTMTRDTSISTAYMELSRLRSDDTAVYYCAR

WDRWGQGTLVTVSS;
and
```

-continued (SEQ ID NO: 8)
QVQLVQSGAEVKKPGASVKVSCKASGYTFTTYWMNWVRQAPGQGLEWMG

MIHPSDSESRLNQKFIDRVTMTRDTSTSTVYMELSSLRSEDTAVYYCAR

GNYVWAMDYWGQGTLVTVSS.

Certain embodiments of the present invention include an antigen-binding polypeptide, which specifically binds to the LIGHT polypeptide, comprising a humanized antibody light chain variable region comprising the amino acid sequence selected from the group consisting of: (1) $X'_{12}X'_{13}X'_{14}X'_{15}TQX'_{16}PX'_{17}X'_{18}X'_{19}X'_{20}X'_{21}X'_{22}X'_{23}$-$X'_{24}X'_{25}X'_{26}X'_{27}X'_{28}X'_{29}X'_{30}CX_{29}X_{30}SX_{31}X_{32}X_{33}X_{34}$-$X_{35}X_{36}X_{37}X_{38}WX'_{31}X'_{32}QX'_{33}PX'_{34}X'_{35}X'_{36}PX'_{37}X'_{38}$-$LIX'_{39}X_{43}X_{44}X_{45}X_{46}X_{47}X_{48}X_{49}GX'_{40}PX'_{41}RFSGSGS$-$GTX'_{42}FTLX'_{43}IX'_{44}X'_{45}X'_{46}X'_{47}X'_{48}EDX'_{49}X'_{50}X'_{51}YY$-$CX_{50}X_{51}X_{52}X_{53}X_{54}X_{55}PX_{56}TFGQGTX'_{52}VEIKR$ (SEQ ID NO:9); (2) $X'_{12}X'_{13}X'_{14}X'_{15}TQX'_{16}PX'_{17}$-$X'_{18}X'_{19}X'_{20}X'_{21}X'_{22}X'_{23}X'_{24}X'_{25}X'_{26}X'_{27}X'_{28}X'_{29}X'_{30}C$-$X_{29}X_{30}SX_{31}X_{32}X_{33}X_{34}X_{35}X_{36}X_{37}X_{38}X_{39}X_{40}X_{41}X_{42}$-$WX'_{31}X'_{32}Q$ $X'_{33}PX'_{34}X'_{35}X'_{36}X'_{37}X'_{38}LIX'_{39}X_{43}$-$X_{44}X_{45}X_{46}X_{47}X_{48}X_{49}GX'_{40}PX'_{41}RFSGSGSGTX'_{42}FT$-$LX'_{43}IX'_{44}X'_{45}X'_{46}X'_{47}X'_{48}ED$ $X'_{49}X'_{50}X'_{51}YYCX_{50}X_{51}X_{52}X_{53}X_{54}X_{55}PX_{56}TFGQ$-$GTX'_{52}VEIKR$ (SEQ ID NO:10); and (3) $X'_{12}X'_{13}X'_{14}X'_{15}TQX'_{16}PX'_{17}X'_{18}X'_{19}X'_{20}X'_{21}X'_{22}X_{23}$-$X'_{24}X'_{25}X'_{26}X'_{27}X'_{28}X'_{29}X'_{30}CX_{29}X_{30}SX_{31}X_{32}X_{33}X_{34}$-$X_{35}X_{36}X_{37}X_{38}X_{39}X_{40}X_{41}X_{42}HWX'_{31}X'_{32}QX'_{33}PX_{34}$-$X'_{35}X'_{36}X'_{37}X'_{38}LIX'_{39}X_{43}X_{44}X_{45}X_{46}X_{47}X_{48}X_{49}GX_{40}P$-$X'_{41}RFSGSGSGTX'_{42}FTLX'_{43}IX'_{44}X'_{45}X'_{46}X'_{47}X'_{48}E$-$DX'_{49}X'_{50}X'_{51}YYCX_{50}X_{51}X_{52}X_{53}X_{54}X_{55}PX_{56}TFGQGT$-$X'_{52}VEIKR$ (SEQ ID NO:11), wherein $X_{29}$ is the amino acid K or R; $X_{30}$ is the amino acid A or S; $X_{31}$ is the amino acid Q or K; $X_{32}$ is the amino acid D, S or N; $X_{33}$ is the amino acid V, I or L; $X_{34}$ is the amino acid G, S, V or L; $X_{35}$ is the amino acid T, N or H; $X_{36}$ is the amino acid A, N or S; $X_{37}$ is the amino acid V, L, N or G; $X_{38}$ is the amino acid A, H, G or Y; $X_{39}$ is the amino acid N or T; $X_{40}$ is the amino acid T or Y; $X_{41}$ is the amino acid Y or M; $X_{42}$ is the amino acid F or H; $X_{43}$ is the amino acid W, Y, K or I; $X_{44}$ is the amino acid A, T or V; $X_{45}$ is the amino acid S or Y; $X_{46}$ is the amino acid T, Q or N; $X_{47}$ is the amino acid R, S or L; $X_{48}$ is the amino acid H, I, F or E; $X_{49}$ is the amino acid T or S; $X_{50}$ is the amino acid Q or S; $X_{51}$ is the amino acid Q or H; $X_{52}$ is the amino acid S or Y; $X_{53}$ is the amino acid S, N, T or R; $X_{54}$ is the amino acid S, R, H or E; $X_{55}$ is the amino acid Y, W, V or L; $X_{56}$ is the amino acid L or Y; and wherein $X'_{12}$ is amino acid D or E; $X'_{13}$ is amino acid I or V; $X'_{14}$ is amino acid V or Q; $X'_{15}$ is amino acid M or L; $X'_{16}$ is amino acid S or T; $X'_{17}$ is amino acid S, D, A or L; $X'_{18}$ is amino acid 5, T or F; $X'_{19}$ is amino acid L or Q; $X'_{20}$ is amino acid A, S or P; $X'_{21}$ is amino acid V or A; $X'_{22}$ is amino acid S or T; $X'_{23}$ is amino acid P, L or V; $X'_{24}$ is amino acid G or K; $X'_{25}$ is amino acid E, Q or D; $X'_{26}$ is amino acid R, K or P; $X'_{27}$ is amino acid A or V; $X'_{28}$ is amino acid T or S; $X'_{29}$ is amino acid I or L; $X'_{30}$ is amino acid S, T or N; $X'_{31}$ is amino acid F or Y; $X'_{32}$ is amino acid Q or L; $X'_{33}$ is amino acid K or R; $X'_{34}$ is amino acid G or D; $X'_{35}$ is amino acid Q or K; $X'_{36}$ is amino acid A, S or P; $X'_{37}$ is amino acid K, R or Q; $X'_{38}$ is amino acid L or R; $X'_{39}$ is amino acid Y or K; $X'_{40}$ is amino acid V or I; $X'_{41}$ is amino acid S, A or D; $X'_{42}$ is amino acid D or E; $X'_{43}$ is amino acid K or T; $X'_{44}$ is amino acid S or N; $X'_{45}$ is amino acid S or R; $X'_{46}$ is amino acid V or L; $X'_{47}$ is amino acid Q or E; $X'_{48}$ is amino acid P, A or S; $X'_{49}$ is amino acid F, A or V; $X'_{50}$ is amino acid A or G; $X'_{51}$ is amino acid T or V; and $X'_{52}$ is amino acid R or K.

Certain embodiments of the present invention also include an antigen-binding polypeptide, which specifically binds to the LIGHT polypeptide, comprising a humanized antibody light chain variable region comprising the amino acid sequence selected from the group consisting of:

(SEQ ID NO: 12)
DIQLTQSPSFLSASVGDRVTITCKASQDVGTAVAWYQQKPGKAPKLLIYW

ASTRHTGVPSRFSGSGSGTEFTLTISSLQPEDFATYYCQQYSSYPLTFGQ

GTKVEIKR;

(SEQ ID NO: 13)
EIVLTQSPDFQSVTPKEKVTITCRASQSISNNLHWYQQKPDQSPKLLIKY

TYQSISGVPSRFSGSGSGTDFTLTINSLEAEDAATYYCQQSNRWPLTFGQ

GTKVEIKR;

(SEQ ID NO: 14)
EIVMTQSPATLSVSPGEKATLSCRASQSISNNLHWYQQKPGQAPRLLIYY

TYQSISGIPARFSGSGSGTEFTLTISSLQSEDFAVYYCQQSNRWPLTFGQ

GTRVEIKR;

(SEQ ID NO: 15)
DVVMTQSPLSLPVTLGQPASISCRSSQNLVHSNGNTYFHWFQQRPGQSPR

RLIYKVSNRFSGVPDRFSGSGSGTDFTLKISRVEAEDVGVYYCSQSTHVP

YTFGQGTKVEIKR;

(SEQ ID NO: 16)
DIVMTQTPLSLSVTPGQPASISCRSSQNLVHSNGNTYFHWYLQKPGQSPQ

LLIYKVSNRFSGVPDRFSGSGSGTDFTLKISRVEAEDVGVYYCSQSTHVP

YTFGQGTKVEIKR;
and (SEQ ID NO: 17)
DIVMTQSPDSLAVSLGERATINCRASKSVSTSGYTYMHWYQQKPGQPPKL

LIYITSNLESGVPDRFSGSGSGTDFTLTISSLQAEDVAVYYCQHSRELPY

TFGQGTKVEIKR.

Certain embodiments of the present invention include an antigen-binding polypeptide which specifically binds to the LIGHT polypeptide comprising: (a) a variable heavy chain region comprising the amino acid sequence: QVQLVQSGAEVKKPGASVKVSCKASGYTFTS YYIHWVRQAPGQRLEWMGWIFPGSDITKYNEKFKGRVTITRDTSASTAYMELSSLRSEDTA VYYCAREDYGISTYSAMDFWGQGTLVTVSS (SEQ ID NO:4) and (b) a variable light chain region comprising the amino acid sequence: DIQLTQSPSFLSASVGDRVTITC-KAS QDVGTAVAWYQQKPGKAPKLLIYWAST-RHTGVPSRFSGSGSGTEFTLTISSLQP EDFATYYC-QQYSSYPLTFGQGTKVEIKR (SEQ ID NO:12).

In certain embodiments of the present invention, antigen-binding polypeptides, that specifically bind to the LIGHT polypeptide, comprise either one of the aforementioned humanized heavy chains or humanized light chains or combinations thereof. Additionally, in certain embodiments the antigen-binding polypeptides of the present invention comprise one or more of the aforementioned CDR regions from the heavy chain (i.e. CDR-H1, CDR-H2 or CDR-H3) or one more of the aforementioned CDR regions from the light chain (i.e. CDR-L1, CDR-L2 or CDR-L3) or combinations thereof.

In other embodiments of the present invention, the antigen-binding polypeptide that specifically binds to the LIGHT polypeptide is an antibody molecule, or fragment thereof such as a Fab fragment, a Fab' fragment, a F(ab')2 fragment or an scFv molecule.

In certain embodiments, the antigen-binding polypeptide is an antibody molecule. Antibody molecules may include chimeric antibodies that include, for example, a human heavy chain constant region and a human light chain constant region fused to a murine heavy chain variable region and a murine light chain variable region. In other embodiments, the antigen-binding polypeptide is an scFv molecule which comprises a polypeptide with the formula selected from the group consisting of NH$_2$-L-VH-X-VK-COOH and NH$_2$-L-VK-X-VH-COOH; wherein L is a leader sequence; VH is the humanized antibody heavy chain variable region; X is a linking polypeptide; and VK is the humanized antibody light chain variable region. In additional embodiments, the scFv molecule is fused or linked to human serum albumin polypeptide (HSA) to create a scFV HSA fusion molecule. The scFv molecule may be fused or linked to the N- or C-terminus of HSA. In other embodiments, the antigen-binding polypeptide is a Fab fragment. The Fab fragment of the present invention may be fused or linked to HSA. The heavy chain or light chain of the Fab fragment may be fused or linked to the N- or C-terminus of HSA.

Certain embodiments of the present invention include the antigen-binding polypeptide conjugated or fused to a therapeutic or diagnostic agent. For example, therapeutic agents may be selected from the group consisting of a cytotoxic agent, a radioactive label, an immunomodulator, a hormone, an enzyme, an oligonucleotide, a photoactive therapeutic agent and a combination thereof. Examples of diagnostic agents may include a radioactive label, a photoactive diagnostic agent, an ultrasound-enhancing agent or a non-radioactive label.

Certain embodiments of the present invention also include compositions comprising the antigen-binding polypeptides of the invention and methods of making such polypeptides. Additionally, embodiments of the present invention include methods of treating or diagnosing an inflammatory, immune or malignant disease or condition comprising administering the antigen-binding polypeptides and compositions of the invention to a patient in need thereof. In other embodiments, the invention includes methods for treating diseases using the compositions of the present invention including, but not limited to, autoimmune disease (e.g., lupus), inflammatory bowel disease (IBD), chronic obstructive pulmonary disease (COPD), arthritis (e.g., rheumatoid arthritis), multiple sclerosis, Graft versus host disease (GVHD), transplant rejection, central nervous system injury, Th1-mediated intestinal diseases such as Crohn's disease, psoriasis, leukemia or lymphoma (e.g., chronic lymphocytic leukemia (CLL)), atherosclerosis, lung and colon carcinomas and viral infections such as hepatitis.

In certain embodiments, the present invention includes isolated polynucleotides encoding the aforementioned antigen-binding polypeptides. The polynucleotides may be operably linked to a promoter for expressing the encoded polypeptides in a suitable host cell. Additionally, embodiments of the present invention include methods for producing the antigen-binding polypeptides of the present invention comprising: a) culturing a cell transformed with a polynucleotide encoding the antigen-binding polypeptide of the present invention in order to express the encoded polypeptide; and b) recovering the polypeptide so expressed.

BRIEF DESCRIPTION OF THE DRAWINGS

FIG. 5A shows the ability of the murine anti-LIGHT monoclonal antibody, 10D11, to inhibit LIGHT induced HT-29 cell apoptosis. FIGS. 5B and C show the ability of murine antibodies 5E10, 13C7, 14A10, 14G8, 15G4, 7G5, 18F1, 2B12, 16F12, 18B1 and 10D11AB to inhibit human (B) and cynomolgus (C) LIGHT induced HT-29 cell apoptosis.

FIG. 6A illustrates an alignment of the VH Domain of mouse anti-LIGHT 10D11 with the closest human germline, VH1-02. The alignment was used as a template to create a humanized 10D11 VH, identified in FIG. 6A as Hum 10D11 VH#1.

FIG. 6B illustrates an alignment of the VH Domain of mouse anti-LIGHT 10D11 with an expressed antibody VH domain, identified as CAI54212 and which is derived in part from the VH1-02 germline from FIG. 6A. The alignment was used as a template to create a humanized 10D11 VH, identified in FIG. 6B as Hum 10D11 VH#2.

FIG. 6C illustrates an alignment of the VK domain of mouse anti-LIGHT 10D11 with the closest human germline gene, A26. The alignment was used as a template to create a humanized 10D11 VK, identified in FIG. 6C as Hum 10D11 VK#1.

FIG. 10A illustrates mouse LIGHT antibodies binding to activated Th17 cells. LIGHT antibodies were incubated with Th17 cells for 40 minutes at room temperature. Mouse IgG1 is used as negative control.

Figure 11A:
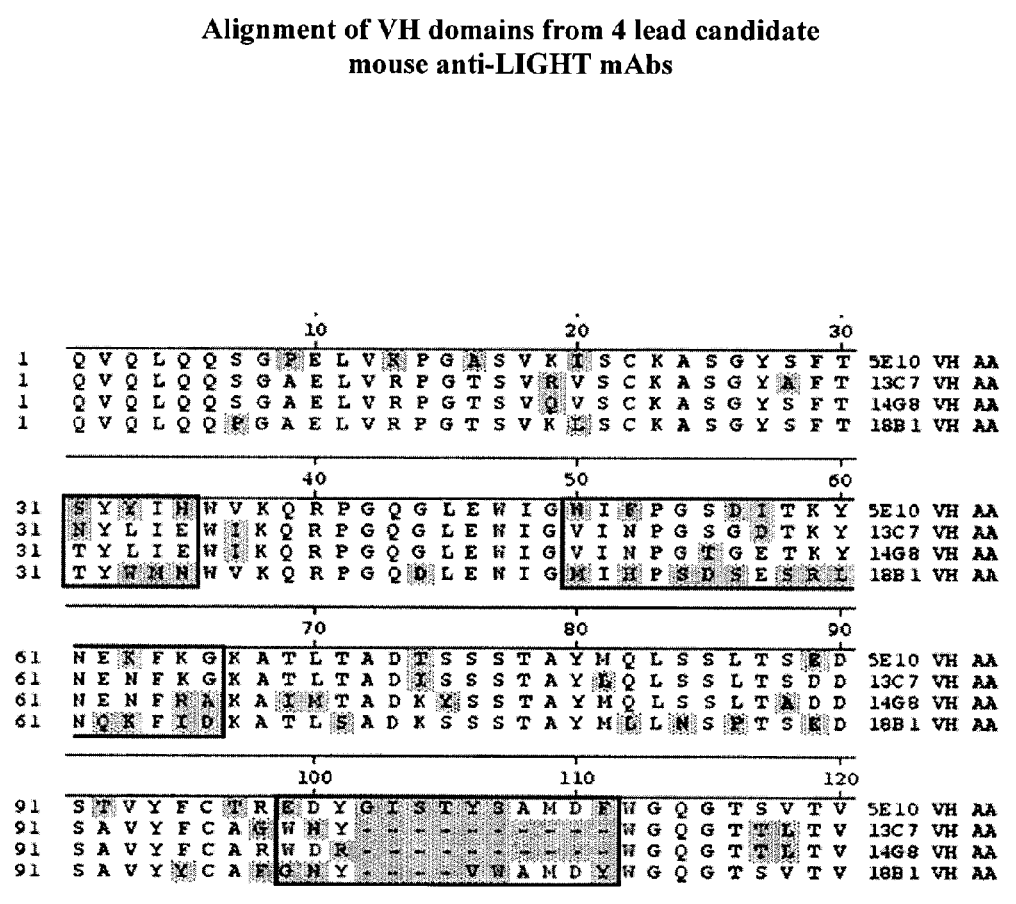
Figure 11B:
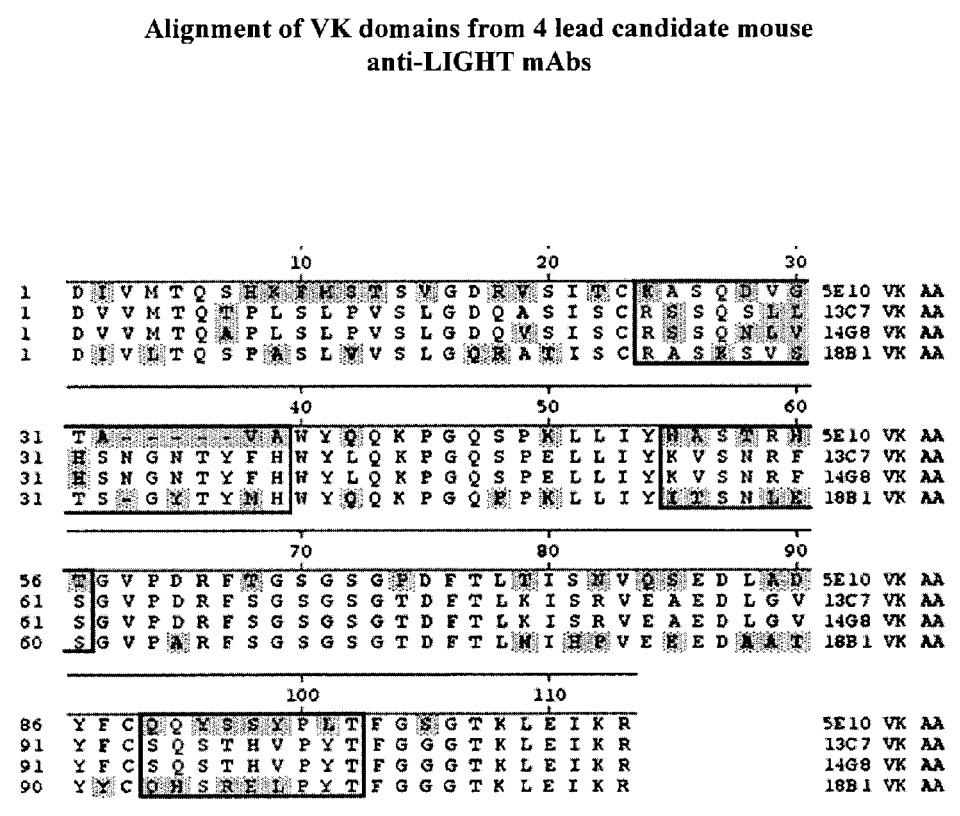

FIGS. 11A and B show sequence alignments of the variable heavy chain domain (A) and the variable light chain domain (B) from candidate murine anti-LIGHT antibodies (5E10, 13C7, 14G8 and 18B1). The boxes in the figure denote the CDR domains in each sequence.

FIGS. 11C and D show sequence alignments of the murine 5E10 variable heavy chain VH (C) and variable light chain VK (D) to three closest matching human germline variable heavy chain domain (VH) and variable light chain domain (VK) sequences.

DETAILED DESCRIPTION OF THE PREFERRED EMBODIMENTS

Definitions

Figure 1:
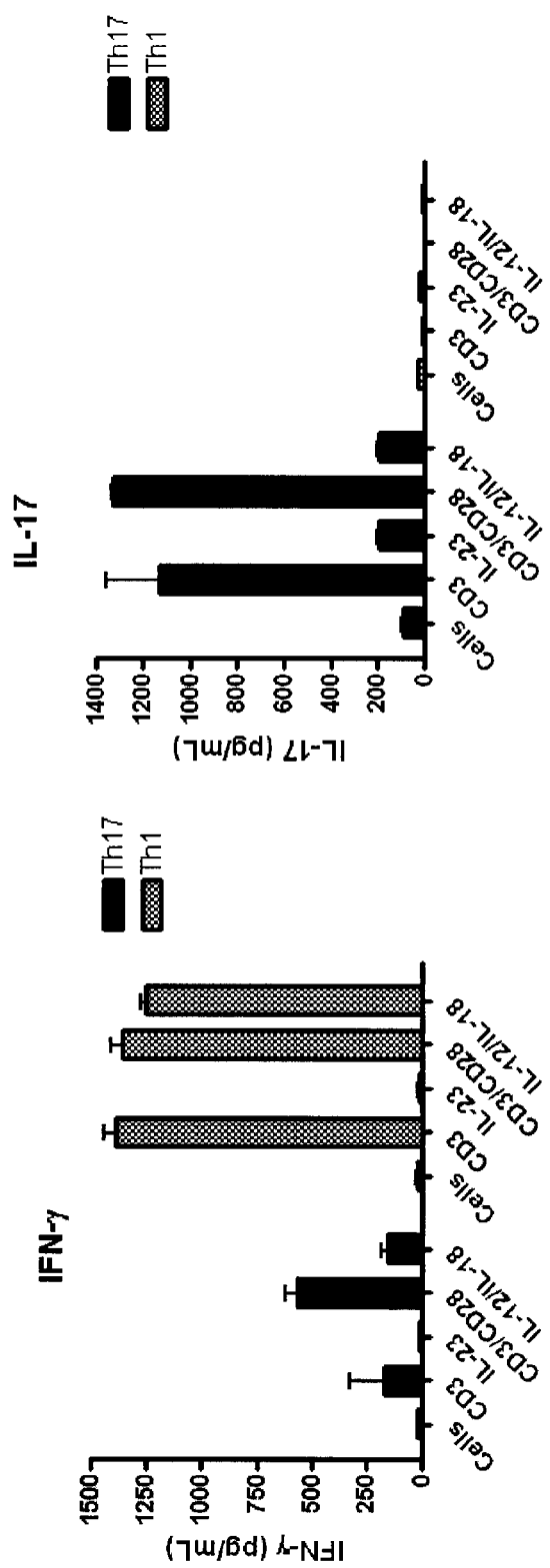
FIG. 1 illustrates the isolation of Th1 and Th17 cells from peripheral blood lymphocytes (PBL) isolated from blood by ficoll density gradient centrifugation. After removing monocytes, cells were cultured with 2 μg/mL PHA plus IL-12 and anti-IL-4 antibody for Th1 cells. Th17 cells were stimulated with plate-bound anti-CD3 antibody plus soluble anti-CD28 antibody or IL-12 plus IL-18 for 2 days at 37° C. Cell culture supernatants were collected and measured for production of IFN-γ and IL-17 by ELISA.
Figure 2:
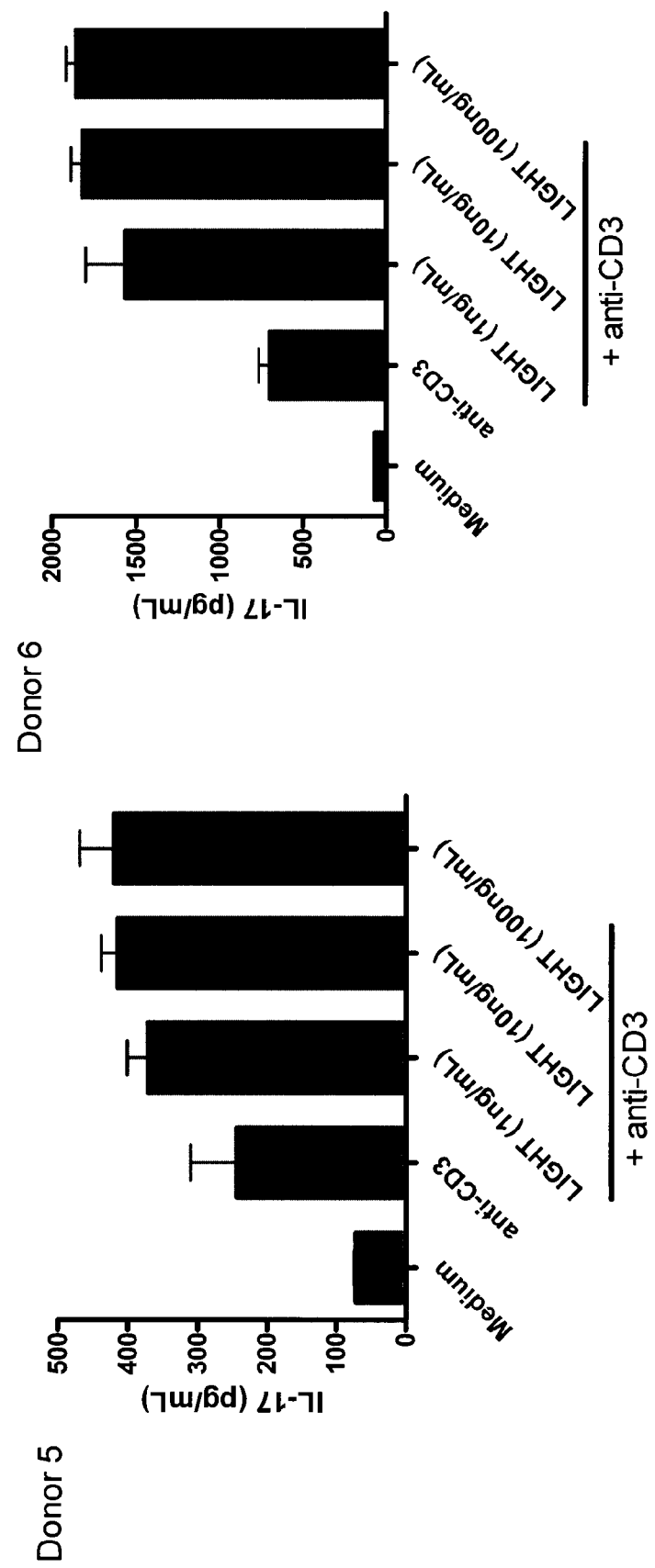
FIG. 2 illustrates how LIGHT induces IL-17 production in Th17 cells. Th17 cells were stimulated with plate-bound anti-CD3 antibody in the absence or presence of various concentrations of LIGHT for 2 days at 37° C. Cell culture supernatants were collected and measured for production IL-17 by ELISA.

It is to be noted that the term "a" or "an" entity refers to one or more of that entity; for example, "an antigen-binding polypeptide," is understood to represent one or more antigen-binding polypeptides. As such, the terms "a" (or "a"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposes of the invention, as are native or recombinant polypeptides which have been separated, fractionated, or partially or substantially purified by any suitable technique.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody of the present invention contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an antigen-binding polypeptide of the present invention or variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

An "antibody" or "antibody molecule", as described herein, refers to a full-length (i.e., naturally occurring or formed by normal immunoglobulin gene fragment recombinatorial processes) immunoglobulin molecule (e.g., an IgG antibody).

The present invention includes certain antigen-binding polypeptides which bind LIGHT including antibodies, antibody or antigen-binding fragments, variants or derivatives thereof. Unless specifically referring to full-size antibodies, as described above, the term "antigen-binding polypeptide" encompasses full-sized antibodies as well as "antigen-binding fragments", variants, analogs or derivatives of such antibodies, e.g. naturally occurring antibody or immunoglobulin molecules or engineered antibody molecules or fragments that bind antigen in a manner similar to antibody molecules—Fab fragments, scFv molecules, etc. Antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains.

The terms "antibody fragment" or "antigen-binding fragment", as used herein, is a portion of an antibody such as F(ab')2, F(ab)2, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), scFv HSA fusion polypeptides in which the scFv is expressed as a fusion to either the N or C terminus of HSA, Fab' HSA fusion polypeptides in which the VH-CH1 or VK-CK are produced as a fusion to HSA, which then folds with its cognate VK-CK light chain or VH-CH1 heavy chain, respectively, to form a Fab', and minimal recognition units consisting of the amino acid residues that mimic the hypervariable region.

The terms "antigen-binding polypeptide" and "immunoglobulin" are used interchangeably herein. An antigen-binding polypeptide or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., *Antibodies: A Laboratory Manual*, (Cold Spring Harbor Laboratory Press, 2nd ed. 1988).

As will be discussed in more detail below, the term "antigen-binding polypeptide" comprises various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196: 901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

|         | Kabat  | Chothia |
|---------|--------|---------|
| CDR-H1  | 31-35  | 26-32   |
| CDR-H2  | 50-65  | 52-58   |
| CDR-H3  | 95-102 | 95-102  |
| CDR-L1  | 24-34  | 26-32   |
| CDR-L2  | 50-56  | 50-52   |
| CDR-L3  | 89-97  | 91-96   |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to Table 1 above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antigen-binding polypeptides, variants, or derivatives thereof of the invention include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antigen-binding polypeptides disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a antigen-binding polypeptide for use in the invention may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antigen-binding polypeptides disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds," it is generally meant that an antigen-binding polypeptide binds to an epitope via its antigen-binding domain, and that the binding entails some complementarity between the antigen-binding domain and the epitope. According to this definition, an antigen-binding polypeptide is said to "specifically bind" to an epitope when it binds to that epitope, via its antigen-binding domain more readily than it would bind to a random, unrelated epitope. The term "specificity" is used herein to qualify the relative affinity by which a certain antigen-binding polypeptide binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antigen-binding polypeptide specifically binds to an epitope more readily than it would bind to a related, similar, homologous, or analogous epitope. Thus, an antigen-binding polypeptide which "preferentially binds" to a given epitope would more likely bind to that epitope than to a related epitope, even though such an antibody may cross-react with the related epitope.

By way of non-limiting example, an antigen-binding polypeptide may be considered to bind a first epitope preferentially if it binds said first epitope with a dissociation constant ($K_D$) that is less than the antigen-binding polypeptide's $K_D$ for the second epitope. In another non-limiting example, an antigen-binding polypeptide may be considered to bind a first antigen preferentially if it binds the first epitope with an affinity that is at least one order of magnitude less than the antigen-binding polypeptide's $K_D$ for the second epitope. In another non-limiting example, an antigen-binding polypeptide may be considered to bind a first epitope preferentially if it binds the first epitope with an affinity that is at least two orders of magnitude less than the antigen-binding polypeptide's $K_D$ for the second epitope.

Antigen-binding polypeptides or variants or derivatives thereof of the invention may also be described or specified in terms of their binding affinity to a LIGHT polypeptide. Preferred binding affinities include those with a dissociation constant or $K_D$ less than $5\times10^{-2}$ M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, or $10^{-15}$M.

In another non-limiting example, an antigen-binding polypeptide may be considered to bind a first epitope preferentially if it binds the first epitope with an off rate ($k_{(off)}$) that is less than the antigen-binding polypeptide's $k_{(off)}$ for the second epitope. In another non-limiting example, an antigen-binding polypeptide may be considered to bind a first epitope preferentially if it binds the first epitope with an affinity that is at least one order of magnitude less than the antigen-binding polypeptide's $k_{(off)}$ for the second epitope. In another non-limiting example, an antigen-binding polypeptide may be considered to bind a first epitope preferentially if it binds the first epitope with an affinity that is at least two orders of magnitude less than the antigen-binding polypeptide's $k_{(off)}$ for the second epitope.

An antigen-binding polypeptide or variant, or derivative disclosed herein may be said to bind a target LIGHT polypeptide disclosed herein or a fragment or variant thereof with an off rate ($k_{(off)}$) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, an antigen-binding polypeptide of the invention may be said to bind a target LIGHT polypeptide disclosed herein or a fragment or variant thereof with an off rate ($k_{(off)}$) less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$.

An antigen-binding polypeptide or variant, or derivative disclosed herein may be said to bind a LIGHT target polypeptide disclosed herein or a fragment or variant thereof with an on rate ($k_{(on)}$) of greater than or equal to $10^{3}$M$^{-1}$ sec$^{-1}$, $5\times10^{3}$M$^{-1}$ sec$^{-1}$, $10^{4}$M$^{-1}$ sec$^{-1}$ or $5\times10^{4}$M$^{-1}$ sec$^{-1}$. More preferably, an antigen-binding polypeptide of the invention may be said to bind a target LIGHT polypeptide disclosed herein or a fragment or variant thereof with an on rate ($k_{(on)}$) greater than or equal to $10^{5}$M$^{-1}$ sec$^{-1}$, $5\times10^{5}$M$^{-1}$ sec$^{-1}$, $10^{6}$M$^{-1}$ sec$^{-1}$, $5\times10^{6}$M$^{-1}$ sec$^{-1}$ or $10^{7}$M$^{-1}$ sec$^{-1}$, $5\times10^{7}$M$^{-1}$ sec$^{-1}$.

An antigen-binding polypeptide is said to competitively inhibit binding of a reference antigen-binding polypeptide to a given epitope if it preferentially binds to that epitope to the extent that it blocks, to some degree, binding of the reference antigen-binding polypeptide to the epitope. Competitive inhibition may be determined by any method known in the art, for example, competition ELISA assays. An antigen-binding polypeptide may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., *Antibodies: A Laboratory Manual*, (Cold Spring Harbor Laboratory Press, 2nd ed. 1988) at pages 27-28. As used herein, the term "avidity" refers to the overall stability of the complex between a population of antigen-binding polypeptide and an antigen, that is, the functional combining strength of an immunoglobulin mixture with the antigen. See, e.g., Harlow at pages 29-34. Avidity is related to both the affinity of individual antigen-binding polypeptides in the population with specific epitopes, and also the valencies of the antigen-binding polypeptides and the antigen. For example, the interaction between a bivalent monoclonal antibody and an antigen with a highly repeating epitope structure, such as a polymer, would be one of high avidity.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen-binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded polypeptide" includes polypeptides (e.g., antigen-binding polypeptides) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "conjugated," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" or "express" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antigen-binding polypeptide or composition of the present invention used, e.g., for detection, for a diagnostic procedure and/or for treatment.

LIGHT Antibodies

Disclosed are antigen-binding polypeptides that bind specifically to the TNF-like cytokine polypeptide known as LIGHT (see GenBank accession no. AF036581, incorporated herein by reference in its entirety). Certain antigen-binding polypeptides of the present invention include humanized heavy chain polypeptides, humanized light chain polypeptides, humanized heavy chain variable regions, humanized light chain variable regions, as well as humanized heavy and light chain polypeptides which comprise the complementary determining regions of the LIGHT antibodies described herein. In certain embodiments, the antigen-binding polypeptides function as antagonists of LIGHT activity and/or LIGHT interaction with LIGHT receptors.

For example, certain antigen-binding polypeptides of the present invention include the framework (FR) regions of the light and heavy chain variable regions of a human antibody, while retaining substantially the antigen-binding specificity of a parental monoclonal antibody. The humanized heavy chain variable region and/or the humanized light chain variable region are at least about 87% humanized, at least about 88% humanized, at least about 89% humanized, at least about 90% humanized, at least about 91% humanized, at least about 92% humanized, at least about 93% humanized, at least about 94% humanized, at least about 95% humanized, at least about 96% humanized, at least about 97% humanized, at least about 98% humanized, at least about 99% humanized, or at least about 100% humanized, not including the complementary-determining regions (CDRs).

The antigen-binding polypeptides molecules of the present invention include, but are not limited to, polyclonal, monoclonal, multispecific, human, humanized, chimeric, single chain antibodies, Fab fragments, F(ab') fragments and anti-idiotypic (anti-Id) antibodies. Antigen-binding polypeptides of the present invention also include, but are not limited to Fab, Fab' and F(ab')2, Fv, single-chain Fvs (scFV), single-chain antibodies, disulfide linked Fvs (sdFv) and fragments comprising either a variable light or variable heavy domain. Antigen-binding polypeptides of the present invention, including single-chain antibodies, may comprise the variable region(s) alone or in combination with the entirety or a portion of a heavy chain constant region or a light chain constant region, hinge region, CH1, CH2, and CH3 domains.

The antigen-binding polypeptides of the present invention may be derived from any animal origin including human, murine, donkey, sheep, rabbit, goat, pig, camel, horse or chicken. For example, the antigen-binding polypeptide of the present invention may be derived from monoclonal antibody donors (e.g., mouse monoclonal antibody donors) and may include CDRs from the monoclonal antibodies (e.g., mouse monoclonal CDRs).

In certain embodiments, the present invention is directed to antigen-binding polypeptides or variants or derivatives thereof. Specifically, the present invention includes antigen-binding polypeptides which specifically bind to the LIGHT polypeptide and comprise, consist essentially of, or consist of a humanized heavy chain variable region comprising, consisting essentially of, or consisting of the amino acid sequences described below in Table 2:

TABLE 2

Amino Acid Sequence of Heavy Chain Variable Domains of Humanized Anti-LIGHT Antibodies

| SEQ ID NO | Sequence | Name |
|---|---|---|
| 1 | QVQLVQSGAEVKKPGASVKVSCKASGYTFTX1YX2X3X4WVR QAPGQX'$_1$LEWX'$_2$G X5IX6PX7X8X9X10X11X12X13NX14X15FX16X17 X'$_3$X'$_4$TX'$_5$TX'$_6$DX'$_7$SX'$_8$STX'$_9$YMELSX'$_{10}$LRSX'$_{11}$DTAVYYCAR WX18X19WGQGTLVTVSS<br>X1 = D, S, T or N     X'$_1$ = R or G<br>X2 = Y, L or W     X'$_2$ = M or I<br>X3 = I or M     X'$_3$ = K or R<br>X4 = Y, H, E or N     X'$_4$ = V or A<br>X5 = Y, M, V or W     X'$_5$ = M, L or I<br>X6 = D, N, H or F     X'$_6$ = V or R<br>X7 = Y, G or S     X'$_7$ = T or K<br>X8 = N, S, T or D     X'$_8$ = A, I or T<br>X9 = G, S or D     X'$_9$ = V or A<br>X10 = G, D, E or I     X'$_{10}$ = R or S<br>X11 = T or S     X'$_{11}$ = D or E<br>X12 = K or R<br>X13 = Y or L<br>X14 = Q or E<br>X15 = K or N<br>X16 = K, I or R<br>X17 = G, A or D<br>X18 = D or N<br>X19 = R or Y | VH-CDR-H3a |
| 2 | QVQLVQSGAEVKKPGASVKVSCKASGYTFTX1YX2X3X4WVR QAPGQX'$_1$LEWX'$_2$G X5IX6PX7X8X9X10X11X12X13NX14X15FX16X17 X'$_3$X'$_4$TX'$_5$TX'$_6$DX'$_7$SX'$_8$STX'$_9$YMELSX'$_{10}$LRSX'$_{11}$DTAVYYCAR X20X21X22X23X24X25X26X27X28WGQGTLVTVSS<br>X1 = D, S, T or N     X'$_1$ = R or G<br>X2 = Y, L or W     X'$_2$ = M or I<br>X3 = I or M     X'$_3$ = K or R<br>X4 = Y, H, E or N     X'$_4$ = V or A<br>X5 = Y, M, V or W     X'$_5$ = M, L or I<br>X6 = D, N, H or F     X'$_6$ = V or R<br>X7 = Y, G or S     X'$_7$ = T or K<br>X8 = N, S, T or D     X'$_8$ = A, I or T<br>X9 = G, S or D     X'$_9$ = V or A<br>X10 = G, D, E or I     X'$_{10}$ = R or S<br>X11 = T or S     X'$_{11}$ = D or E<br>X12 = K or R<br>X13 = Y or L<br>X14 = Q or E<br>X15 = K or N<br>X16 = K, I or R<br>X17 = G, A or D<br>X18 = D or N<br>X19 = R or Y<br>X20 = E, T or G<br>X21 = D, S or N<br>X22 = Y or G<br>X23 = G, S or V<br>X24 = I, S or W<br>X25 = S, W or A<br>X26 = T, F or M<br>X27 = Y, P or D<br>X28 = S or Y | VH-CDR-H3b |
| 3 | QVQLVQSGAEVKKPGASVKVSCKASGYTFTX1YX2X3X4WVR QAPGQX'$_1$LEWX'$_2$G X5IX6PX7X8X9X10X11X12X13NX14X15FX16X17 X'$_3$X'$_4$TX'$_5$TX'$_6$DX'$_7$SX'$_8$STX'$_9$YMELSX'$_{10}$LRSX'$_{11}$DTAVYYCAR X20X21X22X23X24X25X26X27X28AMDFWGQGTLVTVSS<br>X1 = D, S, T or N     X'$_1$ = R or G<br>X2 = Y, L or W     X'$_2$ = M or I<br>X3 = I or M     X'$_3$ = K or R<br>X4 = Y, H, E or N     X'$_4$ = V or A | VH-CDR-H3c |

TABLE 2-continued

Amino Acid Sequence of Heavy Chain Variable Domains of Humanized Anti-LIGHT Antibodies

| SEQ ID NO | Sequence | Name |
|---|---|---|
| | $X_5$ = Y, M, V or W     $X'_5$ = M, L or I | |
| | $X_6$ = D, N, H or F     $X'_6$ = V or R | |
| | $X_7$ = Y, G or S        $X'_7$ = T or K | |
| | $X_8$ = N, S, T or D     $X'_8$ = A, I or T | |
| | $X_9$ = G, S or D        $X'_9$ = V or A | |
| | $X_{10}$ = G, D, E or I  $X'_{10}$ = R or S | |
| | $X_{11}$ = T or S        $X'_{11}$ = D or E | |
| | $X_{12}$ = K or R | |
| | $X_{13}$ = Y or L | |
| | $X_{14}$ = Q or E | |
| | $X_{15}$ = K or N | |
| | $X_{16}$ = K, I or R | |
| | $X_{17}$ = G, A or D | |
| | $X_{18}$ = D or N | |
| | $X_{19}$ = R or Y | |
| | $X_{20}$ = E, T or G | |
| | $X_{21}$ = D, S or N | |
| | $X_{22}$ = Y or G | |
| | $X_{23}$ = G, S or V | |
| | $X_{24}$ = I, S or W | |
| | $X_{25}$ = S, W or A | |
| | $X_{26}$ = T, F or M | |
| | $X_{27}$ = Y, P or D | |
| | $X_{28}$ = S or Y | |
| 4 | QVQLVQSGAEVKKPGASVKVSCKASGYTFTSYYIHWVRQAP GQRLEWMGWIFPGSDITKYNEKFKGRVTITRDTSASTAYM ELSSLRSEDTAVYYCAREDYGISTYSAMDFWGQGTLVTVSS | h5E10 VH1 |
| 5 | QVQLVQSGAEVKKPGASVKVSCKASGYTFTDYYIYWVRQA PGQGLEWIGYIDPYNGGTKYNQKFKDRVTMTRDTSISTAY MELSRLRSDDTAVYYCARTSGSSWFPYWGQGTLVTVSS | h10D11-VH1 |
| 6 | QVQLVQSGAEVKKPGASVKVSCKASGYTFTDYYIYWVRQA PGQGLEWIGYIDPYNGGTKYNQKFKDKATLTVDKSTSTAY MELSSLRSEDTAVYYCARTSGSSWFPYWGQGTLVTVSS | h10D11-VH2 |
| 7 | QVQLVQSGAEVKKPGASVKVSCKASGYTFTTYLIEWVRQAP GQGLEWMGVINPGTGETKYNENFRARVTMTRDTSISTAYM ELSRLRSDDTAVYYCARWDRWGQGTLVTVSS | h14G8 VH1 |
| 8 | QVQLVQSGAEVKKPGASVKVSCKASGYTFTTYWMNWVRQ APGQGLEWMGMIHPSDSESRLNQKFIDRVTMTRDTSTSTVY MELSSLRSEDTAVYYCARGNYVWAMDYWGQGTLVTVSS | h18B1 VH1 |

The CDR regions of each humanzied variable heavy chain region are indicated in bold and underlined.

In certain embodiments, the antigen-binding polypeptide of the present invention is directed to a humanized antibody heavy chain variable region comprising, consisting essentially of, or consisting of the amino acid sequence selected from the group consisting of SEQ ID NO:1; SEQ ID NO:2; SEQ ID NO:3; SEQ ID NO:4; SEQ ID NO:5; SEQ ID NO:6; SEQ ID NO:7; and SEQ ID NO:8. Specifically, certain antigen-binding polypeptides of the present invention comprise, consist essentially of, or consist of a heavy chain variable region comprising, consisting essentially of, or consisting of the amino acid sequence of SEQ ID NO:4.

In one embodiment, the antigen-binding polypeptide of the present invention is directed to a fully humanized LIGHT antibody comprising the heavy chain variable regions described herein with a complete heavy chain (i.e. constant regions).

In another embodiment, the present invention provides an antigen-binding polypeptide, which specifically binds to the LIGHT polypeptide comprising, consisting essentially of, or consisting of a humanized heavy chain variable region comprising a CDR-H1, CDR-H2 and CDR-H3 region. In certain embodiments the CDR regions comprise, consist essentially of, or consist of an amino acid sequence selected from the group consisting of the sequences described below in Table 3.

TABLE 3

Amino Acid Sequence of Heavy Chain CDRs of Humanized Anti-LIGHT Antibodies

| SEQ ID NO | Sequence | Name |
|---|---|---|
| 18 | $X_1YX_2X_3X_4$<br>$X_1$ = D, S, T or N<br>$X_2$ = Y, L or W<br>$X_3$ = I or M<br>$X_4$ = Y, H, E or N | CDR-H1 |
| 19 | $X_5IX_6PX_7X_8X_9X_{10}X_{11}X_{12}X_{13}NX_{14}X_{15}FX_{16}X_{17}$<br>$X_5$ = Y, M, V or W<br>$X_6$ = D, N, H or F<br>$X_7$ = Y, G or S<br>$X_8$ = N, S, T or D<br>$X_9$ = G, S or D | CDR-H2 |

TABLE 3-continued

Amino Acid Sequence of Heavy Chain
CDRs of Humanized Anti-LIGHT Antibodies

| SEQ ID NO | Sequence | Name |
|---|---|---|
| | $X_{10}$ = G, D, E or I<br>$X_{11}$ = T or S<br>$X_{12}$ = K or R<br>$X_{13}$ = Y or L<br>$X_{14}$ = Q or E<br>$X_{15}$ = K or N<br>$X_{16}$ = K, I or R<br>$X_{17}$ = G, A or D | |
| 20 | $WX_{18}X_{19}$<br>$X_{18}$ = D or N<br>$X_{19}$ = R or Y | CDR-H3a |
| 21 | $X_{20}X_{21}X_{22}X_{23}X_{24}X_{25}X_{26}X_{27}X_{28}$<br>$X_{20}$ = E, T or G<br>$X_{21}$ = D, S or N<br>$X_{22}$ = Y or G<br>$X_{23}$ = G, S or V<br>$X_{24}$ = I, S or W<br>$X_{25}$ = S, W or A<br>$X_{26}$ = T, F or M<br>$X_{27}$ = Y, P or D<br>$X_{28}$ = S or Y | CDR-H3b |
| 22 | $X_{20}X_{21}X_{22}X_{23}X_{24}X_{25}X_{26}X_{27}X_{28}$AMDF<br>$X_{20}$ = E, T, or G<br>$X_{21}$ = D, S, or N<br>$X_{22}$ = Y or G<br>$X_{23}$ = G, S or V<br>$X_{24}$ = I, S or W<br>$X_{25}$ = S, W or A<br>$X_{26}$ = T, F or M<br>$X_{27}$ = Y, P or D<br>$X_{28}$ = S or Y | CDR-H3c |
| 23 | SYYIH | 5E10-CDR-H1 |
| 24 | WIFPGSDITKYNEKFKG | 5E10-CDR-H2 |
| 25 | EDYGISTYSAMDF | 5E10-CDR-H3 |
| 26 | DYYIY | 10D11-CDR-H1 |
| 27 | YIDPYNGGTKYNQKFKD | 10D11-CDR-H2 |
| 28 | TSGSSWFPY | 10D11-CDR-H3 |
| 29 | TYLIE | 14G8-CDR-H1 |
| 30 | VINPGTGETKYNENFRA | 14G8-CDR-H2 |
| 31 | WDR | 14G8-CDR-H3 |
| 32 | TYWMN | 18B1-CDR-H1 |
| 33 | MIHPSDSESRLNQKFID | 18B1-CDR-H2 |
| 34 | GNYVWAMDY | 18B1-CDR-H3 |
| 35 | NYLIE | 13C7-CDR-H1 |
| 36 | VINPGSGDTKYNENFKG | 13C7-CDR-H2 |
| 37 | WNY | 13C7-CDR-H3 |

In another embodiment, the present invention provides an antigen-binding polypeptide, which specifically binds to the LIGHT polypeptide, comprising, consisting essentially of, or consisting of a humanized heavy chain variable region comprising a CDR-H1, CDR-H2 and CDR-H3 region. In certain embodiments the CDR-H1 region comprises, consists essentially of, or consists of the amino acid sequence selected from the group consisting of: SEQ ID NO:18; SEQ ID NO:23; SEQ ID NO:26; SEQ ID NO:29; SEQ ID NO:32; and SEQ ID NO:35. In certain embodiments the CDR-H2 region comprises, consists essentially of, or consists of the amino acid sequence selected from the group consisting of: SEQ ID NO:19; SEQ ID NO:24; SEQ ID NO:27; SEQ ID NO:30; SEQ ID NO:33; and SEQ ID NO:36. In certain embodiments the CDR-H3 region comprises, consists essentially of or consists of the amino acid sequence selected from the group consisting of: SEQ ID NO:20; SEQ ID NO:21; SEQ ID NO:22; SEQ ID NO:25; SEQ ID NO:28; SEQ ID NO:31; SEQ ID NO:34; and SEQ ID NO:37.

In specific embodiments, the present invention includes an antigen-binding polypeptide, which specifically binds to the LIGHT polypeptide, comprising, consisting essentially of, or consisting of a humanized heavy chain variable region comprising a CDR-H1 region comprising, consisting essentially of, or consisting of the amino acid sequence of SEQ ID NO:23, a CDR-H2 region comprising, consisting essentially of, or consisting of the amino acid sequence of SEQ ID NO:24 and a CDR-H3 region comprising, consisting essentially of, or consisting of the amino acid sequence of SEQ ID NO:25.

Antigen-binding polypeptides which specifically bind to the LIGHT polypeptide may comprise, consist essentially of, or consist of a humanized heavy chain variable region comprising any of the CDR-heavy chain regions disclosed herein in any combination.

The present invention also includes an antigen-binding polypeptide, which specifically binds to the LIGHT polypeptide, comprising, consisting essentially of, or consisting of a humanized light chain variable region comprising, consisting essentially of, or consisting of the amino acid sequence described below in Table 4.

TABLE 4

Amino Acid Sequence of Light Chain Variable
Domains of Humanized Anti-LIGHT Antibodies

| SEQ ID NO | Sequence | Name |
|---|---|---|
| 9 | $X'_{12}X'_{13}X'_{14}X'_{15}$TQX$'_{16}$PX$'_{17}X'_{18}X'_{19}X'_{20}$<br>$X'_{21}X'_{22}X'_{23}X'_{24}X'_{25}X'_{26}X'_{27}X'_{28}X'_{29}X'_{30}$C<br>X29X30SX31X32X33X34X35X36X37X38WX$'_{31}X'_{32}$Q<br>$X'_{33}$PX$'_{34}X'_{35}X'_{36}$PX$'_{37}X'_{38}$LIX$'_{39}$<br>X43X44X45X46X47X48X49GX$'_{40}$PX$'_{41}$RFSGSGSGT<br>$X'_{42}$FTLX$'_{43}$IX$'_{44}X'_{45}X'_{46}X'_{47}X'_{48}$EDX$'_{49}$<br>$X'_{50}X'_{51}$YYCX50X51X52X53X54X55PX56TFGQGT<br>$X'_{52}$VEIKR<br><br>X29 = K or R    $X'_{12}$ = D or E<br>X30 = A or S    $X'_{13}$ = I or V<br>X31 = Q or K    $X'_{14}$ = V or Q<br>X32 = D, S or N    $X'_{15}$ = M or L<br>X33 = V, I or L    $X'_{16}$ = S or T<br>X34 = G, S, V or L    $X'_{17}$ = S, D, A or L<br>X35 = T, N or H    $X'_{18}$ = S, T or F<br>X36 = A, N or S    $X'_{19}$ = L or Q<br>X37 = V, L, N or G    $X'_{20}$ = A, S or P<br>X38 = A, H, G or Y    $X'_{21}$ = V or A<br>X39 = N or T    $X'_{22}$ = S or T<br>X40 = T or Y    $X'_{23}$ = P, L or V<br>X41 = Y or M    $X'_{24}$ = G or K<br>X42 = F or H    $X'_{25}$ = E, Q or D<br>X43 = W, Y, K or I    $X'_{26}$ = R, K or P<br>X44 = A, T or V    $X'_{27}$ = A or V<br>X45 = S or Y    $X'_{28}$ = T or S<br>X46 = T, Q or N    $X'_{29}$ = I or L<br>X47 = R, S or L    $X'_{30}$ = S, T or N<br>X48 = H, I, F or E    $X'_{31}$ = F or Y<br>X49 = T or S    $X'_{32}$ = Q or L<br>X50 = Q or S    $X'_{33}$ = K or R<br>X51 = Q or H    $X'_{34}$ = G or D | VK-CDR-L1a |

TABLE 4-continued

Amino Acid Sequence of Light Chain Variable Domains of Humanized Anti-LIGHT Antibodies

| SEQ ID NO | Sequence | Name |
|---|---|---|
| | X52 = S or Y    X'$_{35}$ = Q or K | |
| | X53 = S, N, T or R    X'$_{36}$ = A, S or P | |
| | X54 = S, R, H or E    X'$_{37}$ = K, R or Q | |
| | X55 = Y, W, V or L    X'$_{38}$ = L or R | |
| | X56 = L or Y    X'$_{39}$ = Y or K | |
| | X'$_{40}$ = V or I | |
| | X'$_{41}$ = S, A, or D | |
| | X'$_{42}$ = D or E | |
| | X'$_{43}$ = K or T | |
| | X'$_{44}$ = S or N | |
| | X'$_{45}$ = S or R | |
| | X'$_{46}$ = V or L | |
| | X'$_{47}$ = Q or E | |
| | X'$_{48}$ = P, A or S | |
| | X'$_{49}$ = F, A or V | |
| | X'$_{50}$ = A or G | |
| | X'$_{51}$ = T or V | |
| | X'$_{52}$ = R or K | |
| 10 | X'$_{12}$X'$_{13}$X'$_{14}$X'$_{15}$TQX'$_{16}$PX'$_{17}$X'$_{18}$X'$_{19}$X'$_{20}$ X'$_{21}$X'$_{22}$X'$_{23}$X'$_{24}$X'$_{25}$X'$_{26}$X'$_{27}$X'$_{28}$X'$_{29}$X'$_{30}$C X29X30SX31X32X33X34X35X36X37X38X39X40X41X42H WX'$_{31}$X'$_{32}$QX'$_{33}$PX'$_{34}$X'$_{35}$X'$_{36}$PX'$_{37}$X'$_{38}$LIX'$_{39}$ X43X44X45X46X47X48X49GX'$_{40}$PX'$_{41}$RFSGSGSTX'$_{42}$ FTLX'$_{43}$IX'$_{44}$X'$_{45}$X'$_{46}$X'$_{47}$X'$_{48}$EDX'$_{49}$X'$_{50}$X'$_{51}$YYC X50X51X52X53X54X55PX56TFGQGTX'$_{52}$VEIKR | VK-CDR-L1b |
| | X29 = K or R    X'$_{12}$ = D or E | |
| | X30 = A or S    X'$_{13}$ = I or V | |
| | X31 = Q or K    X'$_{14}$ = V or Q | |
| | X32 = D, S or N    X'$_{15}$ = M or L | |
| | X33 = V, I or L    X'$_{16}$ = S or T | |
| | X34 = G, S, V or L    X'$_{17}$ = S, D, A or L | |
| | X35 = T, N or H    X'$_{18}$ = S, T or F | |
| | X36 = A, N or S    X'$_{19}$ = L or Q | |
| | X37 = V, L, N or G    X'$_{20}$ = A, S or P | |
| | X38 = A, H, G or Y    X'$_{21}$ = V or A | |
| | X39 = N or T    X'$_{22}$ = S or T | |
| | X40 = T or Y    X'$_{23}$ = P, L or V | |
| | X41 = Y or M    X'$_{24}$ = G or K | |
| | X42 = F or H    X'$_{25}$ = E, Q or D | |
| | X43 = W, Y, K or I    X'$_{26}$ = R, K or P | |
| | X44 = A, T or V    X'$_{27}$ = A or V | |
| | X45 = S or Y    X'$_{28}$ = T or S | |
| | X46 = T, Q or N    X'$_{29}$ = I or L | |
| | X47 = R, S or L    X'$_{30}$ = S, T or N | |
| | X48 = H, I, F or E    X'$_{31}$ = F or Y | |
| | X49 = T or S    X'$_{32}$ = Q or L | |
| | X50 = Q or S    X'$_{33}$ = K or R | |
| | X51 = Q or H    X'$_{34}$ = G or D | |
| | X52 = S or Y    X'$_{35}$ = Q or K | |
| | X53 = S, N, T or R    X'$_{36}$ = A, S or P | |
| | X54 = S, R, H or E    X'$_{37}$ = K, R or Q | |
| | X55 = Y, W, V or L    X'$_{38}$ = L or R | |
| | X56 = L or Y    X'$_{39}$ = Y or K | |
| | X'$_{40}$ = V or I | |
| | X'$_{41}$ = S, A or D | |
| | X'$_{42}$ = D or E | |
| | X'$_{43}$ = K or T | |
| | X'$_{44}$ = S or N | |
| | X'$_{45}$ = S or R | |
| | X'$_{46}$ = V or L | |
| | X'$_{47}$ = Q or E | |
| | X'$_{48}$ = P, A or S | |
| | X'$_{49}$ = F, A or V | |
| | X'$_{50}$ = A or G | |
| | X'$_{51}$ = T or V | |
| | X'$_{52}$ = R or K | |
| 11 | X'$_{12}$X'$_{13}$X'$_{14}$X'$_{15}$TQX'$_{16}$PX'$_{17}$X'$_{18}$X'$_{19}$X'$_{20}$ X'$_{21}$X'$_{22}$X'$_{23}$X'$_{24}$X'$_{25}$X'$_{26}$X'$_{27}$X'$_{28}$X'$_{29}$X'$_{30}$C X29X30SX31X32X33X34X35X36X37X38X39X40X41X42H WX'$_{31}$X'$_{32}$QX'$_{33}$PX'$_{34}$X'$_{35}$X'$_{36}$PX'$_{37}$X'$_{38}$LIX'$_{39}$ X43X44X45X46X47X48X49GX'$_{40}$PX'$_{41}$RFSGSGSTX'$_{42}$ FTLX'$_{43}$IX'$_{44}$X'$_{45}$X'$_{46}$X'$_{47}$X'$_{48}$EDX'$_{49}$X'$_{50}$X'$_{51}$YYC X50X51X52X53X54X55PX56TFGQGTX'$_{52}$VEIKR | VK-CDR-L1c |
| | X29 = K or R    X'$_{12}$ = D or E | |
| | X30 = A or S    X'$_{13}$ = I or V | |
| | X31 = Q or K    X'$_{14}$ = V or Q | |
| | X32 = D, S or N    X'$_{15}$ = M or L | |
| | X33 = V, I or L    X'$_{16}$ = S or T | |
| | X34 = G, S, V or L    X'$_{17}$ = S, D, A or L | |
| | X35 = T, N or H    X'$_{18}$ = S, T or F | |
| | X36 = A, N or S    X'$_{19}$ = L or Q | |
| | X37 = V, L, N or G    X'$_{20}$ = A, S or P | |
| | X38 = A, H, G or Y    X'$_{21}$ = V or A | |
| | X39 = N or T    X'$_{22}$ = S or T | |
| | X40 = T or Y    X'$_{23}$ = P, L or V | |
| | X41 = Y or M    X'$_{24}$ = G or K | |
| | X42 = F or H    X'$_{25}$ = E, Q or D | |
| | X43 = W, Y, K or I    X'$_{26}$ = R, K or P | |
| | X44 = A, T or V    X'$_{27}$ = A or V | |
| | X45 = S or Y    X'$_{28}$ = T or S | |
| | X46 = T, Q or N    X'$_{29}$ = I or L | |
| | X47 = R, S or L    X'$_{30}$ = S, T or N | |
| | X48 = H, I, F or E    X'$_{31}$ = F or Y | |
| | X49 = T or S    X'$_{32}$ = Q or L | |
| | X50 = Q or S    X'$_{33}$ = K or R | |
| | X51 = Q or H    X'$_{34}$ = G or D | |
| | X52 = S or Y    X'$_{35}$ = Q or K | |
| | X53 = S, N, T or R    X'$_{36}$ = A, S or P | |
| | X54 = S, R, H or E    X'$_{37}$ = K, R or Q | |
| | X55 = Y, W, V or L    X'$_{38}$ = L or R | |
| | X56 = L or Y    X'$_{39}$ = Y or K | |
| | X'$_{40}$ = V or I | |
| | X'$_{41}$ = S, A or D | |
| | X'$_{42}$ = D or E | |
| | X'$_{43}$ = K or T | |
| | X'$_{44}$ = S or N | |
| | X'$_{45}$ = S or R | |
| | X'$_{46}$ = V or L | |
| | X'$_{47}$ = Q or E | |
| | X'$_{48}$ = P, A or S | |
| | X'$_{49}$ = F, A or V | |
| | X'$_{50}$ = A or G | |
| | X'$_{51}$ = T or V | |
| | X'$_{52}$ = R or K | |
| 12 | DIQLTQSPSFLSAVGDRVTITCKASQDVGTAVAWYQ QKPGKAPKLLIYWASTRHTGVPSRFSGSGSGTEFTL TISSLQPEDFATYYCQQYSSYPLTFGQGTKVEIKR | h5E10 VK1 |
| 13 | EIVLTQSPDFQSVTPKEKVTITCRASQSISNNLHWY QQKPDQSPKLLIKYTYQSISGVPSRFSGSGSGTDPFT LTINSLEAEDAATYYCQQSNRWPLTFGQGTKVEIKR | h10D11-VK1 |
| 14 | EIVMTQSPATLSVSPGEKATLSCRASQSISNNLHWY QQKPGQAPRLLIYYTYQSISGIPARFSGSGSGTEFT LTISSLQSEDFAVYYCQQSNRWPLTFGQGTRVEIKR | h10D11-VK2 |
| 15 | DVVMTQSPLSLPVTLGQPASISCRSSQNLVHSNGNT YFHWFQQRPGQSPRRLIYKVSNRFSGVPDRFSGSGS GTDFTLKISRVEAEDVGVYYCSQSTHVPYTFGQGTK VEIKR | h14G8-VK1 |

TABLE 4-continued

Amino Acid Sequence of Light Chain Variable
Domains of Humanized Anti-LIGHT Antibodies

| SEQ ID NO | Sequence | Name |
|---|---|---|
| 16 | DIVMTQTPLSLSVTPGQPASISCRSSQNLVHSNGNT YFHWYLQKPGQSPQLLIYKVSNRFSGVPDRFSGSGS GTDFTLKISRVEAEDVGVYYCSQSTHVPYTFGQGTK VEIKR | h14G8-VK2 |
| 17 | DIVMTQSPDSLAVSLGERATINCRASKSVSTSGYTY MHWYQQKPGQPPKLLIYITSNLESGVPDRFSGSGSG TDFTLTISSLQAEDVAVYYCQHSRELPYTFGQGTKV EIKR | h18B1-VK1 |

The CDR regions of each humanized variable light chain region are indicated in bold and underlined.

In certain embodiments, the antigen-binding polypeptide of the present invention is directed to a humanized antibody light chain variable region comprising, consisting essentially of, or consisting of the amino acid sequence selected from the group consisting of SEQ ID NO:9; SEQ ID NO:10; SEQ ID NO:11; SEQ ID NO:12; SEQ ID NO:13; SEQ ID NO:14; SEQ ID NO:15; SEQ ID NO:16; and SEQ ID NO:17. Specifically, certain antigen-binding polypeptides of the present invention comprise, consist essentially of, or consist of a light chain variable region comprising, consisting essentially of, or consisting of the amino acid sequence of SEQ ID NO:12.

In one embodiment, the antigen-binding polypeptide of the present invention is directed to a fully humanized LIGHT antibody comprising the light chain variable regions described herein with a complete light chain (i.e. constant regions).

In another embodiment, the present invention provides an antigen-binding polypeptide, which specifically binds to the LIGHT polypeptide comprising, consisting essentially of, or consisting of a humanized light chain variable region comprising a CDR-L1, CDR-L2 and CDR-L3 region described in Table 5 below.

TABLE 5

Amino Acid Sequence of Light Chain CDRs
of Humanized Anti-LIGHT Antibodies

| SEQ ID NO | Sequence | Name |
|---|---|---|
| 38 | $X_{29}X_{30}X_{31}X_{32}X_{33}X_{34}X_{35}X_{36}X_{37}X_{38}$<br>$X_{29}$ = K or R<br>$X_{30}$ = A or S<br>$X_{31}$ = Q or K<br>$X_{32}$ = D, S or N<br>$X_{33}$ = V, I or L<br>$X_{34}$ = G, S, V or L<br>$X_{35}$ = T, N, or H<br>$X_{36}$ = A, N or S<br>$X_{37}$ = V, L, N or G<br>$X_{38}$ = A, H G or Y | CDR-L1a |
| 39 | $X_{29}X_{30}SX_{31}X_{32}X_{33}X_{34}X_{35}X_{36}X_{37}X_{38}X_{39}X_{40}X_{41}X_{42}$<br>$X_{29}$ = K or R<br>$X_{30}$ = A or S<br>$X_{31}$ = Q or K<br>$X_{32}$ = D, S or N<br>$X_{33}$ = V, I or L<br>$X_{34}$ = G, S, V or L<br>$X_{35}$ = T, N or H<br>$X_{36}$ = A, N or S<br>$X_{37}$ = V, L, N or G<br>$X_{38}$ = A, H, G or Y<br>$X_{39}$ = N or T<br>$X_{40}$ = T or Y<br>$X_{41}$ = Y or M<br>$X_{42}$ = F or H | CDR-L1b |
| 40 | $X_{29}X_{30}SX_{31}X_{32}X_{33}X_{34}X_{35}X_{36}X_{37}X_{38}X_{39}X_{40}X_{41}X_{42}$HFR<br>$X_{29}$ = K or R<br>$X_{30}$ = A or S<br>$X_{31}$ = Q or K<br>$X_{32}$ = D, S or N<br>$X_{33}$ = V, I or L<br>$X_{34}$ = G, S, V or L<br>$X_{35}$ = T, N or H<br>$X_{36}$ = A, N or S<br>$X_{37}$ = V, L, N or G<br>$X_{38}$ = A, H, G or Y<br>$X_{39}$ = N or T | CDR-L1c |
| 41 | $X_{43}X_{44}X_{45}X_{46}X_{47}X_{48}X_{49}$<br>$X_{43}$ = W, Y, K or I<br>$X_{44}$ = A, T or V<br>$X_{45}$ = S or Y<br>$X_{46}$ = T, Q or N<br>$X_{47}$ = R, S or L<br>$X_{48}$ = H, I, F or E<br>$X_{49}$ = T or S | CDR-L2 |
| 42 | $X_{50}X_{51}X_{52}X_{53}X_{54}X_{55}PX_{56}T$<br>$X_{50}$ = Q or S<br>$X_{51}$ = Q or H<br>$X_{52}$ = S or Y<br>$X_{53}$ = S, N, T or R<br>$X_{54}$ = S, R, H or E<br>$X_{55}$ = Y, W, V or L<br>$X_{56}$ = L or Y | CDR-L3 |
| 43 | KASQDVGTAVA | 5E10-CDR-L1 |
| 44 | WASTRHT | 5E10-CDR-L2 |
| 45 | QQYSSYPLT | 5E10-CDR-L3 |
| 46 | RASQSISNNLH | 10D11-CDR-L1 |
| 47 | YTYQSIS | 10D11-CDR-L2 |
| 48 | QQSNRWPLT | 10D11-CDR-L3 |
| 49 | RSSQNLVHSNGNTYFH | 14G8-CDR-L1 |
| 50 | KVSNRFS | 14G8-CDR-L2 |
| 51 | SQSTHVPYT | 14G8-CDR-L3 |
| 52 | RASKSVSTSGYTYMH | 18B1-CDR-L1 |
| 53 | ITSNLES | 18B1-CDR-L2 |
| 54 | QHSRELPYT | 18B1-CDR-L3 |
| 55 | RSSQSLLHSNGNTYFH | 13C7-CDR-L1 |
| 50 | KVSNRFS | 13C7-CDR-L2 |
| 51 | SQSTHVPYT | 13C7-CDR-L3 |

In another embodiment, the present invention provides an antigen-binding polypeptide, which specifically binds to the LIGHT polypeptide comprising, consisting essentially of, or consisting of a humanized light chain variable region comprising a CDR-L1, CDR-L2 and CDR-L3 region. In certain embodiments the CDR-L1 region comprises, consists essentially of, or consists of the amino acid sequence selected from the group consisting of: SEQ ID NO:38; SEQ ID NO:39; SEQ ID NO:40; SEQ ID NO:43; SEQ ID NO:46; SEQ ID NO:49; SEQ ID NO:52; and SEQ ID NO:55. In certain embodiments the CDR-L2 region comprises, consists essentially of, or consists of the amino acid sequence selected from the group consisting of: SEQ ID NO:41; SEQ ID NO:44; SEQ ID NO:47; SEQ ID NO:50; and SEQ ID NO:53. In certain embodiments the CDR-L3 region comprises, consists essentially of, or consists of the amino acid sequence selected from the group consisting of: SEQ ID NO:42; SEQ ID NO:45; SEQ ID NO:48; SEQ ID NO:51; and SEQ ID NO:54.

In specific embodiments, the present invention includes an antigen-binding polypeptide, which specifically binds to the LIGHT polypeptide comprising, consisting essentially of, or consisting of a humanized light chain variable region comprising a CDR-L1 region comprising, consisting essentially of, or consisting of the amino acid sequence of SEQ ID NO:43, a CDR-L2 region comprising, consisting essentially of, or consisting of the amino acid sequence of SEQ ID NO:44 and a CDR-L3 region comprising, consisting essentially of, or consisting of the amino acid sequence of SEQ ID NO:45.

Antigen-binding polypeptides which specifically bind to the LIGHT polypeptide may comprise, consist essentially of, or consist of a humanized light chain variable region comprising any of the CDR-light chain regions disclosed herein.

In other embodiments of the invention, the antigen-binding polypeptides which specifically bind to the LIGHT polypeptide comprise, consist essentially of, or consist of a humanized heavy chain variable region and a humanized light chain variable region selected from the group consisting of:
  i. SEQ ID NO: 1 and SEQ ID NO:9;
  ii. SEQ ID NO:2 and SEQ ID NO:10;
  SEQ ID NO:3 and SEQ ID NO:11;
  iv. SEQ ID NO:4 and SEQ ID NO:12;
  v. SEQ ID NO:5 and SEQ ID NO:13;
  vi. SEQ ID NO:6 and SEQ ID NO:14;
  vii. SEQ ID NO:7 and SEQ ID NO:15;
  viii. SEQ ID NO:7 and SEQ ID NO:16
  ix. SEQ ID NO:8 and SEQ ID NO:17; and
  x. combinations thereof.

In other embodiments of the invention, the antigen-binding polypeptides which specifically bind to the LIGHT polypeptide comprise, consist essentially of, or consist of a humanized heavy chain variable region and a humanized light chain variable region comprising, consisting essentially of, or consisting of a CDR-H1, CDR-H2, CDR-H3, CDR-L1, CDR-L2 and CDR-L3 selected from the group consisting of:
  i. SEQ ID NOs:18, 19, 20 and SEQ ID NOs:38, 41, 42;
  ii. SEQ ID NOs:18, 19, 21 and SEQ ID NOs:39, 41, 42;
  iii. SEQ ID NOs:18, 19, 22 and SEQ ID NOs:40, 41, 42;
  iv. SEQ ID NOs:23, 24, 25 and SEQ ID NOs:43, 44, 45;
  v. SEQ ID NOs:26, 27, 28 and SEQ ID NOs:46, 47, 48;
  vi. SEQ ID NOs:29, 30, 31 and SEQ ID NOs:49, 50, 51;
  vii. SEQ ID NOs:32, 33, 34 and SEQ ID NOs:52, 53, 54;
  viii. SEQ ID NOs:35, 36, 37 and SEQ ID NOs:55, 50, 51; and
  ix. combinations thereof.

Any of the polypeptides described above may further include additional polypeptides, e.g., a signal peptide to direct secretion of the encoded polypeptide, antibody constant regions as described herein, or other heterologous polypeptides as described herein.

It will also be understood by one of ordinary skill in the art that antigen-binding polypeptides as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, or 95% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

Certain antigen-binding polypeptides of the present invention comprise, consist essentially of, or consist of an amino acid sequence derived from a human amino acid sequence. However, certain antigen-binding polypeptides may comprise one or more contiguous amino acids derived from another mammalian species. For example, an antigen-binding of the present invention may include a primate heavy chain portion, hinge portion, or antigen-binding region. In certain therapeutic applications, antigen-binding polypeptides, or antigen-binding fragments, variants, or analogs thereof are designed so as to not be immunogenic in the animal to which the antibody is administered.

In certain embodiments, an antigen-binding polypeptide comprises an amino acid sequence or one or more moieties not normally associated with an antibody. Exemplary modifications are described in more detail below. For example, a single-chain Fv antibody fragment of the invention may comprise a flexible linker sequence, or may be modified to add a functional moiety (e.g., PEG, a drug, a toxin, or a label).

An antigen-binding polypeptide of the invention may comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antigen-binding polypeptide, variant, or analog thereof, of the present invention, is derived from a non-immunoglobulin polypeptide of the same species, or an immunoglobulin or non-immunoglobulin polypeptide of a different species.

Antigen-binding polypeptides, variants, or derivatives thereof of the invention may further be fused to a heterologous polypeptide at the N- or C-terminus or chemically conjugated (including covalent and non-covalent conjugations)

to polypeptides or other compositions. For example, humanized LIGHT antigen-binding polypeptides, which specifically bind to the LIGHT polypeptide, may be fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387, which are incorporated herein by reference in their entireties.

Antigen-binding polypeptides, variants, or derivatives thereof of the invention include derivatives that are modified, i.e., by the covalent attachment of any type of molecule to the antibody such that covalent attachment does not prevent the antigen-binding polypeptide from binding to the LIGHT polypeptide. For example, but not by way of limitation, the antigen-binding polypeptides include antibodies that have been modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antigen-binding polypeptides may contain one or more non-classical amino acids.

Antigen-binding polypeptides, or variants, or derivatives thereof of the invention can be composed of amino acids joined to each other by peptide bonds or modified peptide bonds, i.e., peptide isosteres, and may contain amino acids other than the 20 gene-encoded amino acids. Antigen-binding polypeptides of the present invention may be modified by natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini, or on moieties such as carbohydrates. It will be appreciated that the same type of modification may be present in the same or varying degrees at several sites in a given antigen-binding polypeptide of the invention. Also, a given antigen-binding polypeptide may contain many types of modifications. Antigen-binding polypeptides may be branched, for example, as a result of ubiquitination, and they may be cyclic, with or without branching. Cyclic, branched, and branched cyclic antigen-binding polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W.H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The present invention also provides for fusion proteins comprising an antigen-binding polypeptide, variant, or derivative thereof, and a heterologous polypeptide. The heterologous polypeptide to which the antibody is fused may be useful for function or is useful for targeting to a specific area of the body during treatment. In one embodiment, a fusion protein of the invention comprises, consists essentially of, or consists of, a polypeptide having the amino acid sequence of any one or more of the variable heavy chain regions of an antigen-binding polypeptide of the invention or the amino acid sequence of any one or more of the variable light chain regions of an antigen-binding polypeptide of the invention or variants thereof, and a heterologous polypeptide sequence. In another embodiment, a fusion protein disclosed herein comprises, consists essentially of, or consists of a polypeptide having the amino acid sequence of any one, two, three of the variable heavy chain CDRs of an antigen-binding polypeptide, variants, or derivatives thereof described herein, or the amino acid sequence of any one, two, three of the variable light chain CDRs of a antigen-binding polypeptide, variants, or derivatives thereof described herein, and a heterologous polypeptide sequence.

In one embodiment, the fusion protein comprises a polypeptide having the amino acid sequence of a variable heavy CDR of an antigen-binding polypeptide of the present invention, or derivative, or variant thereof, and a heterologous polypeptide sequence, which fusion protein specifically binds to the LIGHT polypeptide. In another embodiment, a fusion protein comprises a polypeptide having the amino acid sequence of at least one variable heavy chain region of an antigen-binding polypeptide of the invention and the amino acid sequence of at least one variable light chain region of an antigen-binding polypeptide of the invention or derivatives or variants thereof, and a heterologous polypeptide sequence. Preferably, the variable heavy chain and variable light chain regions of the fusion protein correspond to a single source antibody (or scFv or Fab fragment) which specifically binds LIGHT. In yet another embodiment, a fusion protein disclosed herein comprises a polypeptide having the amino acid sequence of any one, two, three or more of the variable heavy chain CDRs of an antigen-binding polypeptide and the amino acid sequence of any one, two, three or more of the variable light chain CDRs of an antigen-binding polypeptide, or variants or derivatives thereof, and a heterologous polypeptide sequence. Preferably, two, three, four, five, six, or more of the variable heavy chain CDR(s) or variable light chain CDR(s) correspond to single source antibody (or scFv or Fab fragment) of the invention. Nucleic acid molecules encoding these fusion proteins are also encompassed by the invention.

Exemplary fusion proteins reported in the literature include fusions of the T-cell receptor (Gascoigne et al., *Proc. Natl. Acad. Sci. USA* 54:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349: 164-167 (1991)); CD44 (Aruffo et al., *Cell* (57:1303-1313 (1990)); CD28 and B7 (Linsley et al., *J. Exp. Med.* 773:721-730 (1991)); CTLA-4 (Lisley et al., *J. Exp. Med.* 174:561-569 (1991)); CD22 (Stamenkovic et al., *Cell* 66: 1133-1144 (1991)); TNF receptor (Ashkenazi et al., *Proc. Natl. Acad. Sci USA* 55:10535-10539 (1991); Lesslauer et al., *Eur. J. Immunol.* 27:2883-2886 (1991); and Peppel et al., *J. Exp. Med.*

774:1483-1489 (1991)); and IgE receptor a (Ridgway and Gorman, *J. Cell. Biol.* Vol. 115, Abstract No. 1448 (1991)).

Fusion proteins can be prepared using methods that are well known in the art (see e.g. U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

In certain embodiments the antigen-binding polypeptide of the present invention is a single-chain Fv molecule (scFv). Specifically certain scFv molecules of the present invention comprise, consist essentially of, or consist of a polypeptide with the formula selected from the group consisting of: $NH_2$-L-VH-X-VK-COOH and $NH_2$-L-VK-X-VH-COOH; wherein L is a leader sequence; VH is the humanized antibody heavy chain variable region; X is a linking polypeptide; and VK is the humanized antibody light chain variable region.

In other embodiments the antigen-binding polypeptide of the present invention is a single-chain Fv molecule (scFv) fused to human serum albumin (HSA) to create a scFV HSA fusion molecule which specifically binds to the LIGHT polypeptide. In specific embodiments, scFV is fused or linked to the N-terminus of HSA in the scFv HSA fusion molecule. In other embodiments, scFv is fused or linked to the C-terminus of HSA in the scFv HSA fusion molecule. In other embodiments the scFv HSA fusion molecule has a formula selected from the group consisting of: $NH_2$-L-VH-X-VK-HSA-COOH; $NH_2$-L-VK-X-VH-HSA-COOH, $NH_2$-HSA-VH-X-VK-COOH; and $NH_2$-HSA-VK-X-VH-COOH wherein L is a leader sequence; VH is the humanized antibody heavy chain variable region; X is a linking polypeptide; HSA is human serum albumin; and VK is the humanized antibody light chain variable region.

In certain embodiments the antigen-binding polypeptide of the present invention is a Fab fragment. In other embodiments the antigen-binding polypeptide of the present invention is Fab fragment fused or linked to human serum albumin (HSA) to create an Fab HSA fusion molecule which specifically binds to the LIGHT polypeptide. In specific embodiments, the heavy chain portion of the Fab fragment is fused or linked to the N- or C-terminus of HSA in the Fab HSA fusion molecule. In other embodiments, the light chain portion of the Fab fragment is fused or linked to the N- or C-terminus of HSA in the Fab HSA fusion molecule. In other embodiments the Fab HSA fusion molecule has a formula selected from the group consisting of: $NH_2$-VH-CH1-HSA-COOH; $NH_2$-HSA-VH-CH1-COOH, $NH_2$-VK-CK-HSA-COOH; and $NH_2$-HSA-VK-CK-COOH wherein VH is the humanized antibody heavy chain variable region; HSA is human serum albumin; VK is the humanized antibody light chain variable region; CH1 is the constant heavy chain domain 1; and CK is the constant light chain domain. The heavy or light chain portion of the Fab fragment or Fab HSA fusion molecule folds with its cognate counterpart (e.g. the humanize heavy chain variable region or the humanized light chain variable region of the antigen-binding polypeptides described herein) to produce the complete Fab-HSA or HSA-Fab fusion molecule.

In other embodiments, the antigen-binding polypeptides of the present invention may contain conservative amino acid substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Conjugation to a Therapeutic or Diagnostic Agent

In particular, antigen-binding polypeptides, variants, or derivatives thereof of the invention may be conjugated to therapeutic agents, prodrugs, peptides, proteins, enzymes, viruses, lipids, biological response modifiers, pharmaceutical agents, or PEG.

The antigen-binding polypeptides disclosed herein may be conjugated or fused to a therapeutic agent, which may include radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

Drugs may include those drugs that possess the pharmaceutical property selected from the group consisting of antimitotic, antikinase, alkylating, antimetabolite, antibiotic, alkaloid, antiangiogenic, apoptotic agents and combinations thereof. More specifically, these drugs are selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, anthracyclines, taxanes, and their analogs, and a combination thereof. The toxins encompassed by the present invention may be selected from the group consisting of ricin, abrin, alpha toxin, saporin, ribonuclease (RNase), e.g., onconase, DNase I, Staphylococcal enterotoxin-A, pokeweed antiviral protein, gelonin, diphtherin toxin, *Pseudomonas* exotoxin, and *Pseudomonas* endotoxin.

Immunomodulators may be selected from the group consisting of a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF)), interferon, such as interferons-alpha, -beta, or -gamma, and stem cell growth factor, such as designated "S1 factor". More specifically, immunomodulators may include IL-1, IL-2, IL-3, IL-6, IL-10, IL-12, IL-18, IL-21 interferon-gamma, TNF-alpha or a combination thereof.

In certain embodiments, the antigen-binding polypeptides disclosed herein may further comprise a targeting moiety. Targeting moieties include a protein or a peptide which directs localization to a certain part of the body, for example, to specific areas of inflammation.

As discussed elsewhere herein, antigen-binding polypeptides or variants, or derivatives thereof of the invention may be fused to heterologous polypeptides to increase the in vivo half life of the polypeptides or for use in immunoassays using methods known in the art. For example, in one embodiment, PEG can be conjugated to the LIGHT antibodies of the invention to increase their half-life in vivo. Leong, S. R., et al., *Cytokine* 16:106 (2001); Adv. in *Drug Deliv. Rev.* 54:531 (2002); or Weir et al., *Biochem. Soc. Transactions* 30:512 (2002).

Moreover, antigen-binding polypeptides, variants, or derivatives thereof of the invention can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci USA* 55:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:161 (1984)) and the "flag" tag (Brizzard et. al., Biotechniques 16(4): 730-735 (1994)).

Those skilled in the art will appreciate that conjugates may also be assembled using a variety of techniques depending on the selected agent to be conjugated. For example, conjugates with biotin are prepared e.g. by reacting a binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the antigen-binding polypeptides, fragments, variants, or derivatives thereof of the invention are prepared in an analogous manner.

The present invention further encompasses antigen-binding polypeptides, variants, or derivatives thereof of the invention conjugated to a diagnostic or therapeutic agent. The conjugated polypeptides can be used diagnostically to, for example, monitor the development or progression of a disease as part of a clinical testing procedure to, e.g., determine the efficacy of a given treatment and/or prevention regimen. Detection can be facilitated by coupling the antigen-binding, polypeptide fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, e.g., U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

An antigen-binding polypeptide, variant, or derivative thereof also can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

An antigen-binding polypeptide, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al., (eds.), Marcel Dekker, Inc., pp. 623-53 (1987); Thorpe, "Antibody Carriers Of Cytotoxic Agents In Cancer Therapy: A Review", in *Monoclonal Antibodies* '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

The antigen-binding polypeptides disclosed herein may also be conjugated or fused to a other diagnostic agents including, but not limited to, photoactive diagnostic agents or radiolabels having an energy between 60 and 4,000 keV, or a non-radioactive label. The radioactive label is preferably a gamma-, beta-, or positron-emitting isotope and is selected from the group consisting of $^{125}$I, $^{131}$I, $^{123}$I, $^{124}$I, $^{86}$Y, $^{186}$Re, $^{188}$Re, $^{62}$Cu, $^{64}$Cu, $^{111}$In, $^{67}$Ga, $^{68}$Ga, $^{99m}$Tc, $^{94m}$Tc, $^{18}$F, $^{11}$C, $^{13}$N, $^{15}$O, $^{76}$Br and combinations thereof. Diagnostic agents may also include contrast agents, for example, such as manganese, iron or gadolinium.

Polynucleotides Encoding Antigen-Binding Polypeptides

The present invention also provides for isolated polynucleotides or nucleic acid molecules encoding antigen-binding polypeptides, variants or derivatives thereof of the invention.

In one embodiment, polynucleotides of the present invention encode antigen-binding polypeptides which specifically bind the LIGHT polypeptide and comprise, consist essentially of, or consist of a humanized heavy chain variable region comprising, consisting essentially of, or consisting of an amino acid sequence selected from the group consisting of: SEQ ID NO:1; SEQ ID NO:2; SEQ ID NO:3; SEQ ID NO:4; SEQ ID NO:5; SEQ ID NO:6; SEQ ID NO:7; and SEQ ID NO:8. Specifically, certain polynucleotides of the present invention encode an antigen-binding polypeptide which specifically binds the LIGHT polypeptide and comprises, consists essentially of, or consists of a humanized heavy chain variable region comprising, consisting essentially of, or consisting of the amino acid sequence of SEQ ID NO:4.

In another embodiment, the polynucleotide of the present invention encodes a fully humanized LIGHT antibody comprising the heavy chain variable regions described herein with a complete heavy chain (i.e. constant regions).

In another embodiment, the present invention provides a polynucleotide encoding an antigen-binding polypeptide, which specifically binds to the LIGHT polypeptide comprising, consisting essentially of, or consisting of a humanized heavy chain variable region comprising a CDR-H1, CDR-H2 and CDR-H3 region. In certain embodiments the polynucleotide encodes a CDR-H1 region comprising, consisting essentially of, or consisting of the amino acid sequence selected from the group consisting of: SEQ ID NO:18; SEQ ID NO:23; SEQ ID NO:26; SEQ ID NO:29; SEQ ID NO:32; and SEQ ID NO:35. In certain embodiments the polynucleotide encodes a CDR-H2 region comprising, consisting essentially of, or consisting of the amino acid sequence selected from the group consisting of: SEQ ID NO:19; SEQ ID NO:24; SEQ ID NO:27; SEQ ID NO:30; SEQ ID NO:33; and SEQ ID NO:36. In certain embodiments the polynucleotide encodes a CDR-H3 region comprising, consisting essentially of, or consisting of the amino acid sequence selected from the group consisting of: SEQ ID NO:20; SEQ ID NO:21; SEQ ID NO:22; SEQ ID NO:25; SEQ ID NO:28; SEQ ID NO:31; SEQ ID NO:34; and SEQ ID NO:37.

In specific embodiments, the present invention includes a polynucleotide encoding an antigen-binding polypeptide, which specifically binds to the LIGHT polypeptide comprising, consisting essentially of, or consisting of a humanized heavy chain variable region comprising a CDR-H1 region comprising, consisting essentially of, or consisting of the amino acid sequence of SEQ ID NO:23, a CDR-H2 region comprising, consisting essentially of, or consisting of the amino acid sequence of SEQ ID NO:24 and a CDR-H3 region comprising, consisting essentially of, or consisting of the amino acid sequence of SEQ ID NO:25.

The present invention also includes a polynucleotide which encodes an antigen-binding polypeptide which specifically binds to the LIGHT polypeptide and comprises, consists essentially of, or consists of a humanized light chain variable region comprising, consisting essentially of, or consisting of an amino acid sequence selected from the group consisting of: SEQ ID NO:9; SEQ ID NO:10; SEQ ID NO:11; SEQ ID NO:12; SEQ ID NO:13; SEQ ID NO:14; SEQ ID NO:15; SEQ ID NO:16; and SEQ ID NO:17. Specifically, certain polynucleotides of the present invention encode an antigen-binding polypeptide which specifically binds the LIGHT polypeptide and comprises, consists essentially of, or consists of a humanized light chain variable region comprising, consisting essentially of, or consisting of the amino acid sequence of SEQ ID NO:12.

In another embodiment, the polynucleotide of the present invention encodes a fully humanized LIGHT antibody comprising the light chain variable regions described herein with a complete light chain (i.e. constant regions).

In another embodiment, the present invention provides a polynucleotide encoding an antigen-binding polypeptide, which specifically binds to the LIGHT polypeptide comprising, consisting essentially of, or consisting of a humanized light chain variable region comprising a CDR-L1, CDR-L2 and CDR-L3 region. In certain embodiments the polynucleotide encodes a CDR-L1 region comprising, consisting essentially of, or consisting of the amino acid sequence selected from the group consisting of: SEQ ID NO:38; SEQ ID NO:39; SEQ ID NO:40; SEQ ID NO:43; SEQ ID NO:46; SEQ ID NO:49; SEQ ID NO:52; and SEQ ID NO:55. In certain embodiments the CDR-L2 region comprises, consists essentially of, or consists of the amino acid sequence selected from the group consisting of: SEQ ID NO:41; SEQ ID NO:44; SEQ ID NO:47; SEQ ID NO:50; and SEQ ID NO:53. In certain embodiments the CDR-L3 region comprises, consists essentially of, or consists of the amino acid sequence selected from the group consisting of: SEQ ID NO:42; SEQ ID NO:45; SEQ ID NO:48; SEQ ID NO:51; and SEQ ID NO:54.

In specific embodiments, the present invention includes a polynucleotide encoding an antigen-binding polypeptide, which specifically binds to the LIGHT polypeptide comprising, consisting essentially of, or consisting of a humanized light chain variable region comprising a CDR-L1 region comprising, consisting essentially of, or consisting of the amino acid sequence of SEQ ID NO:43 a CDR-L2 region comprising, consisting essentially of, or consisting of the amino acid sequence of SEQ ID NO:44 and a CDR-L3 region comprising, consisting essentially of, or consisting of the amino acid sequence of SEQ ID NO:45.

In other embodiments of the invention, the polynucleotides of the invention encode antigen-binding polypeptides which specifically bind to the LIGHT polypeptide, comprising, consisting essentially of, or consisting of a humanized heavy chain variable region and a humanized light chain variable region selected from the group consisting of:
   i. SEQ ID NO:1 and SEQ ID NO:9;
   ii. SEQ ID NO:2 and SEQ ID NO:10;
   iii. SEQ ID NO:3 and SEQ ID NO:11;
   iv. SEQ ID NO:4 and SEQ ID NO:12;
   v. SEQ ID NO:5 and SEQ ID NO:13;
   vi. SEQ ID NO:6 and SEQ ID NO:14;
   vii. SEQ ID NO:7 and SEQ ID NO:15;
   viii. SEQ ID NO:7 and SEQ ID NO:16
   ix. SEQ ID NO:8 and SEQ ID NO:17; and
   x. combinations thereof.

Other embodiments of the invention include polynucleotides encoding antigen-binding polypeptides which specifically bind to the LIGHT polypeptide, comprising, consisting essentially of, or consisting of a humanized heavy chain variable region and a humanized light chain variable region comprising, consisting essentially of, or consisting of a CDR-H1, CDR-H2, CDR-H3, CDR-L1, CDR-L2 and CDR-L3 selected from the group consisting of:
   i. SEQ ID NOs:18, 19, 20 and SEQ ID NOs:38, 41, 42;
   ii. SEQ ID NOs:18, 19, 21 and SEQ ID NOs:39, 41, 42;
   iii. SEQ ID NOs:18, 19, 22 and SEQ ID NOs:40, 41, 42;
   iv. SEQ ID NOs:23, 24, 25 and SEQ ID NOs:43, 44, 45;
   v. SEQ ID NOs:26, 27, 28 and SEQ ID NOs:46, 47, 48;
   vi. SEQ ID NOs:29, 30, 31 and SEQ ID NOs:49, 50, 51;
   vii. SEQ ID NOs:32, 33, 34 and SEQ ID NOs:52, 53, 54;
   viii. SEQ ID NOs:35, 36, 37 and SEQ ID NOs:55, 50, 51; and
   ix. combinations thereof.

The polynucleotides of the present invention may encode the entire heavy and light chain variable regions of the antigen-binding polypeptides, variants or derivatives thereof on the same polynucleotide molecule or on separate polynucleotide molecules. Additionally, the polynucleotides of the present invention may encode portions of the heavy and light chain variable regions of the antigen-binding polypeptides, variants or derivatives thereof on the same polynucleotide molecule or on separate polynucleotide molecules.

Method of Making Antigen-Binding Polypeptides

Methods of making antibodies or antigen-binding polypeptides are well known in the art and described herein. In certain embodiments, both the variable and constant regions of the antigen-binding polypeptides of the present invention are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In certain embodiments, antigen-binding polypeptides, variants, or derivatives thereof of the invention will not elicit a deleterious immune response in the animal to be treated, e.g., in a human. In one embodiment, antigen-binding polypeptides, variants, or derivatives thereof of the invention are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci. USA* 57:6851-6855 (1984); Morrison et al., *Adv. Immunol.* 44:65-92 (1988); Verhoeyen et al., *Science* 239:1534-1536 (1988); Padlan, *Molec. Immun.* 25:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

The binding specificity of antigen-binding polypeptides of the present invention can be determined by in vitro assays such as immunoprecipitation, radioimmunoassay (RIA) or enzyme-linked immunoabsorbent assay (ELISA).

Alternatively, techniques described for the production of single chain antibodies (U.S. Pat. No. 4,694,778; Bird, *Science* 242:423-442 (1988); Huston et al., *Proc. Natl. Acad. Sci. USA* 55:5879-5883 (1988); and Ward et al., *Nature* 334:544-554 (1989)) can be adapted to produce single chain antibodies of the present invention. Single chain antibodies are formed by linking the heavy and light chain fragments of the Fv region via an amino acid bridge, resulting in a single chain antibody. Techniques for the assembly of functional Fv fragments in *E. coli* may also be used (Skerra et al., *Science* 242: 1038-1041 (1988)).

Antibody fragments, for example, Fab and F(ab')2 fragments, may be generated by known techniques including proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

Examples of techniques which can be used to produce single-chain Fvs (scFvs) and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596;

Padlan, *Molecular Immunology* 28(4/5):489-498 (1991); Studnicka et al., *Protein Engineering* 7(6):805-8H (1994); Roguska, et al., *Proc. Natl. Sci. USA* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98R 6654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

The generation of human or substantially human antigen-binding polypeptides of the present invention may also be generated in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 72:899-903 (1988). See also, U.S. Pat. No. 5,565,332, which is incorporated by reference in its entirety.)

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the antigen-binding polypeptides of the present invention, may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci. USA*: 851-855 (1984); Neuberger et al., *Nature* 372:604-608 (1984); Takeda et al., *Nature* 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies for use in the diagnostic and therapeutic methods disclosed herein can be produced by any method known in the art for the synthesis of antibodies, in particular, by chemical synthesis or preferably, by recombinant expression techniques as described herein.

Additionally, standard techniques known to those of skill in the art can be used to introduce mutations in the nucleotide sequence encoding a antigen-binding polypeptide of the present invention, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity (e.g., the ability to bind a LIGHT polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein, (e.g., ability to immunospecifically bind at least one epitope of a LIGHT polypeptide) can be determined using techniques described herein or by routinely modifying techniques known in the art.

Following manipulation of the isolated genetic material to provide antigen-binding polypeptides, variants, or derivatives thereof of the invention, the polynucleotides encoding the antigen polypeptides of the present invention are typically inserted in an expression vector for introduction into host cells that may be used to produce the desired quantity of antigen-binding polypeptides.

Recombinant expression of an antigen-binding polypeptide, derivative or variant thereof, e.g., a heavy or light chain of an antibody which binds to a target molecule described herein, e.g., LIGHT, requires construction of an expression vector containing a polynucleotide that encodes the antigen-binding polypeptide. Once a polynucleotide encoding an antigen-binding polypeptide or a heavy or light chain of an antigen-binding polypeptide, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) as discussed above. Any expression vector which is capable of eliciting expression in eukaryotic cells may be used in the present invention. Examples of suitable vectors include, but are not limited to plasmids pcDNA3, pHCMV/Zeo, pCR3.1, pEF I/His, pEMD/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels of immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 µg/cell/day. Other exemplary vector systems are disclosed e.g., in U.S. Pat. No. 6,413,777.

In other preferred embodiments the antigen-binding polypeptides, variants, or derivatives thereof of the invention may be expressed using polycistronic constructs such as those disclosed in United States Patent Application Publication No. 2003-0157641 A1, filed Nov. 18, 2002 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of antigen-binding polypeptides in eukaryotic host cells. Compatible IRES sequences are disclosed in U.S. Pat. No. 6,193,980 which is also incorporated herein. Those skilled in the art will appreciate that such expression systems may be used to effectively produce the full range of antigen-binding polypeptides disclosed in the instant application.

More generally, once the vector or DNA sequence encoding a monomeric subunit of the antigen-binding polypeptide has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" *Vectors*, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antigen-binding polypeptides. Such host-expression systems represent vehicles by which the coding sequences of interest may be produced and subsequently purified, but also represent cells which may, when transformed or transfected with the appropriate nucleotide coding sequences, express an antigen-binding polypeptide of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells, such as Chinese Hamster Ovary cells (CHO), in conjunction with a vector, such as one containing the major intermediate early gene promoter element from human cytomegalovirus, is an effective expression system for antibodies (Foecking et al., *Gene* 5:101 (1986); Cockett et al., *Bio/Technology* 8:2 (1990)).

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXBII (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/0 (mouse myeloma), P3x63-Ag3.653 (mouse myeloma), BFA-Ic IBPT (bovine endothelial cells), RAJI (human lymphocyte) and 293 (human kidney). Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antigen-binding polypeptides of the present invention.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci USA* 78:1527 (1981)); gpt, which confers resistance to mycophenolic acid (Mulligan & Berg, *Proc. Natl. Acad. Sci USA* 78:2072 (1981)); neo, which confers resistance to the aminoglycoside G-418 (Wu and Wu, *Biotherapy* 3:87-95 (1991)); and hygro, which confers resistance to hygromycin (Santerre et al., *Gene* 30:147 (1984)). Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression, A Laboratory Manual*, Stockton Press, NY (1990); and in Chapters 12 and 13, Dracopoli et al. (eds), *Current Prolocols in Human Genetics*, John Wiley & Sons, NY (1994); Colberre-Garapin et al., *J. Mol. Biol.* 150:1 (1981), which are incorporated by reference herein in their entireties.

The expression levels of an antigen-binding polypeptide can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Grouse et al., *Mol. Cell. Biol.* 3:257 (1983)).

Genes encoding antigen-binding polypeptides or variants, or derivatives thereof of the invention can also be expressed in non-mammalian cells such as bacteria or yeast or plant cells. Bacteria which readily take up nucleic acids include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2: 1791 (1983)), in which the antibody coding sequence may be ligated individually into the vector in frame with the lacZ coding region so that a fusion protein is produced; pIN vectors (Inouye & Inouye, *Nucleic Acids Res.* 73:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., Nature 252:39 (1979); Kingsman et al., *Gene* 7:141 (1979); Tschemper et al., *Gene* 10:157 (1980)) is commonly used. This plasmid already contains the trpl gene which provides a selection marker for a mutant strain of yeast lacking the ability to grow in tryptophan, for example ATCC No. 44076 or PEP4-1 (Jones, *Genetics* 85:12 (1977)). The presence of the trpl lesion as a characteristic of the yeast host cell genome then provides an effective environment for detecting transformation by growth in the absence of tryptophan.

In an insect system, *Autographa californica* nuclear polyhidrosis virus (AcNPV) is typically used as a vector to express foreign genes. The virus grows in *Spodoptera fru-*

*giperda* cells. The antibody coding sequence may be cloned individually into non-essential regions (for example the polyhedrin gene) of the virus and placed under control of an AcNPV promoter (for example the polyhedrin promoter).

Once an antigen-binding polypeptide of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002-0123057 A1 to Zauderer et al., filed Nov. 14, 2001.

Treatment and Diagnostic Methods

As described herein, the antigen-binding polypeptides, variants or derivatives of the present invention may be used in certain treatments and diagnostic methods associated with inflammatory, immune or malignant diseases or conditions. Specifically, certain antigen-binding polypeptides of the present invention may be antagonists of LIGHT activity. For example, certain antigen-binding polypeptide may be antagonists of LIGHT activity such as, T-cell stimulation, stimulation of proinflammatory cytokines, such as IFN-γ and IL-8, and stimulation of IL-17 production by CD3 and Th17 cells. Additionally, LIGHT antigen-binding polypolypeptides of the invention may interfere with LIGHT's ability to bind the LTβ receptor, the HVEM receptor and the decoy receptor 3/TR6, as well as other receptors to which LIGHT binds.

The present invention is further directed to antigen-binding polypeptide-based therapies which involve administering antigen-binding polypeptides of the invention to a patient such as an animal, a mammal, and a human for treating one or more of the disorders or conditions described herein. Therapeutic compounds of the invention include, but are not limited to, antigen-binding polypeptides of the invention (including variants and derivatives thereof as described herein) and nucleic acids or polynucleotides encoding antigen-binding polypeptides of the invention (including variants and derivatives thereof as described herein).

The antigen-binding polypeptides of the invention can be used to treat, inhibit or prevent diseases, disorders or conditions including, but not limited to, any one or more of the diseases, disorders, or conditions described herein such as, for example immune or inflammatory diseases, disorders, or conditions associated with such diseases or disorders (including, but not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis), systemic lupus erythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders), and immunodeficiencies or conditions associated with such diseases or disorders (including, but not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome), severe combined immunodeficiency, DiGeorge anomaly, thymichypoplasia, chronic mucocutaneous candidiasis, natural killer cell deficiency, idiopathic CD4+ T-lymphocytopenia, and immunodeficiency with predominant T-cell defect).

The antigen-binding polypeptides of the invention can also be used to treat, inhibit or prevent diseases, disorders or conditions including malignant diseases, disorders, or conditions associated with such diseases or disorder such as diseases associated with increased cell survival, or the inhibition of apoptosis, for example cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. Antigen binding polypeptides, variants or derivatives thereof of the present invention are used to inhibit growth, progression, and/or metastasis of cancers, in particular those listed above or in the paragraph that follows.

Additional diseases or conditions associated with increased cell survival, that may be treated, prevented, diagnosed and/or prognosed with the antigen-binding polypeptides or variants, or derivatives thereof of the invention include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Diseases associated with increased apoptosis, that may be treated, prevented, diagnosed and/or prognosed with the antigen-binding polypeptides or variants, or derivatives thereof of the invention include, but are not limited to, AIDS; neurodegenerative disorders (such as Alzheimer's disease, Parkinson's disease, amyotrophic lateral sclerosis, retinitis pigmentosa, cerebellar degeneration and brain tumor or prior associated disease); autoimmune disorders (such as, multiple sclerosis, Sjogren's syndrome, Grave's disease Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis) myelodysplastic syndromes (such as aplastic anemia), graft vs. host disease (acute and/or chronic), ischemic injury (such as that caused by myocardial infarction, stroke and reperfusion injury), liver injury or disease (e.g., hepatitis related liver injury, cirrhosis, ischemia/reperfusion injury, cholestosis (bile duct injury) and liver cancer); toxin-induced liver disease (such as that caused by alcohol), septic shock, ulcerative colitis, cachexia and anorexia.

Specific examples of diseases, disorders or conditions in which antigen-binding polypeptides of the present invention would be beneficial in a treatment or diagnostic methods include, but are not limited to, autoimmune disease, inflammatory bowel disease (IBD); chronic obstructive pulmonary disease (COPD); arthritis; rheumatoid arthritis; multiple sclerosis; transplant rejection; graft versus host disease (GVHD); central nervous system injury; Th1-mediated intestinal diseases; Crohn's disease; psoriasis; leukemia; lymphoma; chronic lymphocytic leukemia; atherosclerosis; lung carcinoma; colon carcinoma; and hepatitis.

A specific dosage and treatment regimen for any particular patient will depend upon a variety of factors, including the particular antigen-binding polypeptide, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antigen-binding polypeptides, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the invention may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the invention locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the antigen-binding polypeptide or composition can be delivered in a vesicle, in particular a liposome (see Langer, 1990, *Science* 249:1527-1533; Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid.)

In yet another embodiment, the antigen-binding polypeptide or composition can be delivered in a controlled release system. In one embodiment, a pump may be used (see Sefton, 1987, CRC *Crit. Ref. Biomed. Eng.* 14:201; Buchwald et al., 1980, Surgery 88:507; Saudek et al., 1989, *N. Engl. J. Med.* 321:574). In another embodiment, polymeric materials can be used (see *Medical Applications of Controlled Release*, Langer and Wise (eds.), CRC Pres., Boca Raton, Fla. (1974);

*Controlled Drug Bioavailability, Drug Product Design and Performance*, Smolen and Ball (eds.), Wiley, New York (1984); Ranger and Peppas, J., 1983, *Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled release system can be placed in proximity of the therapeutic target, i.e., the brain, thus requiring only a fraction of the systemic dose (see, e.g., Goodson, in *Medical Applications of Controlled Release*, supra, vol. 2, pp. 115-138 (1984)). Other controlled release systems are discussed in the review by Langer (1990, Science 249:1527-1533).

In a specific embodiment where the composition of the invention comprises a nucleic acid or polynucletide encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868), etc. Alternatively, a nucleic acid can be introduced intracellularly and incorporated within host cell DNA for expression, by homologous recombination.

The amount of the antigen-binding polypeptide of the invention which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present invention is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

In the treatment of rheumatoid arthritis, modes of administration of antigen-binding polypeptides of the present invention include, intradermal, subcutaneous and intra-articular injection and infusion. Antigen-binding polypeptides administered intra-articularly or intra-dermally per dose will be in the range of about 0.1 mg/kg to about 100 mg/kg of patient body weight.

The compositions of the invention may be administered alone or in combination with other therapeutic agents (e.g., a costimulatory molecule). Therapeutic agents that may be administered in combination with the compositions of the invention, include but are not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second. Thus, in effect, the therapeutic agents may be administered to individuals either at the same time or at different times. In most instances when the therapeutic agents are administered to individuals at different times, they will generally be administered in a manner such that the therapeutic effects of these agents overlap for a period of time. One of ordinary skill in the art would know how to use the antigen-binding polypeptides of the present invention for diagnostic, monitoring or therapeutic purposes.

The methods for treating an inflammatory, immune or malignant disease, condition or disorder comprising administration of an antigen-binding polypeptide, variant, or derivative thereof of the invention are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the invention, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Compositions

Various delivery systems are known and can be used to administer an antigen-binding polypeptide of the invention or a polynucleotide encoding an antigen-binding polypeptide of the invention, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432), construction of a nucleic acid as part of a retroviral or other vector, etc.

In a further embodiment, the compositions of the invention are administered in combination with an antiviral agent, antibacterial or antibiotic agent or antifungal agents. Any of these agents known in the art may be administered in the compositions of the current invention.

In an additional embodiment, the compositions of the invention are administered alone or in combination with an anti-inflammatory agent. Anti-inflammatory agents that may be administered with the compositions of the invention include, but are not limited to, glucocorticoids and the non-steroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the invention are administered in combination with other therapeutic or prophylactic regimens, such as, for example, radiation therapy.

The present invention also provides pharmaceutical compositions. Such compositions comprise a therapeutically effective amount of a antigen-binding polypeptide, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1

Method of Making Anti-LIGHT Antibodies Using Hybridoma Technology

BALB/c mice were immunized with recombinant LIGHT protein (extracellular domain fragment amino acids Leu Ile Glu to Phe Met Val of Genbank Accession No. AF036581). In a typical procedure, 10 mg of protein in 50 ml of complete Freund's adjuvant (Sigma, St. Louis, Mo.) was injected subcutaneously into mice. Two to four additional injections in incomplete Freund's adjuvant were given at 2 week intervals followed by a final boost in PBS. Alternatively, injections can be given in the foot pads. Three days after the final inoculation, mice were sacrificed and their spleens or poplietal lymph nodes were harvested. Lymphocytes were isolated for fusion from the spleens or lymph nodes. Lymphocytes were fused with P3X63Ag8.653 plasmacytoma cells at a ratio of 5:1 lymphocytes to plasmacytoma cell using PEG/DMSO (Sigma) as a fusion agent. After fusion, cells were resuspended in selective HAT media and seeded at 10⁶ cells per well in 96-well plates. The supernatants from hybridomas that survived HAT selection were screened by direct binding ELISA for the presence of LIGHT binding antibodies. Hybridomas secreting LIGHT binding antibodies were identified and their supernatants were further screened by ELISA for antibodies which inhibited binding of LIGHT to its 3 known receptors: HVEM, LTβR and DcR3. The hybridomas identified as positives for inhibition of LIGHT binding were then screened for inhibition of LIGHT mediated killing of HT-29 cells to identify LIGHT antagonistic antibodies.

Figure 3:
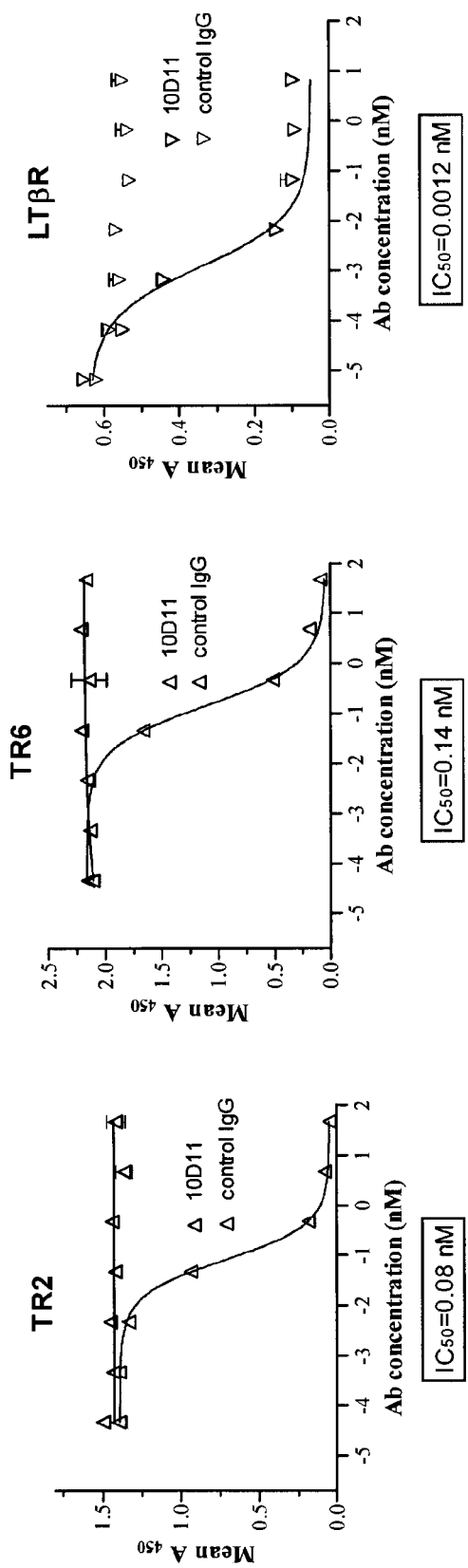
FIG. 3 demonstrates how the murine anti-LIGHT monoclonal antibody, 10D11, inhibits binding of LIGHT to its receptors. Fc-fusions of LIGHT receptors HVEM (TR2), decoy receptor 3 (TR6) and LTβR were coated on a 96-well plate using Protein A capture. LIGHT-biotin binding to the receptors was determined using streptavidin-HRP in the absence or presence of various concentrations of LIGHT antibodies.
Figure 4:
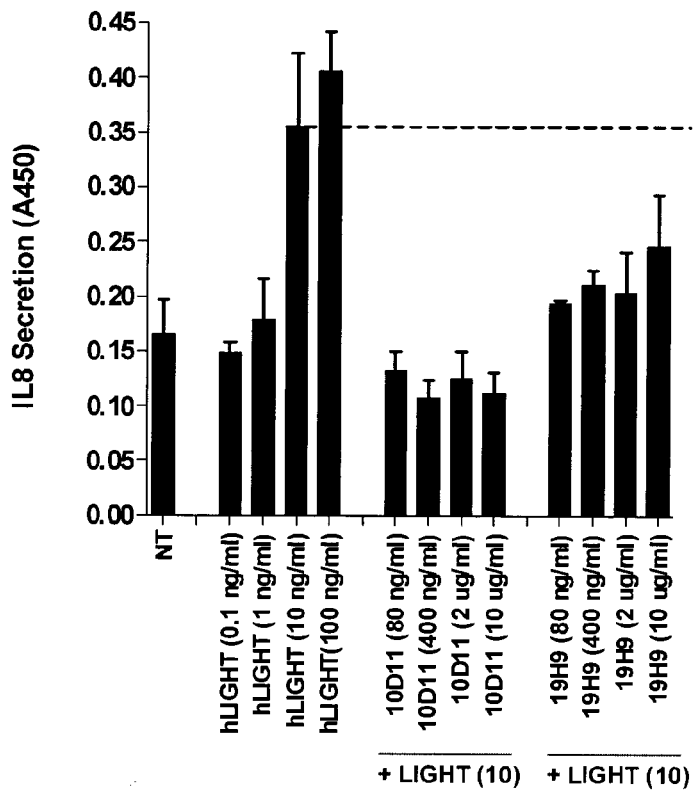
FIG. 4 demonstrates how the murine anti-LIGHT monoclonal antibody, 10D11, inhibits LIGHT-induced IL-8 production in endothelial cells. HUVEC cells were plated in 96-well plates. The confluent HUVEC cells were treated for 5 hours with LIGHT in the absence or presence of LIGHT antibody, 10D11, and a non-neutralizing control, 19H9. IL-8 secretion from HUVEC was determined by ELISA.
Figure 5A:
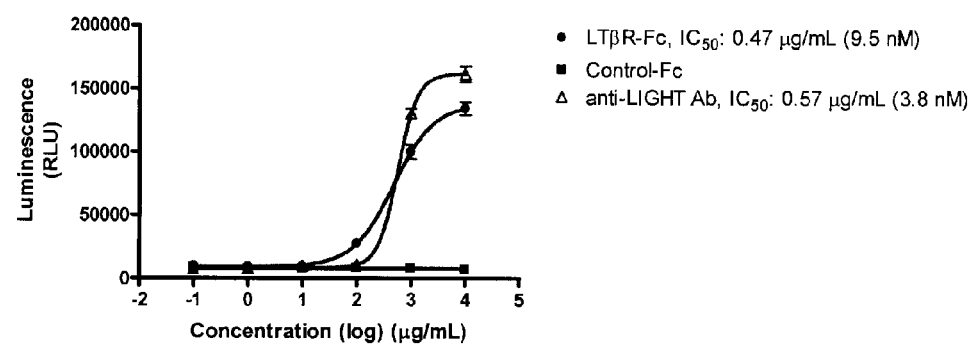
FIGS. 5A-C demonstrate how various anti-LIGHT murine monoclonal antibodies inhibit LIGHT-induced HT-29 cell apoptosis. LIGHT/TL5 induces cell death in the colon carcinoma cell line HT-29. An HT-29 cell viability assay (as described in Example 2) was used to determine the neutralizing activity of LIGHT antibodies. HT-29 cells were pretreated with IFN-γ for 6 hr at 37° C. Cells were then cultured with LIGHT in absence or presence of various concentrations of anti-LIGHT and control antibody or LTβR-Fc for 3 days. Cell viability was determined by using cell titer glo reagent (Promega).
Figure 5B:
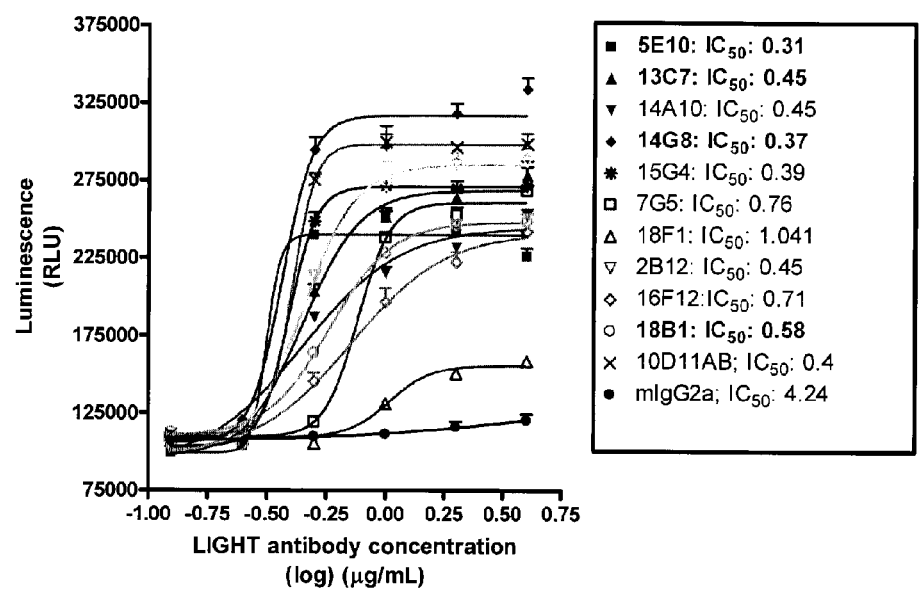
Figure 5C:
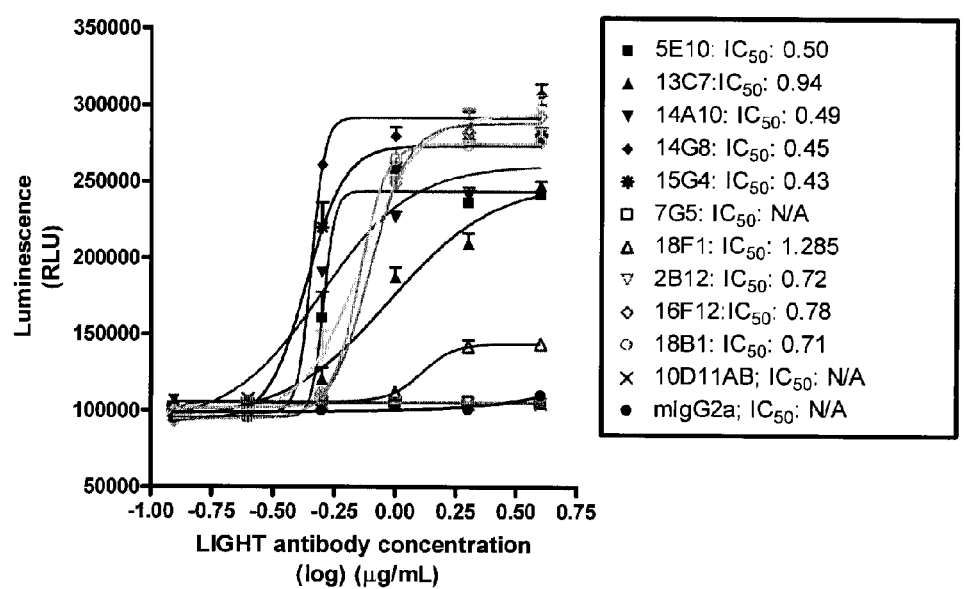
Figure 7:
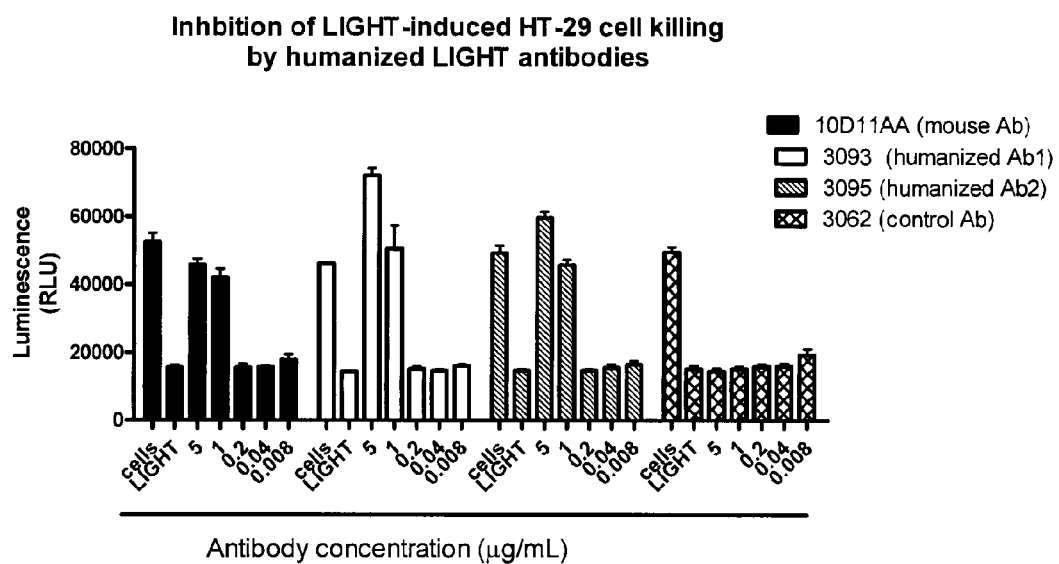
FIG. 7 illustrates the inhibition of LIGHT-induced HT-29 cell apoptosis by 2 different humanized LIGHT antibodies. HT-29 cells were pretreated with IFN-γ for 6 hr at 37° C. Cells were then cultured with LIGHT in the absence or presence of various concentrations of mouse and humanized LIGHT antibodies or control antibody for 3 days. Cell viability was determined by using cell titer glo reagent (Promega).
Figure 8:
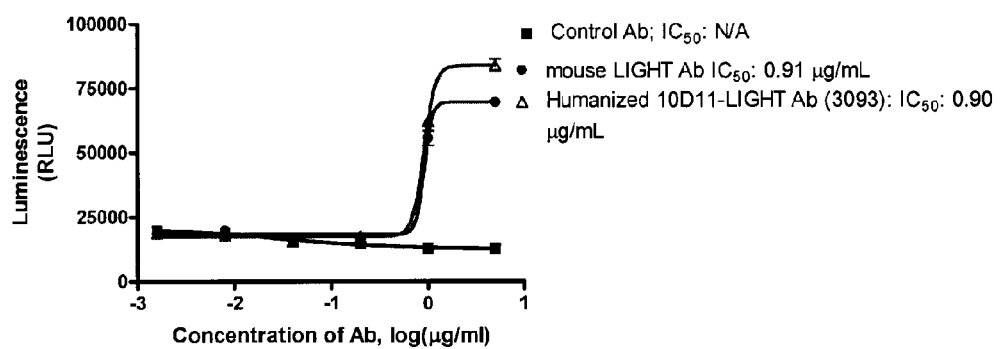
FIG. 8 illustrates the inhibition of LIGHT-induced HT-29 cell apoptosis by a fully humanized LIGHT antibody. HT-29 cells were pretreated with IFN-γ for 6 hr at 37° C. Cells were then cultured with LIGHT in absence or presence of various concentrations of mouse and humanized LIGHT antibodies or control antibody for 3 days. Cell viability was determined by using cell titer glo reagent (Promega).
Figure 9A:
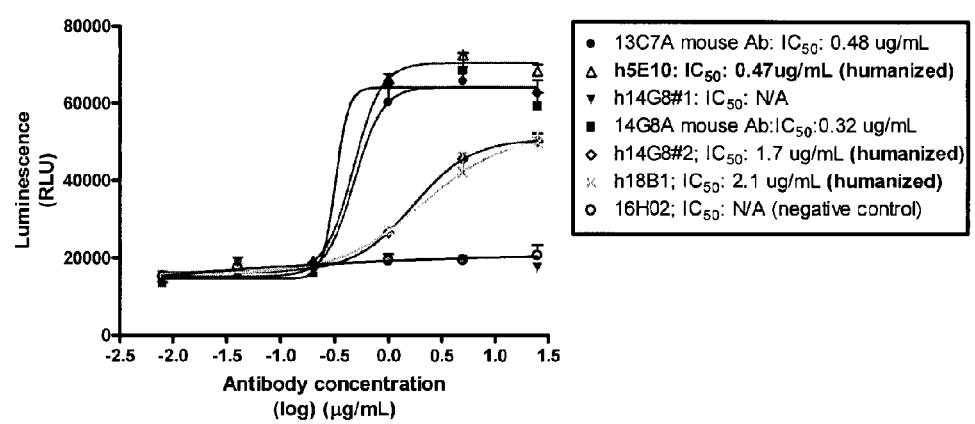
FIGS. 9A and B illustrate the inhibition of human (A) and cynomolgous (B) LIGHT-induced HT-29 cell apoptosis by humanized antibodies compared to control antibody 16H02. HT-29 cells were pretreated with IFN-γ for 6 hr at 37° C. Cells were then cultured with LIGHT in absence or presence of various concentrations of mouse and humanized LIGHT antibodies or control antibody for 3 days. Cell viability was determined by using cell titer glo reagent (Promega).
Figure 9B:
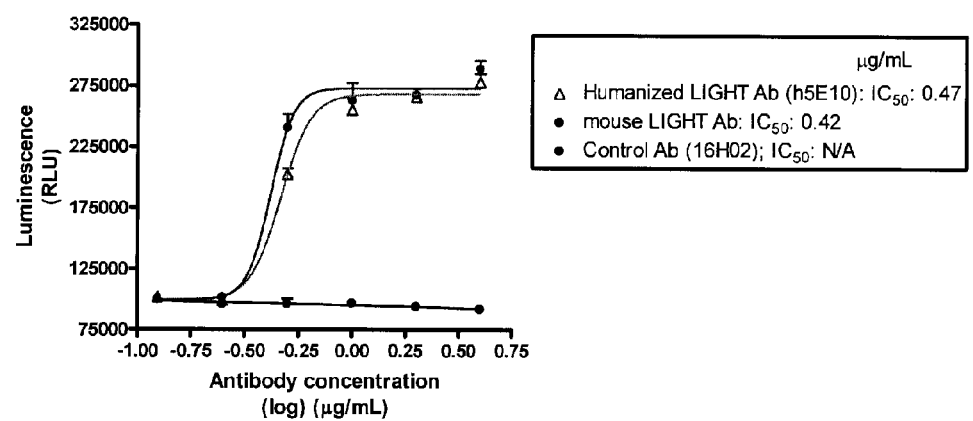

A panel of murine monoclonal antibodies were generated and lead murine antibodies (e.g., 10D11, 5E10, 13C7, 14G8 and 18B1) were selected for humanization based on binding assays and inhibition of LIGHT binding to HVEM, LTβR and decoy DcR3 receptors (FIG. 3). For example, binding data for the murine 10D11 antibody is indicated in Table 6 below.

TABLE 6

| Binding to LIGHT, | | Inhibition of LIGHT binding to: | | | Binding to cell surface |
|---|---|---|---|---|---|
| ELISA, EC-50 nM | BiaCore, Kd nM | HVEM IC-50 nM | LTbR IC-50 nM | DcR3 IC-50 nM | LIGHT MFC ratio* |
| 0.16 | 0.045 | 0.08 | 0.0012 | 0.14 | 13.1 |

*Ratio of MFC(Mean Fluorescence) on LIGHT transfected cells to MFC on vector control cells.

Cloning and Sequencing of Murine Anti-LIGHT VH and VK Domains from Hybridoma Cell Lines Hybridoma cells were pelleted, washed 3× with PBS and RNA extracted using Trizol reagent (Invitrogen, Cat. No. 15596-026) following the manufacturers protocol. Total RNA was converted to cDNA using a 5' RACE kit (Rapid Amplification of cDNA Ends, Invitrogen, Cat. No. 18374-058) following the manufacturers protocol. Briefly, RNA was ligated to random hexamer primer, Random N6, and 1$^{st}$ strand cDNA was generated using superscript II RNAase H negative reverse transcriptase. The cDNA was purified using a Glass-Max spin cartridge provided with the kit and then reacted with TdT (terminal deoxynucleotidyl transferase) in the presence of dCTP to append the cDNA with C basepairs at the 5' end. The dC-tailed cDNA was PCR amplified using an anchor primer specific for the dC tail and a gene specific primer that hybridizes to highly conserved DNA sequence in the mouse constant heavy 1 (CH1) for VH and constant kappa (CK) for VK. The resulting PCR product was analyzed by gel electrophoresis for correct size corresponding to intact VH or VK domains then purified and ligated into a TOPO TA vector (Invitrogen, Carlsbad, Calif., Cat. No. K4575-01) following the manufacturer's protocol. After transformation into bacteria, DNA was prepared from clones containing the correct size insert and the DNA sequence was determined using a Big Dye terminator sequencing reaction mix (Applied Biosystems, Part No. 4336699) and a 3700 ABI/Prism DNA analyzer following manufacturer's protocol.

Antibody Humanization Strategy

One goal in humanizing the anti-LIGHT antibodies was to obtain 70-100% humanized variable heavy (VH) and variable light (VK) domains that retain 90-100% of original binding affinity and specificity.

Humanization was performed by CDR grafting and structure based analysis and variable region resurfacing. (See Jones et al., NATURE (1986) May 29-Jun. 4; 321(6069):522-5; Roguska et al., PROTEIN ENGINEERING, 1996, 9(10):895-904; and Studnicka et al., Humanizing Mouse Antibody Frameworks While Preserving 3-D Structure. PROTEIN ENGINEERING, 1994, Vol. 7, pg 805). Primary antibody sequence and 3-D structure data was utilized to identify key framework residues required to maintain the binding affinity and specificity. The "Blast for Ig sequences" website sponsored by the NCBI was used to identify the closest match to the mouse VH and VK region used in the study. Human germline VH and VK genes were chosen as the best matches to the mouse sequence VH and VK sequences. Alternatively, sequences from the naturally expressed human antibody repertoire can be used as a template for humanization either alone or in combination with the closest matching human germline gene.

After aligning the variable heavy and variable light regions of the mouse anti-LIGHT antibody to the nearest human germlines or expressed repertoire of genes, the amino acid at every position was evaluated for potential influence on binding and immunogenicity. This information was used to assign a low, moderate, or high risk value for mutation at each position.

For the construction of humanized antibodies 10D11, 5E10, 14G8 and 18B1, for example, most positions, whether low, moderate, or high risk, were mutated simultaneously to produce the final humanized antibodies.

Humanizing Murine Anti-LIGHT Antibodies

Murine anti-LIGHT antibodies were identified based on binding data and sequence data generated as described above. The amino acid sequence of the VH and VK domains from these antibodies were aligned to human germline VH and VK domains using currently available public databases (i.e., BLAST for IgG at the NCBI and V-base at the MRC). At those positions in the framework where the mouse sequence differed from the human germline, an iterative process was used to convert or mutate the mouse framework so that it matched the corresponding human germline framework. In the event binding affinity is lost due to specific framework mutations, certain CDR amino acid residues for both the VH and VK may be mutated by replacement with tyrosine or other appropriate amino acids (i.e., affinity matured) to compensate for these losses. Affinity matured and humanized mouse VH and VK domains may be generated by a polymerase chain reaction process using a panel of overlapping synthetic DNA oligonucleotides. The amino acid sequences of variable heavy chain and variable light chain domains of mouse anti-LIGHT monoclonal antibodies which were humanized as described herein are shown below in Tables 7 and 8. The CDR portions of the variable domains are underlined.

TABLE 7

Amino Acid Sequence of Heavy Chain Variable Domains of Murine Anti-LIGHT Antibodies

| SEQ ID NO | Sequence | Name |
|---|---|---|
| 56 | QVQLQQSGPELVKPGASVKISCKASGYSFTSYYIHWVKQRPGQGLEWIGWIFPGSDITKYNEKFKGKATLTADTSSSTAYMQLSSLTSEDSTVYFCTREDYGISTYSAMDFWGQGTSVTVSS | m5E10 VH |
| 57 | EIQLQQSGPDLVKPGASVKVSCKASGYSFTDYYIYWVRQSHGKSLEWIGYIDPYNGGTKYNQKFKDTASLTVDKSSSTAFMHLNSLTSEDSAVYYCARTSGSSWFPYWGQGTLVTVSA | mD10D11 VH |
| 58 | QVQLQQSGAELVRPGTSVRVSCKASGYAFTNYLIEWIKQRPGQGLEWIGVINPGSGDTKYNENFKGKATLTADISSSTAYLQLSSLTSDDSAVYFCAGWNYWGQGTTLTVSS | m13C7 VH |

TABLE 7-continued

Amino Acid Sequence of Heavy Chain Variable
Domains of Murine Anti-LIGHT Antibodies

| SEQ ID NO | Sequence | Name |
|---|---|---|
| 59 | QVQLQQSGAELVRPGTSVQVSCKASGYSFTTYLIE WIKPQRGQGLEWIGVINPGTGETKYNENFRAKAIM TADKYSSTAYMQLSSLTADDSAVYFCARWDRWGQG TTLTVSS | m14G8 VH |
| 60 | QVQLQQPGAELVRPGTSVKLSCKASGYSFTTYWMN WVKQRPGQDLEWIGMIHPSDSESRLNQKFIDKATL SADKSSSTAYMLLNSPTSEDSAVYYCAFGNYVWAM DYWGQGTSVTVSS | m18B1 VH |

TABLE 8

Amino Acid Sequence of Light Chain Variable
Domains of Murine Anti-LIGHT Antibodies

| SEQ ID NO | Sequence | Name |
|---|---|---|
| 61 | DIVMTQSHKFMSTSVGDRVSITCKASQDVGTAVA WYQQKPGQSPKLLIYWASTRHTGVPDRFTGSGSG PDFTLTISNVQSEDLADYFCQQYSSYPLTFGSGT KLEIKR | m5E10 VK |
| 62 | DIVLTQSPATLSVTPGDSVSLSCRASQSISNNLH WYQQKSHESPRLLIKYTYQSISGIPSRFSGSGSG TDFTLTINSVETEDFGMYFCQQSNRWPLTFGAGT KLELKR | m10D11 VK |
| 63 | DVVMTQTPLSLPVSLGDQASISCRSSQSLLHSNG NTYFHWYLQKPGQSPELLIYKVSNRFSGVPDRFS GSGSGTDFTLKISRVEAEDLGVYFCSQSTHVPYT FGGGTKLEIKR | m13C7 VK |
| 64 | DVVMTQAPLSLPVSLGDQVSISCRSSQNLVHSNG NTYFHWYLQKPGQSPELLIYKVSNRFSGVPDRFS GSGSGTDFTLKISRVEAEDLGVYFCSQSTHVPYT FGGGTKLEIKR | m14G8 VK |
| 65 | DIVLTQSPASLVVSLGQRATISCRASKSVSTSGY TYMHWYQQKPGQPPKLLIYITSNLESGVPARFSG SGSGTDFTLNIHPVEEEDAATYYCQHSRELPYTF GGGTKLEIKR | m18B1 VK |

As part of the synthetic gene design process a codon optimization strategy was used. The triplet code for each amino acid that is preferentially utilized by mammalian cells for gene expression was incorporated at each position of the VH and VK. The synthetic VH and VK domains were then cloned into specialized mammalian expression vectors which allow for the expression of the corresponding VH and VK domains in the context of a fully human IgG1, G4 or Kappa antibody backbones. Small-scale production of the humanized antibodies were achieved by co-tranfection of an IgG1 or G4 construct with the Kappa construct into 293F cells with lipofectamine (Invitrogen, Carlsbad, Calif.) following the manufacture's protocol. Supernatants from the transient transfections were passed through Protein A or G resin and the IgG was purified to homogeneity for testing in cell based assays.

The amino acid sequences of variable heavy chain and variable light chain domains of exemplary humanized mouse anti-LIGHT monoclonal antibody prepared as described herein have been described previously in Tables 2 and 4.

Example 2

This example describes an assay protocol to measure inhibition of LIGHT-induced killing of HT-29 cells and is based on the activity of LIGHT to induce apoptosis in HT-29 cells. HT-29 cells were detached by trypsinization and washed twice with RPMI 10% FBS medium and resuspended at $1\times10^6$ cells/mL in RPMI 1% FBS medium. Cells were pre-treated with 100 ng/mL IFN-γ at 37° C. for 6 hours. The various concentrations of (4×) 5-fold serially diluted LIGHT antibody, LTβR-Fc and control-Fc were prepared starting at 40 g/mL. 25 μL of 4× reagents were transferred to 96-well plate in triplicate and 25 μL of 400 ng/mL (4×) LIGHT was added and incubated for 15 minutes at room temperature. Human LIGHT as well as cynomolgus LIGHT were used in separate experiments. See, e.g., FIGS. 9 A and B. 50 μL of $1\times10^6$/mL HT-29 cells (pre-incubated with IFN-γ) were added and cultured for 72 hr in a cell culture incubator. Cell viability was determined by adding 100 μL of cell titer glo reagent (Promega). The luminescence was read by Victor$^2$ fluorometer (Perkin-Elmer, Waltham, Mass.). Results from the use of this assay with various anti-LIGHT antibodies are shown in FIGS. 5A-C, 9A and 9B.

Example 3

Figure 10A:
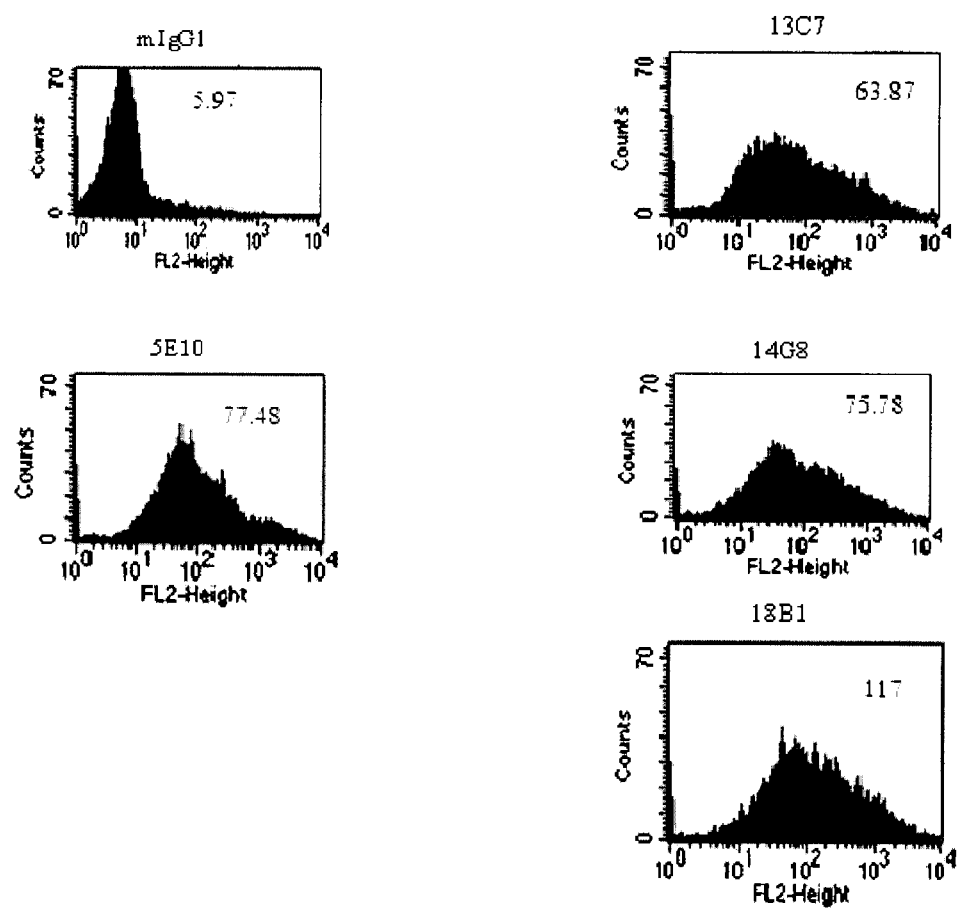
FIGS. 10A and B illustrate the binding of LIGHT antibodies to activated T-cells. Th1, Th2 and Th17 cells were generated from peripheral blood lymphocytes (PBL) isolated from blood by ficoll density gradient centrifugation. Th1 and Th17 cells were generated as described earlier (FIG. 1). Th2 cells were generated by culturing PBL with 2 µg/mL PHA plus IL-4 and anti-IFN-α antibody for 3 days. After 3 days, cells were maintained with 5 ng/mL IL-12. Cells were activated with Phorbol 12-myristate 13-acetate (PMA) and Ionomycin for 24 hr to induce expression of LIGHT. LIGHT antibody binding to activated T-cells was determined by flow cytometry using goat anti-mouse couple antibody conjugated to PE.
Figure 10B:
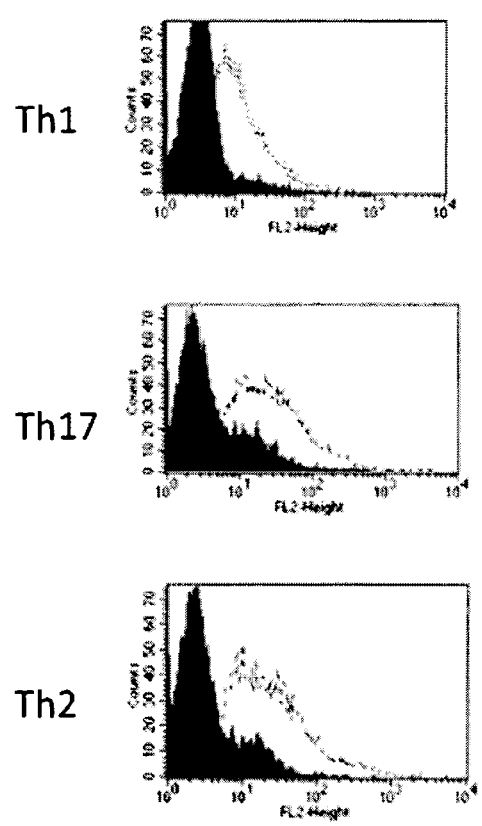
FIG. 10B illustrates binding of humanized 5E10 antibody to Th1, Th17 and Th2 activated T-cells compared to controls. Polarized T-cells were activated with PMA/Ionomycin for 24 hr. Biotin labeled LIGHT antibody or control antibody was incubated with cells for 40 minutes at room temperature. After washing twice with PBS, the antibody binding to LIGHT expressed on activated T-cells was determined by flow cytometry using strepavidin conjugated to PE. Dotted lines on figure indicates humanized LIGHT antibody binding. Solid fill indicates control antibody binding.

This example describes an assay protocol to determine LIGHT antibody binding to LIGHT expressed on surface of activated T-cells by Flow cytometry. Polarized Th1, Th2 and Th17 cells were activated with 50 ng/mL PMA and 0.5 μg/mL Ionomycin overnight at 37° C. One million activated T-cells were transferred to 5 mL FACS tubes and centrifuged at 1200 rpm for 5 minutes. The cellet pellet was resuspended in FACS staining buffer and incubated with anti-LIGHT or control antibodies at room temperature for 40 minutes. After washing twice with 2 mL PBS, the cells were incubated with PE-conjugated secondary reagents for 1 hour. The cells were washed 3 times with 2 mL PBS and resuspended in 0.5 mL PBS and analyzed by flow cytometry. Results from the use of this assay are shown in FIGS. 10A and 13.

The present invention is not to be limited in scope by the specific embodiments described which are intended as single illustrations of individual aspects of the invention, and any compositions or methods which are functionally equivalent are within the scope of this invention. It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

All publications and patent applications mentioned in this specification are herein incorporated by reference to the same extent as if each individual publication or patent application was specifically and individually indicated to be incorporated by reference

What is claimed is:

1. An antigen-binding polypeptide which specifically binds to the LIGHT polypeptide, wherein the polypeptide comprises a humanized heavy chain variable region comprising:
   (1) a CDR-H1 comprising the amino acid sequence SYYIH (SEQ ID NO:23),
   (2) a CDR-H2-comprising the amino acid sequence WIFPGSDITKYNEKFKG (SEQ ID NO:24), and
   (3) a CDR-H3 comprising the amino acid sequence EDYGISTYSAMDF (SEQ ID NO:25).

2. The antigen-binding polypeptide of claim 1, further comprising a humanized antibody light chain variable region comprising:
   (1) a CDR-L1 comprising the amino acid sequence KASQDVGTAVA (SEQ ID NO:43),
   (2) a CDR-L2 comprising the amino acid sequence WASTRHT (SEQ ID NO:44), and
   (3) a CDR-L3 comprising the amino acid sequence QQYSSYPLT (SEQ ID NO:45).

3. The antigen-binding polypeptide of claim 1, wherein the humanized antibody heavy chain variable region comprises the amino acid sequence:

(SEQ ID NO: 4)
QVQLVQSGAEVKKPGASVKVSCKASGYTFTSYYIHWVRQAPGQRLEWMGW

IFPGSDITKYNEKFKGRVTITRDTSASTAYMELSSLRSEDTAVYYCARED

YGISTYSAMDFWGQGTLVTVSS.

4. The antigen-binding polypeptide of claim 1, further comprising a humanized antibody light chain variable region that comprises the amino acid sequence:

(SEQ ID NO: 12)
DIQLTQSPSFLSASVGDRVTITCKASQDVGTAVAWYQQKPGKAPKLLIYW

ASTRHTGVPSRFSGSGSGTEFTLTISSLQPEDFATYYCQQYSSYPLTFGQ

GTKVEIKR.

5. The antigen-binding polypeptide of claim 1, wherein the antigen-binding polypeptide is selected from the group consisting of an antibody molecule, a Fab fragment, a Fab' fragment, a F(ab')$_2$ fragment, and an scFv molecule.

6. The polypeptide of claim 5, comprising:
   (a) a variable heavy chain region comprising the amino acid sequence:

(SEQ ID NO: 4)
QVQLVQSGAEVKKPGASVKVSCKASGYTFTSYYIHWVRQAPGQRLEWMGW

IFPGSDITKYNEKFKGRVTITRDTSASTAYMELSSLRSEDTAVYYCARED

YGISTYSAMDFWGQGTLVTVSS; and (b) a variable light chain region comprising the amino acid sequence:

(SEQ ID NO: 12)
DIQLTQSPSFLSASVGDRVTITCKASQDVGTAVAWYQQKPGKAPKLLIYW

ASTRHTGVPSRFSGSGSGTEFTLTISSLQPEDFATYYCQQYSSYPLTFGQ

GTKVEIKR.

7. The antigen-binding polypeptide of claim 6, wherein the antibody molecule comprises a human heavy chain constant region and a human light chain constant region.

8. The antigen-binding polypeptide of claim 6, wherein the antibody molecule is an IgG molecule.

9. The antigen-binding polypeptide of claim 5, wherein:
   (a) the antigen-binding polypeptide is an scFv molecule; or
   (b) the antigen-binding polypeptide is a scFv HSA fusion molecule; or
   (c) the antigen-binding polypeptide is a Fab HSA fusion molecule.

10. The antigen-binding polypeptide of claim 9, wherein:
   (a) the scFv molecule of claim 9(a) comprises a polypeptide with the formula selected from the group consisting of: (i) NH$_2$-L-VH-X-VK-COOH and (ii) NH$_2$-L-VK-X-VH-COOH; wherein L is a leader sequence; VH is the humanized antibody heavy chain variable region; X is a linking polypeptide; and VK is the humanized antibody light chain variable region;
   (b) the scFv portion of the scFv HSA fusion molecule of claim 9(b) is expressed at the N-terminus of HSA and the polypeptide has a formula selected from the group consisting of: (i) NH$_2$-L-VH-X-VK-HSA-COOH and (ii) NH$_2$-L-VK-X-VH-HSA-COOH, wherein L is a leader sequence; VH is the humanized antibody heavy chain variable region; X is a linking polypeptide; HSA is human serum albumin; and VK is the humanized antibody light chain variable region;
   (c) the scFv portion of the scFv HSA fusion molecule of claim 9(b) is expressed at the C-terminus of HSA and the polypeptide has a formula selected from the group consisting of: (i) NH$_2$-HSA-VH-X-VK-COOH and (ii) NH$_2$-HSA-VK-X-VH-COOH, wherein L is a leader sequence; VH is the humanized antibody heavy chain variable region; X is a linking polypeptide; HSA is human serum albumin and VK is the humanized antibody light chain variable region;
   (d) the antigen-binding polypeptide of claim 9(c), wherein the heavy chain portion of the Fab HSA fusion molecule is expressed at the N or C terminus of HSA and the polypeptide has a formula selected from the group consisting of: (i) NH$_2$-VH-CH1-HSA-COOH and (ii) NH$_2$-HSA-VH-CH1-COOH, wherein VH is the humanized antibody heavy chain variable region: CH1 is the constant heavy chain domain 1; and HSA is human serum albumin; or
   (e) the antigen-binding polypeptide of claim 9(c), wherein the light chain portion of the Fab HSA fusion molecule is expressed at the N or C terminus of HSA and the polypeptide has a formula selected from the group consisting of: (i) NH$_2$-VK-CK-HSA-COOH and (ii) NH$_2$-HSA-VK-CK-COOH, wherein VK is the humanized antibody light chain variable region; CK is the constant light chain domain; and HSA is human serum albumin.

11. The antigen-binding polypeptide of claim 1, conjugated to a therapeutic or diagnostic agent.

12. The antigen-binding polypeptide of claim 11, wherein:
   (a) the therapeutic agent is selected from the group consisting of a cytotoxic agent; a radioactive label; an immunomodulator; a hormone; an enzyme; an oligonucleotide; a photoactive therapeutic agent; and a combination thereof; or
   (b) the diagnostic agent is selected from the group consisting of a radioactive label; a photoactive diagnostic agent; an ultrasound-enhancing agent; and a non-radioactive label.

13. The antigen-binding polypeptide of claim 1, wherein the polypeptide binds to LIGHT with a K$_d$ of preferably at about $10^8 M^{-1}$ to about $10^{10} M^{-1}$.

14. A pharmaceutical composition comprising the antigen-binding polypeptide of claim 1 and a carrier.

15. The pharmaceutical composition of claim 14 further comprising an additional therapeutic or diagnostic agent.

16. An isolated polynucleotide encoding the antigen-binding polypeptide of claim 1.

17. An isolated polynucleotide comprising a promoter sequence operably linked to the polynucleotide of claim 16.

18. An isolated cell transformed with the polynucleotide of claim 16.

19. The antigen-binding polypeptide of claim 1, wherein the antigen-binding polypeptide comprises:
   (a) a humanized antibody heavy chain variable region comprising:
      (i) a CDR-H1 comprising the amino acid sequence SYYIH (SEQ ID NO:23),
      (ii) a CDR-H2 comprising the amino acid sequence WIFPGSDITKYNEKFKG (SEQ ID NO:24), and
      (iii) a CDR-H3 comprising the amino acid sequence EDYGISTYSAMDF (SEQ ID NO:25), and
   (b) a humanized antibody light chain variable region comprising:
      (i) a CDR-L1 comprising the amino acid sequence KASQDVGTAVA (SEQ ID NO:43),
      (ii) a CDR-L2 comprising the amino acid sequence WASTRHT (SEQ ID NO:44), and
      (iii) a CDR-L3 comprising the amino acid sequence QQYSSYPLT (SEQ ID NO:45).

* * * * *

SEQUENCE LISTING

<160> NUMBER OF SEQ ID NOS: 80

<210> SEQ ID NO 1
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (31)..(31)
<223> OTHER INFORMATION: /replace="Ser" or "Thr" or "Asn"
<220> FEATURE:
<221> NAME/KEY: misc_feature
<222> LOCATION: (31)..(31)
<223> OTHER INFORMATION: /note="Residue given in the sequence has no preference with respect to those in the annotations for said position"
<220> FEATURE:
<221> NAME/KEY: VARIANT
<222> LOCATION: (33)..(33)
<223> OTHER INFORMATION: /replace="Leu" or "Trp"
<220> FEATURE:
<221> NAME/KEY: VARIANT
<222> LOCATION: (34)..(34)
<223> OTHER INFORMATION: /replace="Met"
<220> FEATURE:
<221> NAME/KEY: VARIANT
<222> LOCATION: (35)..(35)
<223> OTHER INFORMATION: /replace="His" or "Glu" or "Asn"
<220> FEATURE:
<221> NAME/KEY: misc_feature
<222> LOCATION: (33)..(35)
<223> OTHER INFORMATION: /note="Residues given in the sequence have no preference with respect to those in the annotations for said positions"
<220> FEATURE:
<221> NAME/KEY: VARIANT
<222> LOCATION: (44)..(44)
<223> OTHER INFORMATION: /replace="Gly"
<220> FEATURE:
<221> NAME/KEY: misc_feature
<222> LOCATION: (44)..(44)
<223> OTHER INFORMATION: /note="Residue given in the sequence has no preference with respect to the annotation for said position"
<220> FEATURE:
<221> NAME/KEY: VARIANT
<222> LOCATION: (48)..(48)
<223> OTHER INFORMATION: /replace="Ile"
<220> FEATURE:
<221> NAME/KEY: misc_feature
<222> LOCATION: (48)..(48)
<223> OTHER INFORMATION: /note="Residue given in the sequence has no preference with respect to the annotation for said position"
<220> FEATURE:
<221> NAME/KEY: VARIANT
<222> LOCATION: (50)..(50)
<223> OTHER INFORMATION: /replace="Met" or "Val" or "Trp"
<220> FEATURE:
<221> NAME/KEY: misc_feature
<222> LOCATION: (50)..(50)
<223> OTHER INFORMATION: /note="Residue given in the sequence has no preference with respect to those in the annotations for said position"
<220> FEATURE:
<221> NAME/KEY: VARIANT
<222> LOCATION: (52)..(52)
<223> OTHER INFORMATION: /replace="Asn" or "His" or "Phe"
<220> FEATURE:
<221> NAME/KEY: misc_feature
<222> LOCATION: (52)..(52)
<223> OTHER INFORMATION: /note="Residue given in the sequence has no preference with respect to those in the annotations for said position"
<220> FEATURE:

```
<221> NAME/KEY: VARIANT
<222> LOCATION: (54)..(54)
<223> OTHER INFORMATION: /replace="Gly" or "Ser"
<220> FEATURE:
<221> NAME/KEY: VARIANT
<222> LOCATION: (55)..(55)
<223> OTHER INFORMATION: /replace="Ser" or "Thr" or "Asp"
<220> FEATURE:
<221> NAME/KEY: VARIANT
<222> LOCATION: (56)..(56)
<223> OTHER INFORMATION: /replace="Ser" or "Asp"
<220> FEATURE:
<221> NAME/KEY: VARIANT
<222> LOCATION: (57)..(57)
<223> OTHER INFORMATION: /replace="Asp" or "Glu" or "Ile"
<220> FEATURE:
<221> NAME/KEY: VARIANT
<222> LOCATION: (58)..(58)
<223> OTHER INFORMATION: /replace="Ser"
<220> FEATURE:
<221> NAME/KEY: VARIANT
<222> LOCATION: (59)..(59)
<223> OTHER INFORMATION: /replace="Arg"
<220> FEATURE:
<221> NAME/KEY: VARIANT
<222> LOCATION: (60)..(60)
<223> OTHER INFORMATION: /replace="Leu"
<220> FEATURE:
<221> NAME/KEY: misc_feature
<222> LOCATION: (54)..(60)
<223> OTHER INFORMATION: /note="Residues given in the sequence have no
      preference with respect to those in the annotations for said
      positions"
<220> FEATURE:
<221> NAME/KEY: VARIANT
<222> LOCATION: (62)..(62)
<223> OTHER INFORMATION: /replace="Glu"
<220> FEATURE:
<221> NAME/KEY: VARIANT
<222> LOCATION: (63)..(63)
<223> OTHER INFORMATION: /replace="Asn"
<220> FEATURE:
<221> NAME/KEY: misc_feature
<222> LOCATION: (62)..(63)
<223> OTHER INFORMATION: /note="Residues given in the sequence have no
      preference with respect to those in the annotations for said
      positions"
<220> FEATURE:
<221> NAME/KEY: VARIANT
<222> LOCATION: (65)..(65)
<223> OTHER INFORMATION: /replace="Ile" or "Arg"
<220> FEATURE:
<221> NAME/KEY: VARIANT
<222> LOCATION: (66)..(66)
<223> OTHER INFORMATION: /replace="Ala" or "Asp"
<220> FEATURE:
<221> NAME/KEY: VARIANT
<222> LOCATION: (67)..(67)
<223> OTHER INFORMATION: /replace="Arg"
<220> FEATURE:
<221> NAME/KEY: VARIANT
<222> LOCATION: (68)..(68)
<223> OTHER INFORMATION: /replace="Ala"
<220> FEATURE:
<221> NAME/KEY: misc_feature
<222> LOCATION: (65)..(68)
<223> OTHER INFORMATION: /note="Residues given in the sequence have no
      preference with respect to those in the annotations for said
      positions"
<220> FEATURE:
<221> NAME/KEY: VARIANT
<222> LOCATION: (70)..(70)
<223> OTHER INFORMATION: /replace="Leu" or "Ile"
<220> FEATURE:
<221> NAME/KEY: misc_feature
<222> LOCATION: (70)..(70)
<223> OTHER INFORMATION: /note="Residue given in the sequence has no
      preference with respect to those in the annotations for said
      position"
<220> FEATURE:
```

-continued

```
<221> NAME/KEY: VARIANT
<222> LOCATION: (72)..(72)
<223> OTHER INFORMATION: /replace="Arg"
<220> FEATURE:
<221> NAME/KEY: misc_feature
<222> LOCATION: (72)..(72)
<223> OTHER INFORMATION: /note="Residue given in the sequence has no
      preference with respect to the annotation for said position"
<220> FEATURE:
<221> NAME/KEY: VARIANT
<222> LOCATION: (74)..(74)
<223> OTHER INFORMATION: /replace="Lys"
<220> FEATURE:
<221> NAME/KEY: misc_feature
<222> LOCATION: (74)..(74)
<223> OTHER INFORMATION: /note="Residue given in the sequence has no
      preference with respect to the annotation for said position"
<220> FEATURE:
<221> NAME/KEY: VARIANT
<222> LOCATION: (76)..(76)
<223> OTHER INFORMATION: /replace="Ile" or "Thr"
<220> FEATURE:
<221> NAME/KEY: misc_feature
<222> LOCATION: (76)..(76)
<223> OTHER INFORMATION: /note="Residue given in the sequence has no
      preference with respect to those in the annotation for said
      position"
<220> FEATURE:
<221> NAME/KEY: VARIANT
<222> LOCATION: (79)..(79)
<223> OTHER INFORMATION: /replace="Ala"
<220> FEATURE:
<221> NAME/KEY: misc_feature
<222> LOCATION: (79)..(79)
<223> OTHER INFORMATION: /note="Residue given in the sequence has no
      preference with respect to the annotation for said position"
<220> FEATURE:
<221> NAME/KEY: VARIANT
<222> LOCATION: (85)..(85)
<223> OTHER INFORMATION: /replace="Ser"
<220> FEATURE:
<221> NAME/KEY: misc_feature
<222> LOCATION: (85)..(85)
<223> OTHER INFORMATION: /note="Residue given in the sequence has no
      preference with respect to the annotation for said position"
<220> FEATURE:
<221> NAME/KEY: VARIANT
<222> LOCATION: (89)..(89)
<223> OTHER INFORMATION: /replace="Glu"
<220> FEATURE:
<221> NAME/KEY: misc_feature
<222> LOCATION: (89)..(89)
<223> OTHER INFORMATION: /note="Residue given in the sequence has no
      preference with respect to the annotation for said position"
<220> FEATURE:
<221> NAME/KEY: VARIANT
<222> LOCATION: (100)..(100)
<223> OTHER INFORMATION: /replace="Asn"
<220> FEATURE:
<221> NAME/KEY: VARIANT
<222> LOCATION: (101)..(101)
<223> OTHER INFORMATION: /replace="Tyr"
<220> FEATURE:
<221> NAME/KEY: misc_feature
<222> LOCATION: (100)..(101)
<223> OTHER INFORMATION: /note="Residues given in the sequence have no
      preference with respect to those in the annotations for said
      position"

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Tyr Trp Val Arg Gln Ala Pro Gly Gln Arg Leu Glu Trp Met
        35                  40                  45
```

-continued

```
Gly Tyr Ile Asp Pro Tyr Asn Gly Gly Thr Lys Tyr Asn Gln Lys Phe
            50                  55                  60

Lys Gly Lys Val Thr Met Thr Val Asp Thr Ser Ala Ser Thr Val Tyr
 65                  70                  75                  80

Met Glu Leu Ser Arg Leu Arg Ser Asp Asp Thr Ala Val Tyr Tyr Cys
                 85                  90                  95

Ala Arg Trp Asp Arg Trp Gly Gln Gly Thr Leu Val Thr Val Ser Ser
                100                 105                 110

<210> SEQ ID NO 2
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (31)..(31)
<223> OTHER INFORMATION: /replace="Ser" or "Thr" or "Asn"
<220> FEATURE:
<221> NAME/KEY: misc_feature
<222> LOCATION: (31)..(31)
<223> OTHER INFORMATION: /note="Residue given in the sequence has no
      preference with respect to those in the annotations for said
      position"
<220> FEATURE:
<221> NAME/KEY: VARIANT
<222> LOCATION: (33)..(33)
<223> OTHER INFORMATION: /replace="Leu" or "Trp"
<220> FEATURE:
<221> NAME/KEY: VARIANT
<222> LOCATION: (34)..(34)
<223> OTHER INFORMATION: /replace="Met"
<220> FEATURE:
<221> NAME/KEY: VARIANT
<222> LOCATION: (35)..(35)
<223> OTHER INFORMATION: /replace="His" or "Glu" or "Asn"
<220> FEATURE:
<221> NAME/KEY: misc_feature
<222> LOCATION: (33)..(35)
<223> OTHER INFORMATION: /note="Residues given in the sequence have no
      preference with respect to those in the annotations for said
      position"
<220> FEATURE:
<221> NAME/KEY: VARIANT
<222> LOCATION: (44)..(44)
<223> OTHER INFORMATION: /replace="Gly"
<220> FEATURE:
<221> NAME/KEY: misc_feature
<222> LOCATION: (44)..(44)
<223> OTHER INFORMATION: /note="Residue given in the sequence has no
      preference with respect to the annotation for said position"
<220> FEATURE:
<221> NAME/KEY: VARIANT
<222> LOCATION: (48)..(48)
<223> OTHER INFORMATION: /replace="Ile"
<220> FEATURE:
<221> NAME/KEY: misc_feature
<222> LOCATION: (48)..(48)
<223> OTHER INFORMATION: /note="Residue given in the sequence has no
      preference with respect to the annotation for said position"
<220> FEATURE:
<221> NAME/KEY: VARIANT
<222> LOCATION: (50)..(50)
<223> OTHER INFORMATION: /replace="Met" or "Val" or "Trp"
<220> FEATURE:
<221> NAME/KEY: misc_feature
<222> LOCATION: (50)..(50)
<223> OTHER INFORMATION: /note="Residue given in the sequence has no
      preference with respect to those in the annotations for said
      position"
<220> FEATURE:
<221> NAME/KEY: VARIANT
<222> LOCATION: (52)..(52)
```

-continued

```
<223> OTHER INFORMATION: /replace="Asn" or "His" or "Phe"
<220> FEATURE:
<221> NAME/KEY: misc_feature
<222> LOCATION: (52)..(52)
<223> OTHER INFORMATION: /note="Residue given in the sequence has no
      preference with respect to those in the annotations for said
      position"
<220> FEATURE:
<221> NAME/KEY: VARIANT
<222> LOCATION: (54)..(54)
<223> OTHER INFORMATION: /replace="Gly" or "Ser"
<220> FEATURE:
<221> NAME/KEY: VARIANT
<222> LOCATION: (55)..(55)
<223> OTHER INFORMATION: /replace="Ser" or "Thr" or "Asp"
<220> FEATURE:
<221> NAME/KEY: VARIANT
<222> LOCATION: (56)..(56)
<223> OTHER INFORMATION: /replace="Ser" or "Asp"
<220> FEATURE:
<221> NAME/KEY: VARIANT
<222> LOCATION: (57)..(57)
<223> OTHER INFORMATION: /replace="Asp" or "Glu" or "Ile"
<220> FEATURE:
<221> NAME/KEY: VARIANT
<222> LOCATION: (58)..(58)
<223> OTHER INFORMATION: /replace="Ser"
<220> FEATURE:
<221> NAME/KEY: VARIANT
<222> LOCATION: (59)..(59)
<223> OTHER INFORMATION: /replace="Arg"
<220> FEATURE:
<221> NAME/KEY: VARIANT
<222> LOCATION: (60)..(60)
<223> OTHER INFORMATION: /replace="Leu"
<220> FEATURE:
<221> NAME/KEY: misc_feature
<222> LOCATION: (54)..(60)
<223> OTHER INFORMATION: /note="Residues given in the sequence have no
      preference with respect to those in the annotations for said
      position"
<220> FEATURE:
<221> NAME/KEY: VARIANT
<222> LOCATION: (62)..(62)
<223> OTHER INFORMATION: /replace="Glu"
<220> FEATURE:
<221> NAME/KEY: VARIANT
<222> LOCATION: (63)..(63)
<223> OTHER INFORMATION: /replace="Asn"
<220> FEATURE:
<221> NAME/KEY: misc_feature
<222> LOCATION: (62)..(63)
<223> OTHER INFORMATION: /note="Residues given in the sequence have no
      preference with respect to those in the annotations for said
      position"
<220> FEATURE:
<221> NAME/KEY: VARIANT
<222> LOCATION: (65)..(65)
<223> OTHER INFORMATION: /replace="Ile" or "Arg"
<220> FEATURE:
<221> NAME/KEY: VARIANT
<222> LOCATION: (66)..(66)
<223> OTHER INFORMATION: /replace="Ala" or "Asp"
<220> FEATURE:
<221> NAME/KEY: VARIANT
<222> LOCATION: (67)..(67)
<223> OTHER INFORMATION: /replace="Arg"
<220> FEATURE:
<221> NAME/KEY: VARIANT
<222> LOCATION: (68)..(68)
<223> OTHER INFORMATION: /replace="Ala"
<220> FEATURE:
<221> NAME/KEY: misc_feature
<222> LOCATION: (65)..(68)
<223> OTHER INFORMATION: /note="Residues given in the sequence have no
      preference with respect to those in the annotations for said
      position"
<220> FEATURE:
<221> NAME/KEY: VARIANT
<222> LOCATION: (70)..(70)
```

-continued

```
<223> OTHER INFORMATION: /replace="Leu" or "Ile"
<220> FEATURE:
<221> NAME/KEY: misc_feature
<222> LOCATION: (70)..(70)
<223> OTHER INFORMATION: /note="Residue given in the sequence has no
      preference with respect to those in the annotations for said
      position"
<220> FEATURE:
<221> NAME/KEY: VARIANT
<222> LOCATION: (72)..(72)
<223> OTHER INFORMATION: /replace="Arg"
<220> FEATURE:
<221> NAME/KEY: misc_feature
<222> LOCATION: (72)..(72)
<223> OTHER INFORMATION: /note="Residue given in the sequence has no
      preference with respect to the annotation for said position"
<220> FEATURE:
<221> NAME/KEY: VARIANT
<222> LOCATION: (74)..(74)
<223> OTHER INFORMATION: /replace="Lys"
<220> FEATURE:
<221> NAME/KEY: misc_feature
<222> LOCATION: (74)..(74)
<223> OTHER INFORMATION: /note="Residue given in the sequence has no
      preference with respect to the annotation for said position"
<220> FEATURE:
<221> NAME/KEY: VARIANT
<222> LOCATION: (76)..(76)
<223> OTHER INFORMATION: /replace="Ile" or "Thr"
<220> FEATURE:
<221> NAME/KEY: misc_feature
<222> LOCATION: (76)..(76)
<223> OTHER INFORMATION: /note="Residue given in the sequence has no
      preference with respect to those in the annotations for said
      position"
<220> FEATURE:
<221> NAME/KEY: VARIANT
<222> LOCATION: (79)..(79)
<223> OTHER INFORMATION: /replace="Ala"
<220> FEATURE:
<221> NAME/KEY: misc_feature
<222> LOCATION: (79)..(79)
<223> OTHER INFORMATION: /note="Residue given in the sequence has no
      preference with respect to the annotation for said position"
<220> FEATURE:
<221> NAME/KEY: VARIANT
<222> LOCATION: (85)..(85)
<223> OTHER INFORMATION: /replace="Ser"
<220> FEATURE:
<221> NAME/KEY: misc_feature
<222> LOCATION: (85)..(85)
<223> OTHER INFORMATION: /note="Residue given in the sequence has no
      preference with respect to the annotation for said position"
<220> FEATURE:
<221> NAME/KEY: VARIANT
<222> LOCATION: (89)..(89)
<223> OTHER INFORMATION: /replace="Glu"
<220> FEATURE:
<221> NAME/KEY: misc_feature
<222> LOCATION: (89)..(89)
<223> OTHER INFORMATION: /note="Residue given in the sequence has no
      preference with respect to the annotation for said position"
<220> FEATURE:
<221> NAME/KEY: VARIANT
<222> LOCATION: (99)..(99)
<223> OTHER INFORMATION: /replace="Thr" or "Gly"
<220> FEATURE:
<221> NAME/KEY: VARIANT
<222> LOCATION: (100)..(100)
<223> OTHER INFORMATION: /replace="Ser" or "Asn"
<220> FEATURE:
<221> NAME/KEY: VARIANT
<222> LOCATION: (101)..(101)
<223> OTHER INFORMATION: /replace="Gly"
<220> FEATURE:
<221> NAME/KEY: VARIANT
<222> LOCATION: (102)..(102)
<223> OTHER INFORMATION: /replace="Ser" or "Val"
<220> FEATURE:
<221> NAME/KEY: VARIANT
```

```
<222> LOCATION: (103)..(103)
<223> OTHER INFORMATION: /replace="Ser" or "Trp"
<220> FEATURE:
<221> NAME/KEY: VARIANT
<222> LOCATION: (104)..(104)
<223> OTHER INFORMATION: /replace="Trp" or "Ala"
<220> FEATURE:
<221> NAME/KEY: VARIANT
<222> LOCATION: (105)..(105)
<223> OTHER INFORMATION: /replace="Phe" or Met"
<220> FEATURE:
<221> NAME/KEY: VARIANT
<222> LOCATION: (106)..(106)
<223> OTHER INFORMATION: /replace="Pro" or "Asp"
<220> FEATURE:
<221> NAME/KEY: VARIANT
<222> LOCATION: (107)..(107)
<223> OTHER INFORMATION: /replace="Tyr"
<220> FEATURE:
<221> NAME/KEY: misc_feature
<222> LOCATION: (99)..(107)
<223> OTHER INFORMATION: /note="Residues given in the sequence have no
      preference with respect to those in the annotations for said
      position"

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Tyr Trp Val Arg Gln Ala Pro Gly Gln Arg Leu Glu Trp Met
        35                  40                  45

Gly Tyr Ile Asp Pro Tyr Asn Gly Gly Thr Lys Tyr Asn Gln Lys Phe
    50                  55                  60

Lys Gly Lys Val Thr Met Thr Val Asp Thr Ser Ala Ser Thr Val Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Gly Ile Ser Thr Tyr Ser Trp Gly Gln Gly Thr
            100                 105                 110

Leu Val Thr Val Ser Ser
        115

<210> SEQ ID NO 3
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (31)..(31)
<223> OTHER INFORMATION: /replace="Ser" or "Thr" or "Asn"
<220> FEATURE:
<221> NAME/KEY: misc_feature
<222> LOCATION: (31)..(31)
<223> OTHER INFORMATION: /note="Residue given in the sequence has no
      preference with respect to those in the annotations for said
      position"
<220> FEATURE:
<221> NAME/KEY: VARIANT
<222> LOCATION: (33)..(33)
<223> OTHER INFORMATION: /replace="Leu" or "Trp"
<220> FEATURE:
<221> NAME/KEY: VARIANT
<222> LOCATION: (34)..(34)
<223> OTHER INFORMATION: /replace="Met"
<220> FEATURE:
<221> NAME/KEY: VARIANT
```

-continued

```
<222> LOCATION: (35)..(35)
<223> OTHER INFORMATION: /replace="His" or "Glu" or "Asn"
<220> FEATURE:
<221> NAME/KEY: misc_feature
<222> LOCATION: (33)..(35)
<223> OTHER INFORMATION: /note="Residues given in the sequence have no
      preference with respect to those in the annotations for said
      position"
<220> FEATURE:
<221> NAME/KEY: VARIANT
<222> LOCATION: (44)..(44)
<223> OTHER INFORMATION: /replace="Gly"
<220> FEATURE:
<221> NAME/KEY: misc_feature
<222> LOCATION: (44)..(44)
<223> OTHER INFORMATION: /note="Residue given in the sequence has no
      preference with respect to the annotation for said position"
<220> FEATURE:
<221> NAME/KEY: VARIANT
<222> LOCATION: (48)..(48)
<223> OTHER INFORMATION: /replace="Ile"
<220> FEATURE:
<221> NAME/KEY: misc_feature
<222> LOCATION: (48)..(48)
<223> OTHER INFORMATION: /note="Residue given in the sequence has no
      preference with respect to the annotation for said position"
<220> FEATURE:
<221> NAME/KEY: VARIANT
<222> LOCATION: (50)..(50)
<223> OTHER INFORMATION: /replace="Mer" or "Val" or "Trp"
<220> FEATURE:
<221> NAME/KEY: misc_feature
<222> LOCATION: (50)..(50)
<223> OTHER INFORMATION: /note="Residue given in the sequence has no
      preference with respect to those in the annotations for said
      position"
<220> FEATURE:
<221> NAME/KEY: VARIANT
<222> LOCATION: (52)..(52)
<223> OTHER INFORMATION: /replace="Asn" or "His" or "Phe"
<220> FEATURE:
<221> NAME/KEY: misc_feature
<222> LOCATION: (52)..(52)
<223> OTHER INFORMATION: /note="Residue given in the sequence has no
      preference with respect to those in the annotations for said
      position"
<220> FEATURE:
<221> NAME/KEY: VARIANT
<222> LOCATION: (54)..(54)
<223> OTHER INFORMATION: /replace="Gly" or "Ser"
<220> FEATURE:
<221> NAME/KEY: VARIANT
<222> LOCATION: (55)..(55)
<223> OTHER INFORMATION: /replace="Ser" or "Thr" or "Asp"
<220> FEATURE:
<221> NAME/KEY: VARIANT
<222> LOCATION: (56)..(56)
<223> OTHER INFORMATION: /replace="Ser" or "Asp"
<220> FEATURE:
<221> NAME/KEY: VARIANT
<222> LOCATION: (57)..(57)
<223> OTHER INFORMATION: /replace="Asp" or "Glu" or "Ile"
<220> FEATURE:
<221> NAME/KEY: VARIANT
<222> LOCATION: (58)..(58)
<223> OTHER INFORMATION: /replace="Ser"
<220> FEATURE:
<221> NAME/KEY: VARIANT
<222> LOCATION: (59)..(59)
<223> OTHER INFORMATION: /replace="Arg"
<220> FEATURE:
<221> NAME/KEY: VARIANT
<222> LOCATION: (60)..(60)
<223> OTHER INFORMATION: /replace="Leu"
<220> FEATURE:
<221> NAME/KEY: misc_feature
<222> LOCATION: (54)..(60)
<223> OTHER INFORMATION: /note="Residues given in the sequence have no
      preference with respect to those in the annotations for said
      position"
```

-continued

```
<220> FEATURE:
<221> NAME/KEY: VARIANT
<222> LOCATION: (62)..(62)
<223> OTHER INFORMATION: /replace="Glu"
<220> FEATURE:
<221> NAME/KEY: VARIANT
<222> LOCATION: (63)..(63)
<223> OTHER INFORMATION: /replace="Asn"
<220> FEATURE:
<221> NAME/KEY: misc_feature
<222> LOCATION: (62)..(63)
<223> OTHER INFORMATION: /note="Residues given in the sequence have no
      preference with respect to those in the annotations for said
      position"
<220> FEATURE:
<221> NAME/KEY: VARIANT
<222> LOCATION: (65)..(65)
<223> OTHER INFORMATION: /replace="Ile" or "Arg"
<220> FEATURE:
<221> NAME/KEY: VARIANT
<222> LOCATION: (66)..(66)
<223> OTHER INFORMATION: /replace="Ala" or "Asp"
<220> FEATURE:
<221> NAME/KEY: VARIANT
<222> LOCATION: (67)..(67)
<223> OTHER INFORMATION: /replace="Arg"
<220> FEATURE:
<221> NAME/KEY: VARIANT
<222> LOCATION: (68)..(68)
<223> OTHER INFORMATION: /replace="Ala"
<220> FEATURE:
<221> NAME/KEY: misc_feature
<222> LOCATION: (65)..(68)
<223> OTHER INFORMATION: /note="Residues given in the sequence have no
      preference with respect to those in the annotations for said
      position"
<220> FEATURE:
<221> NAME/KEY: VARIANT
<222> LOCATION: (70)..(70)
<223> OTHER INFORMATION: /replace="Leu" or "Ile"
<220> FEATURE:
<221> NAME/KEY: misc_feature
<222> LOCATION: (70)..(70)
<223> OTHER INFORMATION: /note="Residue given in the sequence has no
      preference with respect to those in the annotations for said
      position"
<220> FEATURE:
<221> NAME/KEY: VARIANT
<222> LOCATION: (72)..(72)
<223> OTHER INFORMATION: /replace="Arg"
<220> FEATURE:
<221> NAME/KEY: misc_feature
<222> LOCATION: (72)..(72)
<223> OTHER INFORMATION: /note="Residue given in the sequence has no
      preference with respect to the annotation for said position"
<220> FEATURE:
<221> NAME/KEY: VARIANT
<222> LOCATION: (74)..(74)
<223> OTHER INFORMATION: /replace="Lys"
<220> FEATURE:
<221> NAME/KEY: misc_feature
<222> LOCATION: (74)..(74)
<223> OTHER INFORMATION: /note="Residue given in the sequence has no
      preference with respect to the annotation for said position"
<220> FEATURE:
<221> NAME/KEY: VARIANT
<222> LOCATION: (76)..(76)
<223> OTHER INFORMATION: /replace="Ile" or "Thr"
<220> FEATURE:
<221> NAME/KEY: misc_feature
<222> LOCATION: (76)..(76)
<223> OTHER INFORMATION: /note="Residue given in the sequence has no
      preference with respect to those in the annotations for said
      position"
<220> FEATURE:
<221> NAME/KEY: VARIANT
<222> LOCATION: (79)..(79)
<223> OTHER INFORMATION: /replace="Ala"
<220> FEATURE:
<221> NAME/KEY: misc_feature
```

```
<222> LOCATION: (79)..(79)
<223> OTHER INFORMATION: /note="Residue given in the sequence has no
      preference with respect to the annotation for said position"
<220> FEATURE:
<221> NAME/KEY: VARIANT
<222> LOCATION: (85)..(85)
<223> OTHER INFORMATION: /replace="Ser"
<220> FEATURE:
<221> NAME/KEY: misc_feature
<222> LOCATION: (85)..(85)
<223> OTHER INFORMATION: /note="Residue given in the sequence has no
      preference with respect to the annotation for said position"
<220> FEATURE:
<221> NAME/KEY: VARIANT
<222> LOCATION: (89)..(89)
<223> OTHER INFORMATION: /replace="Glu"
<220> FEATURE:
<221> NAME/KEY: misc_feature
<222> LOCATION: (89)..(89)
<223> OTHER INFORMATION: /note="Residue given in the sequence has no
      preference with respect to the annotation for said position"
<220> FEATURE:
<221> NAME/KEY: VARIANT
<222> LOCATION: (99)..(99)
<223> OTHER INFORMATION: /replace="Thr" or "Gly"
<220> FEATURE:
<221> NAME/KEY: VARIANT
<222> LOCATION: (100)..(100)
<223> OTHER INFORMATION: /replace="Ser" or "Asn"
<220> FEATURE:
<221> NAME/KEY: VARIANT
<222> LOCATION: (101)..(101)
<223> OTHER INFORMATION: /replace="Gly"
<220> FEATURE:
<221> NAME/KEY: VARIANT
<222> LOCATION: (102)..(102)
<223> OTHER INFORMATION: /replace="Ser" or "Val"
<220> FEATURE:
<221> NAME/KEY: VARIANT
<222> LOCATION: (103)..(103)
<223> OTHER INFORMATION: /replace="Ser" or "Trp"
<220> FEATURE:
<221> NAME/KEY: VARIANT
<222> LOCATION: (104)..(104)
<223> OTHER INFORMATION: /replace="Trp" or "Ala"
<220> FEATURE:
<221> NAME/KEY: VARIANT
<222> LOCATION: (105)..(105)
<223> OTHER INFORMATION: /replace="Phe" or Met"
<220> FEATURE:
<221> NAME/KEY: VARIANT
<222> LOCATION: (106)..(106)
<223> OTHER INFORMATION: /replace="Pro" or "Asp"
<220> FEATURE:
<221> NAME/KEY: VARIANT
<222> LOCATION: (107)..(107)
<223> OTHER INFORMATION: /replace="Tyr"
<220> FEATURE:
<221> NAME/KEY: misc_feature
<222> LOCATION: (99)..(107)
<223> OTHER INFORMATION: /note="Residues given in the sequence have no
      preference with respect to those in the annotations for said
      position"

<400> SEQUENCE: 3

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
                20                  25                  30

Tyr Ile Tyr Trp Val Arg Gln Ala Pro Gly Gln Arg Leu Glu Trp Met
            35                  40                  45

Gly Tyr Ile Asp Pro Tyr Asn Gly Gly Thr Lys Tyr Asn Gln Lys Phe
        50                  55                  60

Lys Gly Lys Val Thr Met Thr Val Asp Thr Ser Ala Ser Thr Val Tyr
65                  70                  75                  80
```

```
Met Glu Leu Ser Arg Leu Arg Ser Asp Asp Thr Ala Val Tyr Tyr Cys
                85                  90                  95

Ala Arg Glu Asp Tyr Gly Ile Ser Thr Tyr Ser Ala Met Asp Phe Trp
            100                 105                 110

Gly Gln Gly Thr Leu Val Thr Val Ser Ser
        115                 120

<210> SEQ ID NO 4
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Arg Leu Glu Trp Met
        35                  40                  45

Gly Trp Ile Phe Pro Gly Ser Asp Ile Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Gly Ile Ser Thr Tyr Ser Ala Met Asp Phe Trp
            100                 105                 110

Gly Gln Gly Thr Leu Val Thr Val Ser Ser
        115                 120

<210> SEQ ID NO 5
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Tyr Trp Val Arg Gln Ala Pro Gly Gln Gly Leu Glu Trp Ile
        35                  40                  45

Gly Tyr Ile Asp Pro Tyr Asn Gly Gly Thr Lys Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Ser Gly Ser Ser Trp Phe Pro Tyr Trp Gly Gln Gly Thr
            100                 105                 110

Leu Val Thr Val Ser Ser
```

<210> SEQ ID NO 6
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Tyr Trp Val Arg Gln Ala Pro Gly Gln Gly Leu Glu Trp Ile
        35                  40                  45

Gly Tyr Ile Asp Pro Tyr Asn Gly Gly Thr Lys Tyr Asn Gln Lys Phe
    50                  55                  60

Lys Asp Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Ser Gly Ser Ser Trp Phe Pro Tyr Trp Gly Gln Gly Thr
            100                 105                 110

Leu Val Thr Val Ser Ser
        115
```

<210> SEQ ID NO 7
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Leu Ile Glu Trp Val Arg Gln Ala Pro Gly Gln Gly Leu Glu Trp Met
        35                  40                  45

Gly Val Ile Asn Pro Gly Thr Gly Glu Thr Lys Tyr Asn Glu Asn Phe
    50                  55                  60

Arg Ala Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Arg Trp Gly Gln Gly Thr Leu Val Thr Val Ser Ser
            100                 105                 110
```

<210> SEQ ID NO 8
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

-continued

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met Asn Trp Val Arg Gln Ala Pro Gly Gln Gly Leu Glu Trp Met
        35                  40                  45

Gly Met Ile His Pro Ser Asp Ser Glu Ser Arg Leu Asn Gln Lys Phe
    50                  55                  60

Ile Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Val Trp Ala Met Asp Tyr Trp Gly Gln Gly Thr
            100                 105                 110

Leu Val Thr Val Ser Ser
        115

<210> SEQ ID NO 9
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: misc_feature
<222> LOCATION: (1)..(4)
<223> OTHER INFORMATION: /note="Residues given in the sequence have no
      preference with respect to those in the annotations for said
      position"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: misc_feature
<222> LOCATION: (7)..(7)
<223> OTHER INFORMATION: /note="Residue given in the sequence has no
      preference with respect to the annotation for said position"
<220> FEATURE:
<221> NAME/KEY: VARIANT
<222> LOCATION: (9)..(9)
<223> OTHER INFORMATION: /replace="Asp" or "Ala" or "Leu"
<220> FEATURE:
<221> NAME/KEY: VARIANT
<222> LOCATION: (10)..(10)
<223> OTHER INFORMATION: /replace="Thr" or "Phe"
<220> FEATURE:
<221> NAME/KEY: VARIANT
<222> LOCATION: (11)..(11)
<223> OTHER INFORMATION: /replace="Gln"
<220> FEATURE:

```
<221> NAME/KEY: VARIANT
<222> LOCATION: (12)..(12)
<223> OTHER INFORMATION: /replace="Ser" or "Pro"
<220> FEATURE:
<221> NAME/KEY: VARIANT
<222> LOCATION: (13)..(13)
<223> OTHER INFORMATION: /replace="Ala"
<220> FEATURE:
<221> NAME/KEY: VARIANT
<222> LOCATION: (14)..(14)
<223> OTHER INFORMATION: /replace="Thr"
<220> FEATURE:
<221> NAME/KEY: VARIANT
<222> LOCATION: (15)..(15)
<223> OTHER INFORMATION: /replace="Leu" or "Val"
<220> FEATURE:
<221> NAME/KEY: VARIANT
<222> LOCATION: (16)..(16)
<223> OTHER INFORMATION: /replace="Lys"
<220> FEATURE:
<221> NAME/KEY: VARIANT
<222> LOCATION: (17)..(17)
<223> OTHER INFORMATION: /replace="Gln" or "Asp"
<220> FEATURE:
<221> NAME/KEY: VARIANT
<222> LOCATION: (18)..(18)
<223> OTHER INFORMATION: /replace="Lys" or "Pro"
<220> FEATURE:
<221> NAME/KEY: VARIANT
<222> LOCATION: (19)..(19)
<223> OTHER INFORMATION: /replace="Val"
<220> FEATURE:
<221> NAME/KEY: VARIANT
<222> LOCATION: (20)..(20)
<223> OTHER INFORMATION: /replace="Ser"
<220> FEATURE:
<221> NAME/KEY: VARIANT
<222> LOCATION: (21)..(21)
<223> OTHER INFORMATION: /replace="Leu"
<220> FEATURE:
<221> NAME/KEY: VARIANT
<222> LOCATION: (22)..(22)
<223> OTHER INFORMATION: /replace="Thr" or "Asn"
<220> FEATURE:
<221> NAME/KEY: misc_feature
<222> LOCATION: (9)..(22)
<223> OTHER INFORMATION: /note="Residues given in the sequence have no
      preference with respect to those in the annotations for said
      position"
<220> FEATURE:
<221> NAME/KEY: VARIANT
<222> LOCATION: (24)..(24)
<223> OTHER INFORMATION: /replace="Arg"
<220> FEATURE:
<221> NAME/KEY: VARIANT
<222> LOCATION: (25)..(25)
<223> OTHER INFORMATION: /replace="Ser"
<220> FEATURE:
<221> NAME/KEY: misc_feature
<222> LOCATION: (24)..(25)
<223> OTHER INFORMATION: /note="Residues given in the sequence have no
      preference with respect to those in the annotations for said
      position"
<220> FEATURE:
<221> NAME/KEY: VARIANT
<222> LOCATION: (27)..(27)
<223> OTHER INFORMATION: /replace="Lys"
<220> FEATURE:
<221> NAME/KEY: VARIANT
<222> LOCATION: (28)..(28)
<223> OTHER INFORMATION: /replace="Ser" or "Asn"
<220> FEATURE:
<221> NAME/KEY: VARIANT
<222> LOCATION: (29)..(29)
<223> OTHER INFORMATION: /replace="Ile" or "Leu"
<220> FEATURE:
<221> NAME/KEY: VARIANT
<222> LOCATION: (30)..(30)
<223> OTHER INFORMATION: /replace="Ser" or "Val" or "Leu"
<220> FEATURE:
```

```
<221> NAME/KEY: VARIANT
<222> LOCATION: (31)..(31)
<223> OTHER INFORMATION: /replace="Asn" or "His"
<220> FEATURE:
<221> NAME/KEY: VARIANT
<222> LOCATION: (32)..(32)
<223> OTHER INFORMATION: /replace="Asn" or "Ser"
<220> FEATURE:
<221> NAME/KEY: VARIANT
<222> LOCATION: (33)..(33)
<223> OTHER INFORMATION: /replace="Leu" or "Asn" or "Gly"
<220> FEATURE:
<221> NAME/KEY: VARIANT
<222> LOCATION: (34)..(34)
<223> OTHER INFORMATION: /replace="His" or "Gly" or "Tyr"
<220> FEATURE:
<221> NAME/KEY: misc_feature
<222> LOCATION: (27)..(34)
<223> OTHER INFORMATION: /note="Residues given in the sequence have no
      preference with respect to those in the annotations for said
      position"
<220> FEATURE:
<221> NAME/KEY: VARIANT
<222> LOCATION: (36)..(36)
<223> OTHER INFORMATION: /replace="Tyr"
<220> FEATURE:
<221> NAME/KEY: VARIANT
<222> LOCATION: (37)..(37)
<223> OTHER INFORMATION: /replace="Leu"
<220> FEATURE:
<221> NAME/KEY: misc_feature
<222> LOCATION: (36)..(37)
<223> OTHER INFORMATION: /note="Residues given in the sequence have no
 preference with respect to those in the annotations for said position"
<220> FEATURE:
<221> NAME/KEY: VARIANT
<222> LOCATION: (39)..(39)
<223> OTHER INFORMATION: /replace="Arg"
<220> FEATURE:
<221> NAME/KEY: misc_feature
<222> LOCATION: (39)..(39)
<223> OTHER INFORMATION: /note="Residue given in the sequence has no
      preference with respect to the annotation for said position"
<220> FEATURE:
<221> NAME/KEY: VARIANT
<222> LOCATION: (41)..(41)
<223> OTHER INFORMATION: /replace="Asp"
<220> FEATURE:
<221> NAME/KEY: VARIANT
<222> LOCATION: (42)..(42)
<223> OTHER INFORMATION: /replace="Lys"
<220> FEATURE:
<221> NAME/KEY: VARIANT
<222> LOCATION: (43)..(43)
<223> OTHER INFORMATION: /replace="Ser" or "Pro"
<220> FEATURE:
<221> NAME/KEY: misc_feature
<222> LOCATION: (41)..(43)
<223> OTHER INFORMATION: /note="Residues given in the sequence have no
      preference with respect to those in the annotations for said
      position"
<220> FEATURE:
<221> NAME/KEY: VARIANT
<222> LOCATION: (45)..(45)
<223> OTHER INFORMATION: /replace="Arg" or "Gln"
<220> FEATURE:
<221> NAME/KEY: VARIANT
<222> LOCATION: (46)..(46)
<223> OTHER INFORMATION: /replace="Arg"
<220> FEATURE:
<221> NAME/KEY: misc_feature
<222> LOCATION: (45)..(46)
<223> OTHER INFORMATION: /note="Residues given in the sequence have no
      preference with respect to those in the annotations for said
      position"
<220> FEATURE:
<221> NAME/KEY: VARIANT
<222> LOCATION: (49)..(49)
<223> OTHER INFORMATION: /replace="Lys"
<220> FEATURE:
```

-continued

```
<221> NAME/KEY: VARIANT
<222> LOCATION: (50)..(50)
<223> OTHER INFORMATION: /replace="Tyr" or "Lys" or "Ile"
<220> FEATURE:
<221> NAME/KEY: VARIANT
<222> LOCATION: (51)..(51)
<223> OTHER INFORMATION: /replace="Thr" or "Val"
<220> FEATURE:
<221> NAME/KEY: VARIANT
<222> LOCATION: (52)..(52)
<223> OTHER INFORMATION: /replace="Tyr"
<220> FEATURE:
<221> NAME/KEY: VARIANT
<222> LOCATION: (53)..(53)
<223> OTHER INFORMATION: /replace="Gln" or "Asn"
<220> FEATURE:
<221> NAME/KEY: VARIANT
<222> LOCATION: (54)..(54)
<223> OTHER INFORMATION: /replace="Ser" or "Leu"
<220> FEATURE:
<221> NAME/KEY: VARIANT
<222> LOCATION: (55)..(55)
<223> OTHER INFORMATION: /replace="Ile" or "Phe" or "Glu"
<220> FEATURE:
<221> NAME/KEY: VARIANT
<222> LOCATION: (56)..(56)
<223> OTHER INFORMATION: /replace="Ser"
<220> FEATURE:
<221> NAME/KEY: misc_feature
<222> LOCATION: (49)..(56)
<223> OTHER INFORMATION: /note="Residues given in the sequence have no
      preference with respect to those in the annotations for said
      position"
<220> FEATURE:
<221> NAME/KEY: VARIANT
<222> LOCATION: (58)..(58)
<223> OTHER INFORMATION: /replace="Ile"
<220> FEATURE:
<221> NAME/KEY: misc_feature
<222> LOCATION: (58)..(58)
<223> OTHER INFORMATION: /note="Residue given in the sequence has no
      preference with respect to the annotation for said position"
<220> FEATURE:
<221> NAME/KEY: VARIANT
<222> LOCATION: (60)..(60)
<223> OTHER INFORMATION: /replace="Ala" or "Asp"
<220> FEATURE:
<221> NAME/KEY: misc_feature
<222> LOCATION: (60)..(60)
<223> OTHER INFORMATION: /note="Residue given in the sequence has no
      preference with respect to those in the annotations for said
      position"
<220> FEATURE:
<221> NAME/KEY: VARIANT
<222> LOCATION: (70)..(70)
<223> OTHER INFORMATION: /replace="Glu"
<220> FEATURE:
<221> NAME/KEY: misc_feature
<222> LOCATION: (70)..(70)
<223> OTHER INFORMATION: /note="Residue given in the sequence has no
      preference with respect to the annotation for said position"
<220> FEATURE:
<221> NAME/KEY: VARIANT
<222> LOCATION: (74)..(74)
<223> OTHER INFORMATION: /replace="Thr"
<220> FEATURE:
<221> NAME/KEY: misc_feature
<222> LOCATION: (74)..(74)
<223> OTHER INFORMATION: /note="Residue given in the sequence has no
      preference with respect to the annotation for said position"
<220> FEATURE:
<221> NAME/KEY: VARIANT
<222> LOCATION: (76)..(76)
<223> OTHER INFORMATION: /replace="Asn"
<220> FEATURE:
<221> NAME/KEY: VARIANT
<222> LOCATION: (77)..(77)
<223> OTHER INFORMATION: /replace="Arg"
<220> FEATURE:
<221> NAME/KEY: VARIANT
```

```
<222> LOCATION: (78)..(78)
<223> OTHER INFORMATION: /replace="Leu"
<220> FEATURE:
<221> NAME/KEY: VARIANT
<222> LOCATION: (79)..(79)
<223> OTHER INFORMATION: /replace="Glu"
<220> FEATURE:
<221> NAME/KEY: VARIANT
<222> LOCATION: (80)..(80)
<223> OTHER INFORMATION: /replace="Ala" or "Ser"
<220> FEATURE:
<221> NAME/KEY: misc_feature
<222> LOCATION: (76)..(80)
<223> OTHER INFORMATION: /note="Residues given in the sequence have no
      preference with respect to those in the annotations for said
      position"
<220> FEATURE:
<221> NAME/KEY: VARIANT
<222> LOCATION: (83)..(83)
<223> OTHER INFORMATION: /replace="Ala" or "Val"
<220> FEATURE:
<221> NAME/KEY: VARIANT
<222> LOCATION: (84)..(84)
<223> OTHER INFORMATION: /replace="Gly"
<220> FEATURE:
<221> NAME/KEY: VARIANT
<222> LOCATION: (85)..(85)
<223> OTHER INFORMATION: /replace="Val"
<220> FEATURE:
<221> NAME/KEY: misc_feature
<222> LOCATION: (83)..(85)
<223> OTHER INFORMATION: /note="Residues given in the sequence have no
      preference with respect to those in the annotations for said
      position"
<220> FEATURE:
<221> NAME/KEY: VARIANT
<222> LOCATION: (89)..(89)
<223> OTHER INFORMATION: /replace="Ser"
<220> FEATURE:
<221> NAME/KEY: VARIANT
<222> LOCATION: (90)..(90)
<223> OTHER INFORMATION: /replace="His"
<220> FEATURE:
<221> NAME/KEY: VARIANT
<222> LOCATION: (91)..(91)
<223> OTHER INFORMATION: /replace="Tyr"
<220> FEATURE:
<221> NAME/KEY: VARIANT
<222> LOCATION: (92)..(92)
<223> OTHER INFORMATION: /replace="Asn" or "Thr" or "Arg"
<220> FEATURE:
<221> NAME/KEY: VARIANT
<222> LOCATION: (93)..(93)
<223> OTHER INFORMATION: /replace="Arg" or "His" or "Glu"
<220> FEATURE:
<221> NAME/KEY: VARIANT
<222> LOCATION: (94)..(94)
<223> OTHER INFORMATION: /replace="Trp" or "Val" or "Leu"
<220> FEATURE:
<221> NAME/KEY: misc_feature
<222> LOCATION: (89)..(94)
<223> OTHER INFORMATION: /note="Residues given in the sequence have no
      preference with respect to those in the annotations for said
      position"
<220> FEATURE:
<221> NAME/KEY: VARIANT
<222> LOCATION: (96)..(96)
<223> OTHER INFORMATION: /replace="Tyr"
<220> FEATURE:
<221> NAME/KEY: misc_feature
<222> LOCATION: (96)..(96)
<223> OTHER INFORMATION: /note="Residue given in the sequence has no
      preference with respect to the annotation for said position"
<220> FEATURE:
<221> NAME/KEY: VARIANT
<222> LOCATION: (103)..(103)
<223> OTHER INFORMATION: /replace="Lys"
<220> FEATURE:
<221> NAME/KEY: misc_feature
<222> LOCATION: (103)..(103)
```

<223> OTHER INFORMATION: /note="Residue given in the sequence has no
      preference with respect to the annotation for said position"

<400> SEQUENCE: 9

```
Asp Ile Val Met Thr Gln Ser Pro Ser Ser Leu Ala Val Ser Pro Gly
1               5                   10                  15

Glu Arg Ala Thr Ile Ser Cys Lys Ala Ser Gln Asp Val Gly Thr Ala
            20                  25                  30

Val Ala Trp Phe Gln Gln Lys Pro Gly Gln Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Lys Ile Ser Ser Val Gln Pro
65                  70                  75                  80

Glu Asp Phe Ala Thr Tyr Cys Thr Gln Ser Ser Ser Tyr Pro Leu
                85                  90                  95

Thr Phe Gly Gln Gly Thr Arg Val Glu Ile Lys Arg
            100                 105
```

<210> SEQ ID NO 10
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: misc_feature
<222> LOCATION: (1)..(4)
<223> OTHER INFORMATION: /note="Residues given in the sequence have no
      preference with respect to those in the annotations for said
      position"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: misc_feature
<222> LOCATION: (7)..(7)
<223> OTHER INFORMATION: /note="Residue given in the sequence has no
      preference with respect to the annotation for said position"
<220> FEATURE:
<221> NAME/KEY: VARIANT
<222> LOCATION: (9)..(9)
<223> OTHER INFORMATION: /replace="Asp" or "Ala" or "Leu"
<220> FEATURE:
<221> NAME/KEY: VARIANT
<222> LOCATION: (10)..(10)
<223> OTHER INFORMATION: /replace="Thr" or "Phe"
<220> FEATURE:
<221> NAME/KEY: VARIANT
<222> LOCATION: (11)..(11)
<223> OTHER INFORMATION: /replace="Gln"
<220> FEATURE:
<221> NAME/KEY: VARIANT

```
<222> LOCATION: (12)..(12)
<223> OTHER INFORMATION: /replace="Ser" or "Pro"
<220> FEATURE:
<221> NAME/KEY: VARIANT
<222> LOCATION: (13)..(13)
<223> OTHER INFORMATION: /replace="Ala"
<220> FEATURE:
<221> NAME/KEY: VARIANT
<222> LOCATION: (14)..(14)
<223> OTHER INFORMATION: /replace="Thr"
<220> FEATURE:
<221> NAME/KEY: VARIANT
<222> LOCATION: (15)..(15)
<223> OTHER INFORMATION: /replace="Leu" or "Val"
<220> FEATURE:
<221> NAME/KEY: VARIANT
<222> LOCATION: (16)..(16)
<223> OTHER INFORMATION: /replace="Lys"
<220> FEATURE:
<221> NAME/KEY: VARIANT
<222> LOCATION: (17)..(17)
<223> OTHER INFORMATION: /replace="Gln" or "Asp"
<220> FEATURE:
<221> NAME/KEY: VARIANT
<222> LOCATION: (18)..(18)
<223> OTHER INFORMATION: /replace="Lys" or "Pro"
<220> FEATURE:
<221> NAME/KEY: VARIANT
<222> LOCATION: (19)..(19)
<223> OTHER INFORMATION: /replace="Val"
<220> FEATURE:
<221> NAME/KEY: VARIANT
<222> LOCATION: (20)..(20)
<223> OTHER INFORMATION: /replace="Ser"
<220> FEATURE:
<221> NAME/KEY: VARIANT
<222> LOCATION: (21)..(21)
<223> OTHER INFORMATION: /replace="Leu"
<220> FEATURE:
<221> NAME/KEY: VARIANT
<222> LOCATION: (22)..(22)
<223> OTHER INFORMATION: /replace="Thr" or "Asn"
<220> FEATURE:
<221> NAME/KEY: misc_feature
<222> LOCATION: (9)..(22)
<223> OTHER INFORMATION: /note="Residues given in the sequence have no
      preference with respect to those in the annotations for said
      position"
<220> FEATURE:
<221> NAME/KEY: VARIANT
<222> LOCATION: (24)..(24)
<223> OTHER INFORMATION: /replace="Arg"
<220> FEATURE:
<221> NAME/KEY: VARIANT
<222> LOCATION: (25)..(25)
<223> OTHER INFORMATION: /replace="Ser"
<220> FEATURE:
<221> NAME/KEY: misc_feature
<222> LOCATION: (24)..(25)
<223> OTHER INFORMATION: /note="Residues given in the sequence have no
      preference with respect to those in the annotations for said
      position"
<220> FEATURE:
<221> NAME/KEY: VARIANT
<222> LOCATION: (27)..(27)
<223> OTHER INFORMATION: /replace="Lys"
<220> FEATURE:
<221> NAME/KEY: VARIANT
<222> LOCATION: (28)..(28)
<223> OTHER INFORMATION: /replace="Ser" or "Asn"
<220> FEATURE:
<221> NAME/KEY: VARIANT
<222> LOCATION: (29)..(29)
<223> OTHER INFORMATION: /replace="Ile" or "Leu"
<220> FEATURE:
<221> NAME/KEY: VARIANT
<222> LOCATION: (30)..(30)
<223> OTHER INFORMATION: /replace="Ser" or "Val" or "Leu"
<220> FEATURE:
<221> NAME/KEY: VARIANT
```

```
<222> LOCATION: (31)..(31)
<223> OTHER INFORMATION: /replace="Asn" or "His"
<220> FEATURE:
<221> NAME/KEY: VARIANT
<222> LOCATION: (32)..(32)
<223> OTHER INFORMATION: /replace="Asn" or "Ser"
<220> FEATURE:
<221> NAME/KEY: VARIANT
<222> LOCATION: (33)..(33)
<223> OTHER INFORMATION: /replace="Leu" or "Asn" or "Gly"
<220> FEATURE:
<221> NAME/KEY: VARIANT
<222> LOCATION: (34)..(34)
<223> OTHER INFORMATION: /replace="His" or "Gly" or "Tyr"
<220> FEATURE:
<221> NAME/KEY: VARIANT
<222> LOCATION: (35)..(35)
<223> OTHER INFORMATION: /replace="Thr"
<220> FEATURE:
<221> NAME/KEY: VARIANT
<222> LOCATION: (36)..(36)
<223> OTHER INFORMATION: /replace="Tyr"
<220> FEATURE:
<221> NAME/KEY: VARIANT
<222> LOCATION: (37)..(37)
<223> OTHER INFORMATION: /replace="Met"
<220> FEATURE:
<221> NAME/KEY: VARIANT
<222> LOCATION: (38)..(38)
<223> OTHER INFORMATION: /replace="His"
<220> FEATURE:
<221> NAME/KEY: misc_feature
<222> LOCATION: (27)..(38)
<223> OTHER INFORMATION: /note="Residues given in the sequence have no
      preference with respect to those in the annotations for said
      position"
<220> FEATURE:
<221> NAME/KEY: VARIANT
<222> LOCATION: (40)..(40)
<223> OTHER INFORMATION: /replace="Tyr"
<220> FEATURE:
<221> NAME/KEY: VARIANT
<222> LOCATION: (41)..(41)
<223> OTHER INFORMATION: /replace="Leu"
<220> FEATURE:
<221> NAME/KEY: misc_feature
<222> LOCATION: (40)..(41)
<223> OTHER INFORMATION: /note="Residues given in the sequence have no
      preference with respect to those in the annotations for said
      position"
<220> FEATURE:
<221> NAME/KEY: VARIANT
<222> LOCATION: (43)..(43)
<223> OTHER INFORMATION: /replace="Arg"
<220> FEATURE:
<221> NAME/KEY: misc_feature
<222> LOCATION: (43)..(43)
<223> OTHER INFORMATION: /note="Residue given in the sequence has no
      preference with respect to the annotation for said position"
<220> FEATURE:
<221> NAME/KEY: VARIANT
<222> LOCATION: (45)..(45)
<223> OTHER INFORMATION: /replace="Asp"
<220> FEATURE:
<221> NAME/KEY: VARIANT
<222> LOCATION: (46)..(46)
<223> OTHER INFORMATION: /replace="Lys"
<220> FEATURE:
<221> NAME/KEY: VARIANT
<222> LOCATION: (47)..(47)
<223> OTHER INFORMATION: /replace="Ser" or "Pro"
<220> FEATURE:
<221> NAME/KEY: VARIANT
<222> LOCATION: (48)..(48)
<223> OTHER INFORMATION: /replace="Arg" or "Gln"
<220> FEATURE:
<221> NAME/KEY: VARIANT
<222> LOCATION: (49)..(49)
<223> OTHER INFORMATION: /replace="Arg"
<220> FEATURE:
```

```
<221> NAME/KEY: misc_feature
<222> LOCATION: (45)..(49)
<223> OTHER INFORMATION: /note="Residues given in the sequence have no
      preference with respect to those in the annotations for said
      position"
<220> FEATURE:
<221> NAME/KEY: VARIANT
<222> LOCATION: (52)..(52)
<223> OTHER INFORMATION: /replace="Lys"
<220> FEATURE:
<221> NAME/KEY: VARIANT
<222> LOCATION: (53)..(53)
<223> OTHER INFORMATION: /replace="Tyr" or "Lys" or "Ile"
<220> FEATURE:
<221> NAME/KEY: VARIANT
<222> LOCATION: (54)..(54)
<223> OTHER INFORMATION: /replace="Thr" or "Val"
<220> FEATURE:
<221> NAME/KEY: VARIANT
<222> LOCATION: (55)..(55)
<223> OTHER INFORMATION: /replace="Tyr"
<220> FEATURE:
<221> NAME/KEY: VARIANT
<222> LOCATION: (56)..(56)
<223> OTHER INFORMATION: /replace="Gln" or "Asn"
<220> FEATURE:
<221> NAME/KEY: VARIANT
<222> LOCATION: (57)..(57)
<223> OTHER INFORMATION: /replace="Ser" or "Leu"
<220> FEATURE:
<221> NAME/KEY: VARIANT
<222> LOCATION: (58)..(58)
<223> OTHER INFORMATION: /replace="Ile" or "Phe" or "Glu"
<220> FEATURE:
<221> NAME/KEY: VARIANT
<222> LOCATION: (59)..(59)
<223> OTHER INFORMATION: /replace="Ser"
<220> FEATURE:
<221> NAME/KEY: misc_feature
<222> LOCATION: (52)..(59)
<223> OTHER INFORMATION: /note="Residues given in the sequence have no
      preference with respect to those in the annotations for said
      position"
<220> FEATURE:
<221> NAME/KEY: VARIANT
<222> LOCATION: (61)..(61)
<223> OTHER INFORMATION: /replace="Ile"
<220> FEATURE:
<221> NAME/KEY: misc_feature
<222> LOCATION: (61)..(61)
<223> OTHER INFORMATION: /note="Residue given in the sequence has no
      preference with respect to the annotation for said position"
<220> FEATURE:
<221> NAME/KEY: VARIANT
<222> LOCATION: (63)..(63)
<223> OTHER INFORMATION: /replace="Ala" or "Asp"
<220> FEATURE:
<221> NAME/KEY: misc_feature
<222> LOCATION: (63)..(63)
<223> OTHER INFORMATION: /note="Residue given in the sequence has no
      preference with respect to those in the annotations for said
      position"
<220> FEATURE:
<221> NAME/KEY: VARIANT
<222> LOCATION: (73)..(73)
<223> OTHER INFORMATION: /replace="Glu"
<220> FEATURE:
<221> NAME/KEY: misc_feature
<222> LOCATION: (73)..(73)
<223> OTHER INFORMATION: /note="Residue given in the sequence has no
      preference with respect to the annotation for said position"
<220> FEATURE:
<221> NAME/KEY: VARIANT
<222> LOCATION: (77)..(77)
<223> OTHER INFORMATION: /replace="Thr"
<220> FEATURE:
<221> NAME/KEY: misc_feature
<222> LOCATION: (77)..(77)
<223> OTHER INFORMATION: /note="Residue given in the sequence has no
      preference with respect to the annotation for said position"
```

```
<220> FEATURE:
<221> NAME/KEY: VARIANT
<222> LOCATION: (79)..(79)
<223> OTHER INFORMATION: /replace="Asn"
<220> FEATURE:
<221> NAME/KEY: VARIANT
<222> LOCATION: (80)..(80)
<223> OTHER INFORMATION: /replace="Arg"
<220> FEATURE:
<221> NAME/KEY: VARIANT
<222> LOCATION: (81)..(81)
<223> OTHER INFORMATION: /replace="Leu"
<220> FEATURE:
<221> NAME/KEY: VARIANT
<222> LOCATION: (82)..(82)
<223> OTHER INFORMATION: /replace="Glu"
<220> FEATURE:
<221> NAME/KEY: VARIANT
<222> LOCATION: (83)..(83)
<223> OTHER INFORMATION: /replace="Ala" or "Ser"
<220> FEATURE:
<221> NAME/KEY: misc_feature
<222> LOCATION: (79)..(83)
<223> OTHER INFORMATION: /note="Residues given in the sequence have no
      preference with respect to those in the annotations for said
      position"
<220> FEATURE:
<221> NAME/KEY: VARIANT
<222> LOCATION: (86)..(86)
<223> OTHER INFORMATION: /replace="Ala" or "Val"
<220> FEATURE:
<221> NAME/KEY: VARIANT
<222> LOCATION: (87)..(87)
<223> OTHER INFORMATION: /replace="Gly"
<220> FEATURE:
<221> NAME/KEY: VARIANT
<222> LOCATION: (88)..(88)
<223> OTHER INFORMATION: /replace="Val"
<220> FEATURE:
<221> NAME/KEY: misc_feature
<222> LOCATION: (86)..(88)
<223> OTHER INFORMATION: /note="Residues given in the sequence have no
      preference with respect to those in the annotations for said
      position"
<220> FEATURE:
<221> NAME/KEY: VARIANT
<222> LOCATION: (92)..(92)
<223> OTHER INFORMATION: /replace="Ser"
<220> FEATURE:
<221> NAME/KEY: VARIANT
<222> LOCATION: (93)..(93)
<223> OTHER INFORMATION: /replace="His"
<220> FEATURE:
<221> NAME/KEY: VARIANT
<222> LOCATION: (94)..(94)
<223> OTHER INFORMATION: /replace="Tyr"
<220> FEATURE:
<221> NAME/KEY: VARIANT
<222> LOCATION: (95)..(95)
<223> OTHER INFORMATION: /replace="Asn" or "Thr" or "Arg"
<220> FEATURE:
<221> NAME/KEY: VARIANT
<222> LOCATION: (96)..(96)
<223> OTHER INFORMATION: /replace="Arg" or "His" or "Glu"
<220> FEATURE:
<221> NAME/KEY: VARIANT
<222> LOCATION: (97)..(97)
<223> OTHER INFORMATION: /replace="Trp" or "Val" or "Leu"
<220> FEATURE:
<221> NAME/KEY: misc_feature
<222> LOCATION: (92)..(97)
<223> OTHER INFORMATION: /note="Residues given in the sequence have no
      preference with respect to those in the annotations for said
      position"
<220> FEATURE:
<221> NAME/KEY: VARIANT
<222> LOCATION: (99)..(99)
<223> OTHER INFORMATION: /replace="Tyr"
<220> FEATURE:
<221> NAME/KEY: misc_feature
```

```
<222> LOCATION: (99)..(99)
<223> OTHER INFORMATION: /note="Residue given in the sequence has no
      preference with respect to the annotation for said position"
<220> FEATURE:
<221> NAME/KEY: VARIANT
<222> LOCATION: (106)..(106)
<223> OTHER INFORMATION: /replace="Lys"
<220> FEATURE:
<221> NAME/KEY: misc_feature
<222> LOCATION: (106)..(106)
<223> OTHER INFORMATION: /note="Residue given in the sequence has no
      preference with respect to the annotation for said position"

<400> SEQUENCE: 10

Asp Ile Val Met Thr Gln Ser Pro Ser Ser Leu Ala Val Ser Pro Gly
1               5                   10                  15

Glu Arg Ala Thr Ile Ser Cys Lys Ala Ser Gln Asp Val Gly Thr Ala
            20                  25                  30

Val Ala Asn Thr Tyr Phe Trp Phe Gln Gln Lys Pro Gly Gln Ala Lys
        35                  40                  45

Leu Leu Ile Tyr Trp Ala Ser Thr Arg His Thr Gly Val Pro Ser Arg
    50                  55                  60

Phe Ser Gly Ser Gly Ser Gly Thr Asp Phe Thr Leu Lys Ile Ser Ser
65                  70                  75                  80

Val Gln Pro Glu Asp Phe Ala Thr Tyr Tyr Cys Gln Gln Ser Ser Ser
                85                  90                  95

Tyr Pro Leu Thr Phe Gly Gln Gly Thr Arg Val Glu Ile Lys Arg
            100                 105                 110

<210> SEQ ID NO 11
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: misc_feature
<222> LOCATION: (1)..(4)
<223> OTHER INFORMATION: /note="Residues given in the sequence have no
      preference with respect to those in the annotations for said
      position"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: misc_feature
<222> LOCATION: (7)..(7)
<223> OTHER INFORMATION: /note="Residue given in the sequence has no
      preference with respect to the annotation for said position"
<220> FEATURE:
<221> NAME/KEY: VARIANT
<222> LOCATION: (9)..(9)
<223> OTHER INFORMATION: /replace="Asp" or "Ala" or "Leu"
```

```
<220> FEATURE:
<221> NAME/KEY: VARIANT
<222> LOCATION: (10)..(10)
<223> OTHER INFORMATION: /replace="Thr" or "Phe"
<220> FEATURE:
<221> NAME/KEY: VARIANT
<222> LOCATION: (11)..(11)
<223> OTHER INFORMATION: /replace="Gln"
<220> FEATURE:
<221> NAME/KEY: VARIANT
<222> LOCATION: (12)..(12)
<223> OTHER INFORMATION: /replace="Ser" or "Pro"
<220> FEATURE:
<221> NAME/KEY: VARIANT
<222> LOCATION: (13)..(13)
<223> OTHER INFORMATION: /replace="Ala"
<220> FEATURE:
<221> NAME/KEY: VARIANT
<222> LOCATION: (14)..(14)
<223> OTHER INFORMATION: /replace="Thr"
<220> FEATURE:
<221> NAME/KEY: VARIANT
<222> LOCATION: (15)..(15)
<223> OTHER INFORMATION: /replace="Leu" or "Val"
<220> FEATURE:
<221> NAME/KEY: VARIANT
<222> LOCATION: (16)..(16)
<223> OTHER INFORMATION: /replace="Lys"
<220> FEATURE:
<221> NAME/KEY: VARIANT
<222> LOCATION: (17)..(17)
<223> OTHER INFORMATION: /replace="Gln" or "Asp"
<220> FEATURE:
<221> NAME/KEY: VARIANT
<222> LOCATION: (18)..(18)
<223> OTHER INFORMATION: /replace="Lys" or "Pro"
<220> FEATURE:
<221> NAME/KEY: VARIANT
<222> LOCATION: (19)..(19)
<223> OTHER INFORMATION: /replace="Val"
<220> FEATURE:
<221> NAME/KEY: VARIANT
<222> LOCATION: (20)..(20)
<223> OTHER INFORMATION: /replace="Ser"
<220> FEATURE:
<221> NAME/KEY: VARIANT
<222> LOCATION: (21)..(21)
<223> OTHER INFORMATION: /replace="Leu"
<220> FEATURE:
<221> NAME/KEY: VARIANT
<222> LOCATION: (22)..(22)
<223> OTHER INFORMATION: /replace="Thr" or "Asn"
<220> FEATURE:
<221> NAME/KEY: misc_feature
<222> LOCATION: (9)..(22)
<223> OTHER INFORMATION: /note="Residues given in the sequence have no
      preference with respect to those in the annotations for said
      position"
<220> FEATURE:
<221> NAME/KEY: VARIANT
<222> LOCATION: (24)..(24)
<223> OTHER INFORMATION: /replace="Arg"
<220> FEATURE:
<221> NAME/KEY: VARIANT
<222> LOCATION: (25)..(25)
<223> OTHER INFORMATION: /replace="Ser"
<220> FEATURE:
<221> NAME/KEY: misc_feature
<222> LOCATION: (24)..(25)
<223> OTHER INFORMATION: /note="Residues given in the sequence have no
      preference with respect to those in the annotations for said
      position"
<220> FEATURE:
<221> NAME/KEY: VARIANT
<222> LOCATION: (27)..(27)
<223> OTHER INFORMATION: /replace="Lys"
<220> FEATURE:
<221> NAME/KEY: VARIANT
<222> LOCATION: (28)..(28)
<223> OTHER INFORMATION: /replace="Ser" or "Asn"
```

```
<220> FEATURE:
<221> NAME/KEY: VARIANT
<222> LOCATION: (29)..(29)
<223> OTHER INFORMATION: /replace="Ile" or "Leu"
<220> FEATURE:
<221> NAME/KEY: VARIANT
<222> LOCATION: (30)..(30)
<223> OTHER INFORMATION: /replace="Ser" or "Val" or "Leu"
<220> FEATURE:
<221> NAME/KEY: VARIANT
<222> LOCATION: (31)..(31)
<223> OTHER INFORMATION: /replace="Asn" or "His"
<220> FEATURE:
<221> NAME/KEY: VARIANT
<222> LOCATION: (32)..(32)
<223> OTHER INFORMATION: /replace="Asn" or "Ser"
<220> FEATURE:
<221> NAME/KEY: VARIANT
<222> LOCATION: (33)..(33)
<223> OTHER INFORMATION: /replace="Leu" or "Asn" or "Gly"
<220> FEATURE:
<221> NAME/KEY: VARIANT
<222> LOCATION: (34)..(34)
<223> OTHER INFORMATION: /replace="His" or "Gly" or "Tyr"
<220> FEATURE:
<221> NAME/KEY: VARIANT
<222> LOCATION: (35)..(35)
<223> OTHER INFORMATION: /replace="Thr"
<220> FEATURE:
<221> NAME/KEY: VARIANT
<222> LOCATION: (36)..(36)
<223> OTHER INFORMATION: /replace="Tyr"
<220> FEATURE:
<221> NAME/KEY: VARIANT
<222> LOCATION: (37)..(37)
<223> OTHER INFORMATION: /replace="Met"
<220> FEATURE:
<221> NAME/KEY: VARIANT
<222> LOCATION: (38)..(38)
<223> OTHER INFORMATION: /replace="His"
<220> FEATURE:
<221> NAME/KEY: misc_feature
<222> LOCATION: (27)..(38)
<223> OTHER INFORMATION: /note="Residues given in the sequence have no
     preference with respect to those in the annotations for said
     position"
<220> FEATURE:
<221> NAME/KEY: VARIANT
<222> LOCATION: (41)..(41)
<223> OTHER INFORMATION: /replace="Tyr"
<220> FEATURE:
<221> NAME/KEY: VARIANT
<222> LOCATION: (42)..(42)
<223> OTHER INFORMATION: /replace="Leu"
<220> FEATURE:
<221> NAME/KEY: misc_feature
<222> LOCATION: (41)..(42)
<223> OTHER INFORMATION: /note="Residues given in the sequence have no
     preference with respect to those in the annotations for said
     position"
<220> FEATURE:
<221> NAME/KEY: VARIANT
<222> LOCATION: (44)..(44)
<223> OTHER INFORMATION: /replace="Arg"
<220> FEATURE:
<221> NAME/KEY: misc_feature
<222> LOCATION: (44)..(44)
<223> OTHER INFORMATION: /note="Residue given in the sequence has no
     preference with respect to the annotation for said position"
<220> FEATURE:
<221> NAME/KEY: VARIANT
<222> LOCATION: (46)..(46)
<223> OTHER INFORMATION: /replace="Asp"
<220> FEATURE:
<221> NAME/KEY: VARIANT
<222> LOCATION: (47)..(47)
<223> OTHER INFORMATION: /replace="Lys"
<220> FEATURE:
<221> NAME/KEY: VARIANT
<222> LOCATION: (48)..(48)
```

```
<223> OTHER INFORMATION: /replace="Ser" or "Pro"
<220> FEATURE:
<221> NAME/KEY: VARIANT
<222> LOCATION: (49)..(49)
<223> OTHER INFORMATION: /replace="Arg" or "Gln"
<220> FEATURE:
<221> NAME/KEY: VARIANT
<222> LOCATION: (50)..(50)
<223> OTHER INFORMATION: /replace="Arg"
<220> FEATURE:
<221> NAME/KEY: misc_feature
<222> LOCATION: (46)..(50)
<223> OTHER INFORMATION: /note="Residues given in the sequence have no
      preference with respect to those in the annotations for said
      position"
<220> FEATURE:
<221> NAME/KEY: VARIANT
<222> LOCATION: (53)..(53)
<223> OTHER INFORMATION: /replace="Lys"
<220> FEATURE:
<221> NAME/KEY: VARIANT
<222> LOCATION: (54)..(54)
<223> OTHER INFORMATION: /replace="Tyr" or "Lys" or "Ile"
<220> FEATURE:
<221> NAME/KEY: VARIANT
<222> LOCATION: (55)..(55)
<223> OTHER INFORMATION: /replace="Thr" or "Val"
<220> FEATURE:
<221> NAME/KEY: VARIANT
<222> LOCATION: (56)..(56)
<223> OTHER INFORMATION: /replace="Tyr"
<220> FEATURE:
<221> NAME/KEY: VARIANT
<222> LOCATION: (57)..(57)
<223> OTHER INFORMATION: /replace="Gln" or "Asn"
<220> FEATURE:
<221> NAME/KEY: VARIANT
<222> LOCATION: (58)..(58)
<223> OTHER INFORMATION: /replace="Ser" or "Leu"
<220> FEATURE:
<221> NAME/KEY: VARIANT
<222> LOCATION: (59)..(59)
<223> OTHER INFORMATION: /replace="Ile" or "Phe" or "Glu"
<220> FEATURE:
<221> NAME/KEY: VARIANT
<222> LOCATION: (60)..(60)
<223> OTHER INFORMATION: /replace="Ser"
<220> FEATURE:
<221> NAME/KEY: misc_feature
<222> LOCATION: (53)..(60)
<223> OTHER INFORMATION: /note="Residues given in the sequence have no
      preference with respect to those in the annotations for said
      position"
<220> FEATURE:
<221> NAME/KEY: VARIANT
<222> LOCATION: (62)..(62)
<223> OTHER INFORMATION: /replace="Ile"
<220> FEATURE:
<221> NAME/KEY: misc_feature
<222> LOCATION: (62)..(62)
<223> OTHER INFORMATION: /note="Residue given in the sequence has no
      preference with respect to the annotation for said position"
<220> FEATURE:
<221> NAME/KEY: VARIANT
<222> LOCATION: (64)..(64)
<223> OTHER INFORMATION: /replace="Ala" or "Asp"
<220> FEATURE:
<221> NAME/KEY: misc_feature
<222> LOCATION: (64)..(64)
<223> OTHER INFORMATION: /note="Residue given in the sequence has no
      preference with respect to those in the annotations for said
      position"
<220> FEATURE:
<221> NAME/KEY: VARIANT
<222> LOCATION: (74)..(74)
<223> OTHER INFORMATION: /replace="Glu"
<220> FEATURE:
<221> NAME/KEY: misc_feature
<222> LOCATION: (74)..(74)
<223> OTHER INFORMATION: /note="Residue given in the sequence has no
```

-continued

```
      preference with respect to the annotation for said position"
<220> FEATURE:
<221> NAME/KEY: VARIANT
<222> LOCATION: (78)..(78)
<223> OTHER INFORMATION: /replace="Thr"
<220> FEATURE:
<221> NAME/KEY: misc_feature
<222> LOCATION: (78)..(78)
<223> OTHER INFORMATION: /note="Residue given in the sequence has no
      preference with respect to the annotation for said position"
<220> FEATURE:
<221> NAME/KEY: VARIANT
<222> LOCATION: (80)..(80)
<223> OTHER INFORMATION: /replace="Asn"
<220> FEATURE:
<221> NAME/KEY: VARIANT
<222> LOCATION: (81)..(81)
<223> OTHER INFORMATION: /replace="Arg"
<220> FEATURE:
<221> NAME/KEY: VARIANT
<222> LOCATION: (82)..(82)
<223> OTHER INFORMATION: /replace="Leu"
<220> FEATURE:
<221> NAME/KEY: VARIANT
<222> LOCATION: (83)..(83)
<223> OTHER INFORMATION: /replace="Glu"
<220> FEATURE:
<221> NAME/KEY: VARIANT
<222> LOCATION: (84)..(84)
<223> OTHER INFORMATION: /replace="Ala" or "Ser"
<220> FEATURE:
<221> NAME/KEY: misc_feature
<222> LOCATION: (80)..(84)
<223> OTHER INFORMATION: /note="Residues given in the sequence have no
      preference with respect to those in the annotations for said
      position"
<220> FEATURE:
<221> NAME/KEY: VARIANT
<222> LOCATION: (87)..(87)
<223> OTHER INFORMATION: /replace="Ala" or "Val"
<220> FEATURE:
<221> NAME/KEY: VARIANT
<222> LOCATION: (88)..(88)
<223> OTHER INFORMATION: /replace="Gly"
<220> FEATURE:
<221> NAME/KEY: VARIANT
<222> LOCATION: (89)..(89)
<223> OTHER INFORMATION: /replace="Val"
<220> FEATURE:
<221> NAME/KEY: misc_feature
<222> LOCATION: (87)..(89)
<223> OTHER INFORMATION: /note="Residues given in the sequence have no
      preference with respect to those in the annotations for said
      position"
<220> FEATURE:
<221> NAME/KEY: VARIANT
<222> LOCATION: (93)..(93)
<223> OTHER INFORMATION: /replace="Ser"
<220> FEATURE:
<221> NAME/KEY: VARIANT
<222> LOCATION: (94)..(94)
<223> OTHER INFORMATION: /replace="His"
<220> FEATURE:
<221> NAME/KEY: VARIANT
<222> LOCATION: (95)..(95)
<223> OTHER INFORMATION: /replace="Tyr"
<220> FEATURE:
<221> NAME/KEY: VARIANT
<222> LOCATION: (96)..(96)
<223> OTHER INFORMATION: /replace="Asn" or "Thr" or "Arg"
<220> FEATURE:
<221> NAME/KEY: VARIANT
<222> LOCATION: (97)..(97)
<223> OTHER INFORMATION: /replace="Arg" or "His" or "Glu"
<220> FEATURE:
<221> NAME/KEY: VARIANT
<222> LOCATION: (98)..(98)
<223> OTHER INFORMATION: /replace="Trp" or "Val" or "Leu"
<220> FEATURE:
<221> NAME/KEY: misc_feature
```

```
<222> LOCATION: (93)..(98)
<223> OTHER INFORMATION: /note="Residues given in the sequence have no
      preference with respect to those in the annotations for said
      position"
<220> FEATURE:
<221> NAME/KEY: VARIANT
<222> LOCATION: (100)..(100)
<223> OTHER INFORMATION: /replace="Tyr"
<220> FEATURE:
<221> NAME/KEY: misc_feature
<222> LOCATION: (100)..(100)
<223> OTHER INFORMATION: /note="Residue given in the sequence has no
      preference with respect to the annotation for said position"
<220> FEATURE:
<221> NAME/KEY: VARIANT
<222> LOCATION: (107)..(107)
<223> OTHER INFORMATION: /replace="Lys"
<220> FEATURE:
<221> NAME/KEY: misc_feature
<222> LOCATION: (107)..(107)
<223> OTHER INFORMATION: /note="Residue given in the sequence has no
      preference with respect to the annotation for said position"

<400> SEQUENCE: 11

Asp Ile Val Met Thr Gln Ser Pro Ser Ser Leu Ala Val Ser Pro Gly
1               5                   10                  15

Glu Arg Ala Thr Ile Ser Cys Lys Ala Ser Gln Asp Val Gly Thr Ala
            20                  25                  30

Val Ala Asn Thr Tyr Phe His Trp Phe Gln Lys Pro Gly Gln Ala
        35                  40                  45

Lys Leu Leu Ile Tyr Trp Ala Ser Thr Arg His Thr Gly Val Pro Ser
    50                  55                  60

Arg Phe Ser Gly Ser Gly Ser Gly Thr Asp Phe Thr Leu Lys Ile Ser
65                  70                  75                  80

Ser Val Gln Pro Glu Asp Phe Ala Thr Tyr Tyr Cys Gln Gln Ser Ser
                85                  90                  95

Ser Tyr Pro Leu Thr Phe Gly Gln Gly Thr Arg Val Glu Ile Lys Arg
            100                 105                 110

<210> SEQ ID NO 12
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys Arg
            100                 105
```

```
<210> SEQ ID NO 13
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Glu Ile Val Leu Thr Gln Ser Pro Asp Phe Gln Ser Val Thr Pro Lys
1               5                  10                  15

Glu Lys Val Thr Ile Thr Cys Arg Ala Ser Gln Ser Ile Ser Asn Asn
            20                  25                  30

Leu His Trp Tyr Gln Gln Lys Pro Asp Gln Ser Pro Lys Leu Leu Ile
        35                  40                  45

Lys Tyr Thr Tyr Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Arg Trp Pro Leu
                85                  90                  95

Thr Phe Gly Gln Gly Thr Lys Val Glu Ile Lys Arg
            100                 105

<210> SEQ ID NO 14
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Ile Val Met Thr Gln Ser Pro Ala Thr Leu Ser Val Ser Pro Gly
1               5                  10                  15

Glu Lys Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Thr Tyr Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Arg Trp Pro Leu
                85                  90                  95

Thr Phe Gly Gln Gly Thr Arg Val Glu Ile Lys Arg
            100                 105

<210> SEQ ID NO 15
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Val Val Met Thr Gln Ser Pro Leu Ser Leu Pro Val Thr Leu Gly
1               5                  10                  15
```

```
Gln Pro Ala Ser Ile Ser Cys Arg Ser Ser Gln Asn Leu Val His Ser
            20                  25                  30

Asn Gly Asn Thr Tyr Phe His Trp Phe Gln Gln Arg Pro Gly Gln Ser
        35                  40                  45

Pro Arg Arg Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Val Glu Ile Lys
            100                 105                 110

Arg

<210> SEQ ID NO 16
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Asn Leu Val His Ser
            20                  25                  30

Asn Gly Asn Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Val Glu Ile Lys
            100                 105                 110

Arg

<210> SEQ ID NO 17
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Ile Thr Ser Asn Leu Glu Ser Gly Val Pro Asp
 50                  55                  60

Arg Phe Ser Gly Ser Gly Ser Gly Thr Asp Phe Thr Leu Thr Ile Ser
```

-continued

```
                65                  70                  75                  80
Ser Leu Gln Ala Glu Asp Val Ala Val Tyr Tyr Cys Gln His Ser Arg
                    85                  90                  95
Glu Leu Pro Tyr Thr Phe Gly Gln Gly Thr Lys Val Glu Ile Lys Arg
                    100                 105                 110

<210> SEQ ID NO 18
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ser" or "Thr" or "Asn"
<220> FEATURE:
<221> NAME/KEY: misc_feature
<222> LOCATION: (1)..(1)
<223> OTHER INFORMATION: /note="Residue given in the sequence has no
      preference with respect to those in the annotations for said
      position"
<220> FEATURE:
<221> NAME/KEY: VARIANT
<222> LOCATION: (3)..(3)
<223> OTHER INFORMATION: /replace="Leu" or "Trp"
<220> FEATURE:
<221> NAME/KEY: VARIANT
<222> LOCATION: (4)..(4)
<223> OTHER INFORMATION: /replace="Met"
<220> FEATURE:
<221> NAME/KEY: VARIANT
<222> LOCATION: (5)..(5)
<223> OTHER INFORMATION: /replace="His" or "Glu" or "Asn"
<220> FEATURE:
<221> NAME/KEY: misc_feature
<222> LOCATION: (3)..(5)
<223> OTHER INFORMATION: /note="Residues given in the sequence have no
      preference with respect to those in the annotations for said
      position"

<400> SEQUENCE: 18

Asp Tyr Tyr Ile Tyr
1               5

<210> SEQ ID NO 19
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Met" or "Val" or "Trp"
<220> FEATURE:
<221> NAME/KEY: misc_feature
<222> LOCATION: (1)..(1)
<223> OTHER INFORMATION: /note="Residue given in the sequence has no
      preference with respect to those in the annotations for said
      position"
<220> FEATURE:
<221> NAME/KEY: VARIANT
<222> LOCATION: (3)..(3)
<223> OTHER INFORMATION: /replace="Asn" or "His" or "Phe"
<220> FEATURE:
<221> NAME/KEY: misc_feature
<222> LOCATION: (3)..(3)
<223> OTHER INFORMATION: /note="Residue given in the sequence has no
      preference with respect to those in the annotations for said
      position"
```

```
<220> FEATURE:
<221> NAME/KEY: VARIANT
<222> LOCATION: (5)..(5)
<223> OTHER INFORMATION: /replace="Gly" or "Ser"
<220> FEATURE:
<221> NAME/KEY: VARIANT
<222> LOCATION: (6)..(6)
<223> OTHER INFORMATION: /replace="Ser" or "Thr" or "Asp"
<220> FEATURE:
<221> NAME/KEY: VARIANT
<222> LOCATION: (7)..(7)
<223> OTHER INFORMATION: /replace="Ser" or "Asp"
<220> FEATURE:
<221> NAME/KEY: VARIANT
<222> LOCATION: (8)..(8)
<223> OTHER INFORMATION: /replace="Asp" or "Glu" or "Ile"
<220> FEATURE:
<221> NAME/KEY: VARIANT
<222> LOCATION: (9)..(9)
<223> OTHER INFORMATION: /replace="Ser"
<220> FEATURE:
<221> NAME/KEY: VARIANT
<222> LOCATION: (10)..(10)
<223> OTHER INFORMATION: /replace="Arg"
<220> FEATURE:
<221> NAME/KEY: VARIANT
<222> LOCATION: (11)..(11)
<223> OTHER INFORMATION: /replace="Leu"
<220> FEATURE:
<221> NAME/KEY: misc_feature
<222> LOCATION: (5)..(11)
<223> OTHER INFORMATION: /note="Residues given in the sequence have no
      preference with respect to those in the annotations for said
      position"
<220> FEATURE:
<221> NAME/KEY: VARIANT
<222> LOCATION: (13)..(13)
<223> OTHER INFORMATION: /replace="Glu"
<220> FEATURE:
<221> NAME/KEY: VARIANT
<222> LOCATION: (14)..(14)
<223> OTHER INFORMATION: /replace="Asn"
<220> FEATURE:
<221> NAME/KEY: misc_feature
<222> LOCATION: (13)..(14)
<223> OTHER INFORMATION: /note="Residues given in the sequence have no
      preference with respect to those in the annotations for said
      position"
<220> FEATURE:
<221> NAME/KEY: VARIANT
<222> LOCATION: (16)..(16)
<223> OTHER INFORMATION: /replace="Ile" or "Arg"
<220> FEATURE:
<221> NAME/KEY: VARIANT
<222> LOCATION: (17)..(17)
<223> OTHER INFORMATION: /replace="Ala" or "Asp"
<220> FEATURE:
<221> NAME/KEY: misc_feature
<222> LOCATION: (16)..(17)
<223> OTHER INFORMATION: /note="Residues given in the sequence have no
      preference with respect to those in the annotations for said
      position"

<400> SEQUENCE: 19

Tyr Ile Asp Pro Tyr Asn Gly Gly Thr Lys Tyr Asn Gln Lys Phe Lys
1               5                   10                  15
Gly

<210> SEQ ID NO 20
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: VARIANT
<222> LOCATION: (2)..(2)
<223> OTHER INFORMATION: /replace="Asn"
<220> FEATURE:
<221> NAME/KEY: VARIANT
<222> LOCATION: (3)..(3)
<223> OTHER INFORMATION: /replace="Tyr"
<220> FEATURE:
<221> NAME/KEY: misc_feature
<222> LOCATION: (2)..(3)
<223> OTHER INFORMATION: /note="Residues given in the sequence have no
      preference with respect to those in the annotations for said
      position"

<400> SEQUENCE: 20

Trp Asp Arg
1

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Thr" or "Gly"
<220> FEATURE:
<221> NAME/KEY: VARIANT
<222> LOCATION: (2)..(2)
<223> OTHER INFORMATION: /replace="Ser" or "Asn"
<220> FEATURE:
<221> NAME/KEY: VARIANT
<222> LOCATION: (3)..(3)
<223> OTHER INFORMATION: /replace="Gly"
<220> FEATURE:
<221> NAME/KEY: VARIANT
<222> LOCATION: (4)..(4)
<223> OTHER INFORMATION: /replace="Ser" or "Val"
<220> FEATURE:
<221> NAME/KEY: VARIANT
<222> LOCATION: (5)..(5)
<223> OTHER INFORMATION: /replace="Ser" or "Trp"
<220> FEATURE:
<221> NAME/KEY: VARIANT
<222> LOCATION: (6)..(6)
<223> OTHER INFORMATION: /replace="Trp" or "Ala"
<220> FEATURE:
<221> NAME/KEY: VARIANT
<222> LOCATION: (7)..(7)
<223> OTHER INFORMATION: /replace="Phe" or "Met"
<220> FEATURE:
<221> NAME/KEY: VARIANT
<222> LOCATION: (8)..(8)
<223> OTHER INFORMATION: /replace="Pro" or "Asp"
<220> FEATURE:
<221> NAME/KEY: VARIANT
<222> LOCATION: (9)..(9)
<223> OTHER INFORMATION: /replace="Tyr"
<220> FEATURE:
<221> NAME/KEY: misc_feature
<222> LOCATION: (1)..(9)
<223> OTHER INFORMATION: /note="Residues given in the sequence have no
      preference with respect to those in the annotations for said
      position"

<400> SEQUENCE: 21

Glu Asp Tyr Gly Ile Ser Thr Tyr Ser
1               5

<210> SEQ ID NO 22
<211> LENGTH: 13
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Thr" or "Gly"
<220> FEATURE:
<221> NAME/KEY: VARIANT
<222> LOCATION: (2)..(2)
<223> OTHER INFORMATION: /replace="Ser" or "Asn"
<220> FEATURE:
<221> NAME/KEY: VARIANT
<222> LOCATION: (3)..(3)
<223> OTHER INFORMATION: /replace="Gly"
<220> FEATURE:
<221> NAME/KEY: VARIANT
<222> LOCATION: (4)..(4)
<223> OTHER INFORMATION: /replace="Ser" or "Val"
<220> FEATURE:
<221> NAME/KEY: VARIANT
<222> LOCATION: (5)..(5)
<223> OTHER INFORMATION: /replace="Ser" or "Trp"
<220> FEATURE:
<221> NAME/KEY: VARIANT
<222> LOCATION: (6)..(6)
<223> OTHER INFORMATION: /replace="Trp" or "Ala"
<220> FEATURE:
<221> NAME/KEY: VARIANT
<222> LOCATION: (7)..(7)
<223> OTHER INFORMATION: /replace="Phe" or "Met"
<220> FEATURE:
<221> NAME/KEY: VARIANT
<222> LOCATION: (8)..(8)
<223> OTHER INFORMATION: /replace="Pro" or "Asp"
<220> FEATURE:
<221> NAME/KEY: VARIANT
<222> LOCATION: (9)..(9)
<223> OTHER INFORMATION: /replace="Tyr"
<220> FEATURE:
<221> NAME/KEY: misc_feature
<222> LOCATION: (1)..(9)
<223> OTHER INFORMATION: /note="Residues given in the sequence have no
      preference with respect to those in the annotations for said
      position"

<400> SEQUENCE: 22

Glu Asp Tyr Gly Ile Ser Thr Tyr Ser Ala Met Asp Phe
1               5                   10

<210> SEQ ID NO 23
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Tyr Tyr Ile His
1               5

<210> SEQ ID NO 24
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24
```

```
Trp Ile Phe Pro Gly Ser Asp Ile Thr Lys Tyr Asn Glu Lys Phe Lys
1               5                   10                  15

Gly

<210> SEQ ID NO 25
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Glu Asp Tyr Gly Ile Ser Thr Tyr Ser Ala Met Asp Phe
1               5                   10

<210> SEQ ID NO 26
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asp Tyr Tyr Ile Tyr
1               5

<210> SEQ ID NO 27
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Tyr Ile Asp Pro Tyr Asn Gly Gly Thr Lys Tyr Asn Gln Lys Phe Lys
1               5                   10                  15

Asp

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Thr Ser Gly Ser Ser Trp Phe Pro Tyr
1               5

<210> SEQ ID NO 29
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Thr Tyr Leu Ile Glu
```

```
<210> SEQ ID NO 30
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Val Ile Asn Pro Gly Thr Gly Glu Thr Lys Tyr Asn Glu Asn Phe Arg
1               5                   10                  15

Ala

<210> SEQ ID NO 31
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Trp Asp Arg
1

<210> SEQ ID NO 32
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Thr Tyr Trp Met Asn
1               5

<210> SEQ ID NO 33
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Met Ile His Pro Ser Asp Ser Glu Ser Arg Leu Asn Gln Lys Phe Ile
1               5                   10                  15

Asp

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Asn Tyr Val Trp Ala Met Asp Tyr
1               5
```

```
<210> SEQ ID NO 35
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Asn Tyr Leu Ile Glu
1               5

<210> SEQ ID NO 36
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Val Ile Asn Pro Gly Ser Gly Asp Thr Lys Tyr Asn Glu Asn Phe Lys
1               5                   10                  15

Gly

<210> SEQ ID NO 37
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Trp Asn Tyr
1

<210> SEQ ID NO 38
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Arg"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      position"
<220> FEATURE:
<221> NAME/KEY: VARIANT
<222> LOCATION: (4)..(4)
<223> OTHER INFORMATION: /replace="Lys"
<220> FEATURE:
<221> NAME/KEY: VARIANT
<222> LOCATION: (5)..(5)
<223> OTHER INFORMATION: /replace="Ser" or "Asn"
<220> FEATURE:
```

```
<221> NAME/KEY: VARIANT
<222> LOCATION: (6)..(6)
<223> OTHER INFORMATION: /replace="Ile" or "Leu"
<220> FEATURE:
<221> NAME/KEY: VARIANT
<222> LOCATION: (7)..(7)
<223> OTHER INFORMATION: /replace="Ser" or "Val" or "Leu"
<220> FEATURE:
<221> NAME/KEY: VARIANT
<222> LOCATION: (8)..(8)
<223> OTHER INFORMATION: /replace="Asn" or "His"
<220> FEATURE:
<221> NAME/KEY: VARIANT
<222> LOCATION: (9)..(9)
<223> OTHER INFORMATION: /replace="Asn" or "Ser"
<220> FEATURE:
<221> NAME/KEY: VARIANT
<222> LOCATION: (10)..(10)
<223> OTHER INFORMATION: /replace="Leu" or "Asn" or "Gly"
<220> FEATURE:
<221> NAME/KEY: VARIANT
<222> LOCATION: (11)..(11)
<223> OTHER INFORMATION: /replace="His" or "Gly" or "Tyr"
<220> FEATURE:
<221> NAME/KEY: misc_feature
<222> LOCATION: (4)..(11)
<223> OTHER INFORMATION: /note="Residues given in the sequence have no
      preference with respect to those in the annotations for said
      position"

<400> SEQUENCE: 38

Lys Ala Ser Gln Asp Val Gly Thr Ala Val Ala
1               5                   10

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Arg"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      position"
<220> FEATURE:
<221> NAME/KEY: VARIANT
<222> LOCATION: (4)..(4)
<223> OTHER INFORMATION: /replace="Lys"
<220> FEATURE:
<221> NAME/KEY: VARIANT
<222> LOCATION: (5)..(5)
<223> OTHER INFORMATION: /replace="Ser" or "Asn"
<220> FEATURE:
<221> NAME/KEY: VARIANT
<222> LOCATION: (6)..(6)
<223> OTHER INFORMATION: /replace="Ile" or "Leu"
<220> FEATURE:
<221> NAME/KEY: VARIANT
<222> LOCATION: (7)..(7)
<223> OTHER INFORMATION: /replace="Ser" or "Val" or "Leu"
<220> FEATURE:
<221> NAME/KEY: VARIANT
<222> LOCATION: (8)..(8)
<223> OTHER INFORMATION: /replace="Asn" or "His"
<220> FEATURE:
<221> NAME/KEY: VARIANT
```

```
<222> LOCATION: (9)..(9)
<223> OTHER INFORMATION: /replace="Asn" or "Ser"
<220> FEATURE:
<221> NAME/KEY: VARIANT
<222> LOCATION: (10)..(10)
<223> OTHER INFORMATION: /replace="Leu" or "Asn" or "Gly"
<220> FEATURE:
<221> NAME/KEY: VARIANT
<222> LOCATION: (11)..(11)
<223> OTHER INFORMATION: /replace="His" or "Gly" or "Tyr"
<220> FEATURE:
<221> NAME/KEY: VARIANT
<222> LOCATION: (12)..(12)
<223> OTHER INFORMATION: /replace="Thr"
<220> FEATURE:
<221> NAME/KEY: VARIANT
<222> LOCATION: (13)..(13)
<223> OTHER INFORMATION: /replace="Tyr"
<220> FEATURE:
<221> NAME/KEY: VARIANT
<222> LOCATION: (14)..(14)
<223> OTHER INFORMATION: /replace="Met"
<220> FEATURE:
<221> NAME/KEY: VARIANT
<222> LOCATION: (15)..(15)
<223> OTHER INFORMATION: /replace="His"
<220> FEATURE:
<221> NAME/KEY: misc_feature
<222> LOCATION: (4)..(15)
<223> OTHER INFORMATION: /note="Residues given in the sequence have no
      preference with respect to those in the annotations for said
      position"

<400> SEQUENCE: 39

Lys Ala Ser Gln Asp Val Gly Thr Ala Val Ala Asn Thr Tyr Phe
1               5                   10                  15

<210> SEQ ID NO 40
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Arg"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      position"
<220> FEATURE:
<221> NAME/KEY: VARIANT
<222> LOCATION: (4)..(4)
<223> OTHER INFORMATION: /replace="Lys"
<220> FEATURE:
<221> NAME/KEY: VARIANT
<222> LOCATION: (5)..(5)
<223> OTHER INFORMATION: /replace="Ser" or "Asn"
<220> FEATURE:
<221> NAME/KEY: VARIANT
<222> LOCATION: (6)..(6)
<223> OTHER INFORMATION: /replace="Ile" or "Leu"
<220> FEATURE:
<221> NAME/KEY: VARIANT
<222> LOCATION: (7)..(7)
<223> OTHER INFORMATION: /replace="Ser" or "Val" or "Leu"
<220> FEATURE:
<221> NAME/KEY: VARIANT
<222> LOCATION: (8)..(8)
```

```
<223> OTHER INFORMATION: /replace="Asn" or "His"
<220> FEATURE:
<221> NAME/KEY: VARIANT
<222> LOCATION: (9)..(9)
<223> OTHER INFORMATION: /replace="Asn" or "Ser"
<220> FEATURE:
<221> NAME/KEY: VARIANT
<222> LOCATION: (10)..(10)
<223> OTHER INFORMATION: /replace="Leu" or "Asn" or "Gly"
<220> FEATURE:
<221> NAME/KEY: VARIANT
<222> LOCATION: (11)..(11)
<223> OTHER INFORMATION: /replace="His" or "Gly" or "Tyr"
<220> FEATURE:
<221> NAME/KEY: VARIANT
<222> LOCATION: (12)..(12)
<223> OTHER INFORMATION: /replace="Thr"
<220> FEATURE:
<221> NAME/KEY: VARIANT
<222> LOCATION: (13)..(13)
<223> OTHER INFORMATION: /replace="Tyr"
<220> FEATURE:
<221> NAME/KEY: VARIANT
<222> LOCATION: (14)..(14)
<223> OTHER INFORMATION: /replace="Met"
<220> FEATURE:
<221> NAME/KEY: VARIANT
<222> LOCATION: (15)..(15)
<223> OTHER INFORMATION: /replace="His"
<220> FEATURE:
<221> NAME/KEY: misc_feature
<222> LOCATION: (4)..(15)
<223> OTHER INFORMATION: /note="Residues given in the sequence have no
      preference with respect to those in the annotations for said
      position"

<400> SEQUENCE: 40

Lys Ala Ser Gln Asp Val Gly Thr Ala Val Ala Asn Thr Tyr Phe His
1               5                   10                  15

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Tyr" or "Lys" or "Ile"
<220> FEATURE:
<221> NAME/KEY: VARIANT
<222> LOCATION: (2)..(2)
<223> OTHER INFORMATION: /replace="Thr" or "Val"
<220> FEATURE:
<221> NAME/KEY: VARIANT
<222> LOCATION: (3)..(3)
<223> OTHER INFORMATION: /replace="Tyr"
<220> FEATURE:
<221> NAME/KEY: VARIANT
<222> LOCATION: (4)..(4)
<223> OTHER INFORMATION: /replace="Gln" or "Asn"
<220> FEATURE:
<221> NAME/KEY: VARIANT
<222> LOCATION: (5)..(5)
<223> OTHER INFORMATION: /replace="Ser" or "Leu"
<220> FEATURE:
<221> NAME/KEY: VARIANT
<222> LOCATION: (6)..(6)
<223> OTHER INFORMATION: /replace="Ile" or "Phe" or "Glu"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: misc_feature
```

```
<222> LOCATION: (1)..(7)
<223> OTHER INFORMATION: /note="Residues given in the sequence have no
      preference with respect to those in the annotations for said
      position"

<400> SEQUENCE: 41

Trp Ala Ser Thr Arg His Thr
1               5

<210> SEQ ID NO 42
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: VARIANT
<222> LOCATION: (2)..(2)
<223> OTHER INFORMATION: /replace="His"
<220> FEATURE:
<221> NAME/KEY: VARIANT
<222> LOCATION: (3)..(3)
<223> OTHER INFORMATION: /replace="Tyr"
<220> FEATURE:
<221> NAME/KEY: VARIANT
<222> LOCATION: (4)..(4)
<223> OTHER INFORMATION: /replace="Asn" or "Thr" or "Arg"
<220> FEATURE:
<221> NAME/KEY: VARIANT
<222> LOCATION: (5)..(5)
<223> OTHER INFORMATION: /replace="Arg" or "His" or "Glu"
<220> FEATURE:
<221> NAME/KEY: VARIANT
<222> LOCATION: (6)..(6)
<223> OTHER INFORMATION: /replace="Trp" or "Val" or "Leu"
<220> FEATURE:
<221> NAME/KEY: misc_feature
<222> LOCATION: (1)..(6)
<223> OTHER INFORMATION: /note="Residues given in the sequence have no
      preference with respect to those in the annotations for said
      position"
<220> FEATURE:
<221> NAME/KEY: VARIANT
<222> LOCATION: (8)..(8)
<223> OTHER INFORMATION: /replace="Tyr"
<220> FEATURE:
<221> NAME/KEY: misc_feature
<222> LOCATION: (8)..(8)
<223> OTHER INFORMATION: /note="Residue given in the sequence has no
      preference with respect to the annotation for said position"

<400> SEQUENCE: 42

Gln Gln Ser Ser Ser Tyr Pro Leu Thr
1               5

<210> SEQ ID NO 43
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Lys Ala Ser Gln Asp Val Gly Thr Ala Val Ala
1               5                   10
```

```
<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Trp Ala Ser Thr Arg His Thr
1               5

<210> SEQ ID NO 45
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gln Gln Tyr Ser Ser Tyr Pro Leu Thr
1               5

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Arg Ala Ser Gln Ser Ile Ser Asn Asn Leu His
1               5                   10

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Tyr Thr Tyr Gln Ser Ile Ser
1               5

<210> SEQ ID NO 48
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gln Gln Ser Asn Arg Trp Pro Leu Thr
1               5

<210> SEQ ID NO 49
<211> LENGTH: 16
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 49

Arg Ser Ser Gln Asn Leu Val His Ser Asn Gly Asn Thr Tyr Phe His
1               5                   10                  15

<210> SEQ ID NO 50
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Lys Val Ser Asn Arg Phe Ser
1               5

<210> SEQ ID NO 51
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser Gln Ser Thr His Val Pro Tyr Thr
1               5

<210> SEQ ID NO 52
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Arg Ala Ser Lys Ser Val Ser Thr Ser Gly Tyr Thr Tyr Met His
1               5                   10                  15

<210> SEQ ID NO 53
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ile Thr Ser Asn Leu Glu Ser
1               5

<210> SEQ ID NO 54
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54
```

```
Gln His Ser Arg Glu Leu Pro Tyr Thr
1               5
```

```
<210> SEQ ID NO 55
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Arg Ser Ser Gln Ser Leu Leu His Ser Asn Gly Asn Thr Tyr Phe His
1               5                   10                  15
```

```
<210> SEQ ID NO 56
<211> LENGTH: 122
<212> TYPE: PRT
<213> ORGANISM: Mus sp.

<400> SEQUENCE: 56

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Tyr Ile His Trp Val Lys Gln Arg Pro Gly Gln Gly Leu Glu Trp Ile
        35                  40                  45

Gly Trp Ile Phe Pro Gly Ser Asp Ile Thr Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Thr Val Tyr Phe Cys
                85                  90                  95

Thr Arg Glu Asp Tyr Gly Ile Ser Thr Tyr Ser Ala Met Asp Phe Trp
            100                 105                 110

Gly Gln Gly Thr Ser Val Thr Val Ser Ser
        115                 120
```

```
<210> SEQ ID NO 57
<211> LENGTH: 118
<212> TYPE: PRT
<213> ORGANISM: Mus sp.

<400> SEQUENCE: 57

Glu Ile Gln Leu Gln Gln Ser Gly Pro Asp Leu Val Lys Pro Gly Ala
1               5                   10                  15

Ser Val Lys Val Ser Cys Lys Ala Ser Gly Tyr Ser Phe Thr Asp Tyr
            20                  25                  30

Tyr Ile Tyr Trp Val Arg Gln Ser His Gly Lys Ser Leu Glu Trp Ile
        35                  40                  45

Gly Tyr Ile Asp Pro Tyr Asn Gly Gly Thr Lys Tyr Asn Gln Lys Phe
    50                  55                  60

Lys Asp Thr Ala Ser Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Thr Ser Gly Ser Ser Trp Phe Pro Tyr Trp Gly Gln Gly Thr
            100                 105                 110
```

Leu Val Thr Val Ser Ala
        115

<210> SEQ ID NO 58
<211> LENGTH: 112
<212> TYPE: PRT
<213> ORGANISM: Mus sp.

<400> SEQUENCE: 58

Gln Val Gln Leu Gln Gln Ser Gly Ala Glu Leu Val Arg Pro Gly Thr
1               5                   10                  15

Ser Val Arg Val Ser Cys Lys Ala Ser Gly Tyr Ala Phe Thr Asn Tyr
            20                  25                  30

Leu Ile Glu Trp Ile Lys Gln Arg Pro Gly Gln Gly Leu Glu Trp Ile
        35                  40                  45

Gly Val Ile Asn Pro Gly Ser Gly Asp Thr Lys Tyr Asn Glu Asn Phe
    50                  55                  60

Lys Gly Lys Ala Thr Leu Thr Ala Asp Ile Ser Ser Thr Ala Tyr
65                  70                  75                  80

Leu Gln Leu Ser Ser Leu Thr Ser Asp Asp Ser Ala Val Tyr Phe Cys
                85                  90                  95

Ala Gly Trp Asn Tyr Trp Gly Gln Gly Thr Thr Leu Thr Val Ser Ser
            100                 105                 110

<210> SEQ ID NO 59
<211> LENGTH: 112
<212> TYPE: PRT
<213> ORGANISM: Mus sp.

<400> SEQUENCE: 59

Gln Val Gln Leu Gln Gln Ser Gly Ala Glu Leu Val Arg Pro Gly Thr
1               5                   10                  15

Ser Val Gln Val Ser Cys Lys Ala Ser Gly Tyr Ser Phe Thr Thr Tyr
            20                  25                  30

Leu Ile Glu Trp Ile Lys Gln Arg Pro Gly Gln Gly Leu Glu Trp Ile
        35                  40                  45

Gly Val Ile Asn Pro Gly Thr Gly Glu Thr Lys Tyr Asn Glu Asn Phe
    50                  55                  60

Arg Ala Lys Ala Ile Met Thr Ala Asp Lys Tyr Ser Ser Thr Ala Tyr
65                  70                  75                  80

Met Gln Leu Ser Ser Leu Thr Ala Asp Asp Ser Ala Val Tyr Phe Cys
                85                  90                  95

Ala Arg Trp Asp Arg Trp Gly Gln Gly Thr Thr Leu Thr Val Ser Ser
            100                 105                 110

<210> SEQ ID NO 60
<211> LENGTH: 118
<212> TYPE: PRT
<213> ORGANISM: Mus sp.

<400> SEQUENCE: 60

Gln Val Gln Leu Gln Pro Gly Ala Glu Leu Val Arg Pro Gly Thr
1               5                   10                  15

Ser Val Lys Leu Ser Cys Lys Ala Ser Gly Tyr Ser Phe Thr Thr Tyr
            20                  25                  30

Trp Met Asn Trp Val Lys Gln Arg Pro Gly Gln Asp Leu Glu Trp Ile
        35                  40                  45

Gly Met Ile His Pro Ser Asp Ser Glu Ser Arg Leu Asn Gln Lys Phe
    50                  55                  60

```
Ile Asp Lys Ala Thr Leu Ser Ala Asp Lys Ser Ser Thr Ala Tyr
 65                  70                  75                  80

Met Leu Leu Asn Ser Pro Thr Ser Glu Asp Ser Ala Val Tyr Tyr Cys
                 85                  90                  95

Ala Phe Gly Asn Tyr Val Trp Ala Met Asp Tyr Trp Gly Gln Gly Thr
            100                 105                 110

Ser Val Thr Val Ser Ser
        115

<210> SEQ ID NO 61
<211> LENGTH: 108
<212> TYPE: PRT
<213> ORGANISM: Mus sp.

<400> SEQUENCE: 61

Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Gly Thr Ala
                 20                  25                  30

Val Ala Trp Tyr Gln Gln Lys Pro Gly Gln Ser Pro Lys Leu Leu Ile
             35                  40                  45

Tyr Trp Ala Ser Thr Arg His Thr Gly Val Pro Asp Arg Phe Thr Gly
 50                  55                  60

Ser Gly Ser Gly Pro Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Leu
                 85                  90                  95

Thr Phe Gly Ser Gly Thr Lys Leu Glu Ile Lys Arg
            100                 105

<210> SEQ ID NO 62
<211> LENGTH: 108
<212> TYPE: PRT
<213> ORGANISM: Mus sp.

<400> SEQUENCE: 62

Asp Ile Val Leu Thr Gln Ser Pro Ala Thr Leu Ser Val Thr Pro Gly
  1               5                  10                  15

Asp Ser Val Ser Leu Ser Cys Arg Ala Ser Gln Ser Ile Ser Asn Asn
                 20                  25                  30

Leu His Trp Tyr Gln Gln Lys Ser His Glu Ser Pro Arg Leu Leu Ile
             35                  40                  45

Lys Tyr Thr Tyr Gln Ser Ile Ser Gly Ile Pro Ser Arg Phe Ser Gly
 50                  55                  60

Ser Gly Ser Gly Thr Asp Phe Thr Leu Thr Ile Asn Ser Val Glu Thr
 65                  70                  75                  80

Glu Asp Phe Gly Met Tyr Phe Cys Gln Gln Ser Asn Arg Trp Pro Leu
                 85                  90                  95

Thr Phe Gly Ala Gly Thr Lys Leu Glu Leu Lys Arg
            100                 105

<210> SEQ ID NO 63
<211> LENGTH: 113
<212> TYPE: PRT
<213> ORGANISM: Mus sp.

<400> SEQUENCE: 63

Asp Val Val Met Thr Gln Thr Pro Leu Ser Leu Pro Val Ser Leu Gly
```

```
                1               5                  10                 15
Asp Gln Ala Ser Ile Ser Cys Arg Ser Ser Gln Ser Leu Leu His Ser
                20                 25                 30

Asn Gly Asn Thr Tyr Phe His Trp Tyr Leu Gln Lys Pro Gly Gln Ser
            35                 40                 45

Pro Glu Leu Leu Ile Tyr Lys Val Ser Asn Arg Phe Ser Gly Val Pro
        50                 55                 60

Asp Arg Phe Ser Gly Ser Gly Ser Gly Thr Asp Phe Thr Leu Lys Ile
65                 70                 75                 80

Ser Arg Val Glu Ala Glu Asp Leu Gly Val Tyr Phe Cys Ser Gln Ser
                85                 90                 95

Thr His Val Pro Tyr Thr Phe Gly Gly Gly Thr Lys Leu Glu Ile Lys
            100                105                110

Arg

<210> SEQ ID NO 64
<211> LENGTH: 113
<212> TYPE: PRT
<213> ORGANISM: Mus sp.

<400> SEQUENCE: 64

Asp Val Val Met Thr Gln Ala Pro Leu Ser Leu Pro Val Ser Leu Gly
1               5                  10                 15

Asp Gln Val Ser Ile Ser Cys Arg Ser Ser Gln Asn Leu Val His Ser
                20                 25                 30

Asn Gly Asn Thr Tyr Phe His Trp Tyr Leu Gln Lys Pro Gly Gln Ser
            35                 40                 45

Pro Glu Leu Leu Ile Tyr Lys Val Ser Asn Arg Phe Ser Gly Val Pro
        50                 55                 60

Asp Arg Phe Ser Gly Ser Gly Ser Gly Thr Asp Phe Thr Leu Lys Ile
65                 70                 75                 80

Ser Arg Val Glu Ala Glu Asp Leu Gly Val Tyr Phe Cys Ser Gln Ser
                85                 90                 95

Thr His Val Pro Tyr Thr Phe Gly Gly Gly Thr Lys Leu Glu Ile Lys
            100                105                110

Arg

<210> SEQ ID NO 65
<211> LENGTH: 112
<212> TYPE: PRT
<213> ORGANISM: Mus sp.

<400> SEQUENCE: 65

Asp Ile Val Leu Thr Gln Ser Pro Ala Ser Leu Val Val Ser Leu Gly
1               5                  10                 15

Gln Arg Ala Thr Ile Ser Cys Arg Ala Ser Lys Ser Val Ser Thr Ser
                20                 25                 30

Gly Tyr Thr Tyr Met His Trp Tyr Gln Gln Lys Pro Gly Gln Pro Pro
            35                 40                 45

Lys Leu Leu Ile Tyr Ile Thr Ser Asn Leu Glu Ser Gly Val Pro Ala
        50                 55                 60

Arg Phe Ser Gly Ser Gly Ser Gly Thr Asp Phe Thr Leu Asn Ile His
65                 70                 75                 80

Pro Val Glu Glu Glu Asp Ala Ala Thr Tyr Tyr Cys Gln His Ser Arg
                85                 90                 95

Glu Leu Pro Tyr Thr Phe Gly Gly Gly Thr Lys Leu Glu Ile Lys Arg
```

-continued

<210> SEQ ID NO 66
<211> LENGTH: 98
<212> TYPE: PRT
<213> ORGANISM: Homo sapiens

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 67
<211> LENGTH: 117
<212> TYPE: PRT
<213> ORGANISM: Homo sapiens

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Arg Gln Ala Pro Gly Gln Gly Leu Glu Trp Ile
        35                  40                  45

Gly Tyr Ile Asp Pro Tyr Asn Gly Asp Thr Phe Tyr Asn Gln Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Asn Tyr Gly Ser Phe Ala Tyr Trp Gly Gln Gly Thr Leu
            100                 105                 110

Val Thr Val Ser Ser
        115

<210> SEQ ID NO 68
<211> LENGTH: 95
<212> TYPE: PRT
<213> ORGANISM: Homo sapiens

<400> SEQUENCE: 68

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly

```
                    50                  55                  60
Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro
                 85                  90                  95

<210> SEQ ID NO 69
<211> LENGTH: 120
<212> TYPE: PRT
<213> ORGANISM: Mus sp.

<400> SEQUENCE: 69

Gln Val Gln Leu Gln Gln Ser Gly Pro Glu Leu Val Lys Pro Gly Ala
 1               5                   10                  15

Ser Val Lys Ile Ser Cys Lys Ala Ser Gly Tyr Ser Phe Thr Ser Tyr
                 20                  25                  30

Tyr Ile His Trp Val Lys Gln Arg Pro Gly Gln Gly Leu Glu Trp Ile
             35                  40                  45

Gly Trp Ile Phe Pro Gly Ser Asp Ile Thr Lys Tyr Asn Glu Lys Phe
         50                  55                  60

Lys Gly Lys Ala Thr Leu Thr Ala Asp Thr Ser Ser Ser Thr Ala Tyr
 65                  70                  75                  80

Met Gln Leu Ser Ser Leu Thr Ser Glu Asp Ser Thr Val Tyr Phe Cys
                 85                  90                  95

Thr Arg Glu Asp Tyr Gly Ile Ser Thr Tyr Ser Ala Met Asp Phe Trp
                100                 105                 110

Gly Gln Gly Thr Ser Val Thr Val
            115                 120

<210> SEQ ID NO 70
<211> LENGTH: 110
<212> TYPE: PRT
<213> ORGANISM: Mus sp.

<400> SEQUENCE: 70

Gln Val Gln Leu Gln Gln Ser Gly Ala Glu Leu Val Arg Pro Gly Thr
 1               5                   10                  15

Ser Val Arg Val Ser Cys Lys Ala Ser Gly Tyr Ala Phe Thr Asn Tyr
                 20                  25                  30

Leu Ile Glu Trp Ile Lys Gln Arg Pro Gly Gln Gly Leu Glu Trp Ile
             35                  40                  45

Gly Val Ile Asn Pro Gly Ser Gly Asp Thr Lys Tyr Asn Glu Asn Phe
         50                  55                  60

Lys Gly Lys Ala Thr Leu Thr Ala Asp Ile Ser Ser Ser Thr Ala Tyr
 65                  70                  75                  80

Leu Gln Leu Ser Ser Leu Thr Ser Asp Asp Ser Ala Val Tyr Phe Cys
                 85                  90                  95

Ala Gly Trp Asn Tyr Trp Gly Gln Gly Thr Thr Leu Thr Val
                100                 105                 110

<210> SEQ ID NO 71
<211> LENGTH: 110
<212> TYPE: PRT
<213> ORGANISM: Mus sp.

<400> SEQUENCE: 71

Gln Val Gln Leu Gln Gln Ser Gly Ala Glu Leu Val Arg Pro Gly Thr
 1               5                   10                  15
```

-continued

Ser Val Gln Val Ser Cys Lys Ala Ser Gly Tyr Ser Phe Thr Thr Tyr
            20                  25                  30

Leu Ile Glu Trp Ile Lys Gln Arg Pro Gly Gln Gly Leu Glu Trp Ile
         35                  40                  45

Gly Val Ile Asn Pro Gly Thr Gly Glu Thr Lys Tyr Asn Glu Asn Phe
 50                  55                  60

Arg Ala Lys Ala Ile Met Thr Ala Asp Lys Tyr Ser Ser Thr Ala Tyr
 65                  70                  75                  80

Met Gln Leu Ser Ser Leu Thr Ala Asp Asp Ser Ala Val Tyr Phe Cys
                 85                  90                  95

Ala Arg Trp Asp Arg Trp Gly Gln Gly Thr Thr Leu Thr Val
                100                 105                 110

<210> SEQ ID NO 72
<211> LENGTH: 116
<212> TYPE: PRT
<213> ORGANISM: Mus sp.

<400> SEQUENCE: 72

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Ser Phe Thr Thr Tyr
            20                  25                  30

Trp Met Asn Trp Val Lys Gln Arg Pro Gly Gln Asp Leu Glu Trp Ile
         35                  40                  45

Gly Met Ile His Pro Ser Asp Ser Glu Ser Arg Leu Asn Gln Lys Phe
 50                  55                  60

Ile Asp Lys Ala Thr Leu Ser Ala Asp Lys Ser Ser Ser Thr Ala Tyr
 65                  70                  75                  80

Met Leu Leu Asn Ser Pro Thr Ser Glu Asp Ser Ala Val Tyr Tyr Cys
                 85                  90                  95

Ala Phe Gly Asn Tyr Val Trp Ala Met Asp Tyr Trp Gly Gln Gly Thr
                100                 105                 110

Ser Val Thr Val
        115

<210> SEQ ID NO 73
<211> LENGTH: 98
<212> TYPE: PRT
<213> ORGANISM: Homo sapiens

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
         35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 74

```
<211> LENGTH: 98
<212> TYPE: PRT
<213> ORGANISM: Homo sapiens

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 75
<211> LENGTH: 95
<212> TYPE: PRT
<213> ORGANISM: Homo sapiens

<400> SEQUENCE: 75

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95

<210> SEQ ID NO 76
<211> LENGTH: 95
<212> TYPE: PRT
<213> ORGANISM: Homo sapiens

<400> SEQUENCE: 76

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95

<210> SEQ ID NO 77
```

<211> LENGTH: 95
<212> TYPE: PRT
<213> ORGANISM: Homo sapiens

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 78
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: misc_feature
<222> LOCATION: (1)..(4)
<223> OTHER INFORMATION: /note="Residues given in the sequence have no
      preference with respect to those in the annotations for said
      position"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: misc_feature
<222> LOCATION: (7)..(7)
<223> OTHER INFORMATION: /note="Residue given in the sequence has no
      preference with respect to the annotation for said position"
<220> FEATURE:
<221> NAME/KEY: VARIANT
<222> LOCATION: (9)..(9)
<223> OTHER INFORMATION: /replace="Asp" or "Ala" or "Leu"
<220> FEATURE:
<221> NAME/KEY: VARIANT
<222> LOCATION: (10)..(10)
<223> OTHER INFORMATION: /replace="Thr" or "Phe"
<220> FEATURE:
<221> NAME/KEY: VARIANT
<222> LOCATION: (11)..(11)
<223> OTHER INFORMATION: /replace="Gln"
<220> FEATURE:
<221> NAME/KEY: VARIANT
<222> LOCATION: (12)..(12)
<223> OTHER INFORMATION: /replace="Ser" or "Pro"

```
<220> FEATURE:
<221> NAME/KEY: VARIANT
<222> LOCATION: (13)..(13)
<223> OTHER INFORMATION: /replace="Ala"
<220> FEATURE:
<221> NAME/KEY: VARIANT
<222> LOCATION: (14)..(14)
<223> OTHER INFORMATION: /replace="Thr"
<220> FEATURE:
<221> NAME/KEY: VARIANT
<222> LOCATION: (15)..(15)
<223> OTHER INFORMATION: /replace="Leu" or "Val"
<220> FEATURE:
<221> NAME/KEY: VARIANT
<222> LOCATION: (16)..(16)
<223> OTHER INFORMATION: /replace="Lys"
<220> FEATURE:
<221> NAME/KEY: VARIANT
<222> LOCATION: (17)..(17)
<223> OTHER INFORMATION: /replace="Gln" or "Asp"
<220> FEATURE:
<221> NAME/KEY: VARIANT
<222> LOCATION: (18)..(18)
<223> OTHER INFORMATION: /replace="Lys" or "Pro"
<220> FEATURE:
<221> NAME/KEY: VARIANT
<222> LOCATION: (19)..(19)
<223> OTHER INFORMATION: /replace="Val"
<220> FEATURE:
<221> NAME/KEY: VARIANT
<222> LOCATION: (20)..(20)
<223> OTHER INFORMATION: /replace="Ser"
<220> FEATURE:
<221> NAME/KEY: VARIANT
<222> LOCATION: (21)..(21)
<223> OTHER INFORMATION: /replace="Leu"
<220> FEATURE:
<221> NAME/KEY: VARIANT
<222> LOCATION: (22)..(22)
<223> OTHER INFORMATION: /replace="Thr" or "Asn"
<220> FEATURE:
<221> NAME/KEY: misc_feature
<222> LOCATION: (9)..(22)
<223> OTHER INFORMATION: /note="Residues given in the sequence have no
      preference with respect to those in the annotations for said
      position"
<220> FEATURE:
<221> NAME/KEY: VARIANT
<222> LOCATION: (24)..(24)
<223> OTHER INFORMATION: /replace="Arg"
<220> FEATURE:
<221> NAME/KEY: VARIANT
<222> LOCATION: (25)..(25)
<223> OTHER INFORMATION: /replace="Ser"
<220> FEATURE:
<221> NAME/KEY: misc_feature
<222> LOCATION: (24)..(25)
<223> OTHER INFORMATION: /note="Residues given in the sequence have no
      preference with respect to those in the annotations for said
      position"
<220> FEATURE:
<221> NAME/KEY: VARIANT
<222> LOCATION: (27)..(27)
<223> OTHER INFORMATION: /replace="Lys"
<220> FEATURE:
<221> NAME/KEY: VARIANT
<222> LOCATION: (28)..(28)
<223> OTHER INFORMATION: /replace="Ser" or "Asn"
<220> FEATURE:
<221> NAME/KEY: VARIANT
<222> LOCATION: (29)..(29)
<223> OTHER INFORMATION: /replace="Ile" or "Leu"
<220> FEATURE:
<221> NAME/KEY: VARIANT
<222> LOCATION: (30)..(30)
<223> OTHER INFORMATION: /replace="Ser" or "Val" or "Leu"
<220> FEATURE:
<221> NAME/KEY: VARIANT
<222> LOCATION: (31)..(31)
<223> OTHER INFORMATION: /replace="Asn" or "His"
```

```
<220> FEATURE:
<221> NAME/KEY: VARIANT
<222> LOCATION: (32)..(32)
<223> OTHER INFORMATION: /replace="Asn" or "Ser"
<220> FEATURE:
<221> NAME/KEY: VARIANT
<222> LOCATION: (33)..(33)
<223> OTHER INFORMATION: /replace="Leu" or "Asn" or "Gly"
<220> FEATURE:
<221> NAME/KEY: VARIANT
<222> LOCATION: (34)..(34)
<223> OTHER INFORMATION: /replace="His" or "Gly" or "Tyr"
<220> FEATURE:
<221> NAME/KEY: VARIANT
<222> LOCATION: (35)..(35)
<223> OTHER INFORMATION: /replace="Thr"
<220> FEATURE:
<221> NAME/KEY: VARIANT
<222> LOCATION: (36)..(36)
<223> OTHER INFORMATION: /replace="Tyr"
<220> FEATURE:
<221> NAME/KEY: VARIANT
<222> LOCATION: (37)..(37)
<223> OTHER INFORMATION: /replace="Met"
<220> FEATURE:
<221> NAME/KEY: VARIANT
<222> LOCATION: (38)..(38)
<223> OTHER INFORMATION: /replace="His"
<220> FEATURE:
<221> NAME/KEY: misc_feature
<222> LOCATION: (27)..(38)
<223> OTHER INFORMATION: /note="Residues given in the sequence have no
      preference with respect to those in the annotations for said
      position"
<220> FEATURE:
<221> NAME/KEY: VARIANT
<222> LOCATION: (40)..(40)
<223> OTHER INFORMATION: /replace="Tyr"
<220> FEATURE:
<221> NAME/KEY: VARIANT
<222> LOCATION: (41)..(41)
<223> OTHER INFORMATION: /replace="Leu"
<220> FEATURE:
<221> NAME/KEY: misc_feature
<222> LOCATION: (40)..(41)
<223> OTHER INFORMATION: /note="Residues given in the sequence have no
      preference with respect to those in the annotations for said
      position"
<220> FEATURE:
<221> NAME/KEY: VARIANT
<222> LOCATION: (43)..(43)
<223> OTHER INFORMATION: /replace="Arg"
<220> FEATURE:
<221> NAME/KEY: misc_feature
<222> LOCATION: (43)..(43)
<223> OTHER INFORMATION: /note="Residue given in the sequence has no
      preference with respect to the annotation for said position"
<220> FEATURE:
<221> NAME/KEY: VARIANT
<222> LOCATION: (45)..(45)
<223> OTHER INFORMATION: /replace="Asp"
<220> FEATURE:
<221> NAME/KEY: VARIANT
<222> LOCATION: (46)..(46)
<223> OTHER INFORMATION: /replace="Lys"
<220> FEATURE:
<221> NAME/KEY: VARIANT
<222> LOCATION: (47)..(47)
<223> OTHER INFORMATION: /replace="Ser" or "Pro"
<220> FEATURE:
<221> NAME/KEY: misc_feature
<222> LOCATION: (45)..(47)
<223> OTHER INFORMATION: /note="Residues given in the sequence have no
      preference with respect to those in the annotations for said
      position"
<220> FEATURE:
<221> NAME/KEY: VARIANT
<222> LOCATION: (49)..(49)
<223> OTHER INFORMATION: /replace="Arg" or "Gln"
<220> FEATURE:
```

```
<221> NAME/KEY: VARIANT
<222> LOCATION: (50)..(50)
<223> OTHER INFORMATION: /replace="Arg"
<220> FEATURE:
<221> NAME/KEY: misc_feature
<222> LOCATION: (49)..(50)
<223> OTHER INFORMATION: /note="Residues given in the sequence have no
      preference with respect to those in the annotations for said
      position"
<220> FEATURE:
<221> NAME/KEY: VARIANT
<222> LOCATION: (53)..(53)
<223> OTHER INFORMATION: /replace="Lys"
<220> FEATURE:
<221> NAME/KEY: VARIANT
<222> LOCATION: (54)..(54)
<223> OTHER INFORMATION: /replace="Tyr" or "Lys" or "Ile"
<220> FEATURE:
<221> NAME/KEY: VARIANT
<222> LOCATION: (55)..(55)
<223> OTHER INFORMATION: /replace="Thr" or "Val"
<220> FEATURE:
<221> NAME/KEY: VARIANT
<222> LOCATION: (56)..(56)
<223> OTHER INFORMATION: /replace="Tyr"
<220> FEATURE:
<221> NAME/KEY: VARIANT
<222> LOCATION: (57)..(57)
<223> OTHER INFORMATION: /replace="Gln" or "Asn"
<220> FEATURE:
<221> NAME/KEY: VARIANT
<222> LOCATION: (58)..(58)
<223> OTHER INFORMATION: /replace="Ser" or "Leu"
<220> FEATURE:
<221> NAME/KEY: VARIANT
<222> LOCATION: (59)..(59)
<223> OTHER INFORMATION: /replace="Ile" or "Phe" or "Glu"
<220> FEATURE:
<221> NAME/KEY: VARIANT
<222> LOCATION: (60)..(60)
<223> OTHER INFORMATION: /replace="Ser"
<220> FEATURE:
<221> NAME/KEY: misc_feature
<222> LOCATION: (53)..(60)
<223> OTHER INFORMATION: /note="Residues given in the sequence have no
      preference with respect to those in the annotations for said
      position"
<220> FEATURE:
<221> NAME/KEY: VARIANT
<222> LOCATION: (62)..(62)
<223> OTHER INFORMATION: /replace="Ile"
<220> FEATURE:
<221> NAME/KEY: misc_feature
<222> LOCATION: (62)..(62)
<223> OTHER INFORMATION: /note="Residue given in the sequence has no
      preference with respect to the annotation for said position"
<220> FEATURE:
<221> NAME/KEY: VARIANT
<222> LOCATION: (64)..(64)
<223> OTHER INFORMATION: /replace="Ala" or "Asp"
<220> FEATURE:
<221> NAME/KEY: misc_feature
<222> LOCATION: (64)..(64)
<223> OTHER INFORMATION: /note="Residue given in the sequence has no
      preference with respect to those in the annotations for said
      position"
<220> FEATURE:
<221> NAME/KEY: VARIANT
<222> LOCATION: (74)..(74)
<223> OTHER INFORMATION: /replace="Glu"
<220> FEATURE:
<221> NAME/KEY: misc_feature
<222> LOCATION: (74)..(74)
<223> OTHER INFORMATION: /note="Residue given in the sequence has no
      preference with respect to the annotation for said position"
<220> FEATURE:
<221> NAME/KEY: VARIANT
<222> LOCATION: (78)..(78)
<223> OTHER INFORMATION: /replace="Thr"
<220> FEATURE:
```

-continued

```
<221> NAME/KEY: misc_feature
<222> LOCATION: (78)..(78)
<223> OTHER INFORMATION: /note="Residue given in the sequence has no
      preference with respect to the annotation for said position"
<220> FEATURE:
<221> NAME/KEY: VARIANT
<222> LOCATION: (80)..(80)
<223> OTHER INFORMATION: /replace="Asn"
<220> FEATURE:
<221> NAME/KEY: VARIANT
<222> LOCATION: (81)..(81)
<223> OTHER INFORMATION: /replace="Arg"
<220> FEATURE:
<221> NAME/KEY: VARIANT
<222> LOCATION: (82)..(82)
<223> OTHER INFORMATION: /replace="Leu"
<220> FEATURE:
<221> NAME/KEY: VARIANT
<222> LOCATION: (83)..(83)
<223> OTHER INFORMATION: /replace="Glu"
<220> FEATURE:
<221> NAME/KEY: VARIANT
<222> LOCATION: (84)..(84)
<223> OTHER INFORMATION: /replace="Ala" or "Ser"
<220> FEATURE:
<221> NAME/KEY: misc_feature
<222> LOCATION: (80)..(84)
<223> OTHER INFORMATION: /note="Residues given in the sequence have no
      preference with respect to those in the annotations for said
      position"
<220> FEATURE:
<221> NAME/KEY: VARIANT
<222> LOCATION: (87)..(87)
<223> OTHER INFORMATION: /replace="Ala" or "Val"
<220> FEATURE:
<221> NAME/KEY: VARIANT
<222> LOCATION: (88)..(88)
<223> OTHER INFORMATION: /replace="Gly"
<220> FEATURE:
<221> NAME/KEY: VARIANT
<222> LOCATION: (89)..(89)
<223> OTHER INFORMATION: /replace="Val"
<220> FEATURE:
<221> NAME/KEY: misc_feature
<222> LOCATION: (87)..(89)
<223> OTHER INFORMATION: /note="Residues given in the sequence have no
      preference with respect to those in the annotations for said
      position"
<220> FEATURE:
<221> NAME/KEY: VARIANT
<222> LOCATION: (93)..(93)
<223> OTHER INFORMATION: /replace="Ser"
<220> FEATURE:
<221> NAME/KEY: VARIANT
<222> LOCATION: (94)..(94)
<223> OTHER INFORMATION: /replace="His"
<220> FEATURE:
<221> NAME/KEY: VARIANT
<222> LOCATION: (95)..(95)
<223> OTHER INFORMATION: /replace="Tyr"
<220> FEATURE:
<221> NAME/KEY: VARIANT
<222> LOCATION: (96)..(96)
<223> OTHER INFORMATION: /replace="Asn" or "Thr" or "Arg"
<220> FEATURE:
<221> NAME/KEY: VARIANT
<222> LOCATION: (97)..(97)
<223> OTHER INFORMATION: /replace="Arg" or "His" or "Glu"
<220> FEATURE:
<221> NAME/KEY: VARIANT
<222> LOCATION: (98)..(98)
<223> OTHER INFORMATION: /replace="Trp" or "Val" or "Leu"
<220> FEATURE:
<221> NAME/KEY: misc_feature
<222> LOCATION: (93)..(98)
<223> OTHER INFORMATION: /note="Residues given in the sequence have no
      preference with respect to those in the annotations for said
      position"
<220> FEATURE:
<221> NAME/KEY: VARIANT
```

-continued

```
<222> LOCATION: (100)..(100)
<223> OTHER INFORMATION: /replace="Tyr"
<220> FEATURE:
<221> NAME/KEY: misc_feature
<222> LOCATION: (100)..(100)
<223> OTHER INFORMATION: /note="Residue given in the sequence has no
      preference with respect to the annotation for said position"
<220> FEATURE:
<221> NAME/KEY: VARIANT
<222> LOCATION: (107)..(107)
<223> OTHER INFORMATION: /replace="Lys"
<220> FEATURE:
<221> NAME/KEY: misc_feature
<222> LOCATION: (107)..(107)
<223> OTHER INFORMATION: /note="Residue given in the sequence has no
      preference with respect to the annotation for said position"

<400> SEQUENCE: 78

Asp Ile Val Met Thr Gln Ser Pro Ser Ser Leu Ala Val Ser Pro Gly
1               5                   10                  15

Glu Arg Ala Thr Ile Ser Cys Lys Ala Ser Gln Asp Val Gly Thr Ala
            20                  25                  30

Val Ala Asn Thr Tyr Phe Trp Phe Gln Gln Lys Pro Gly Gln Ala Pro
        35                  40                  45

Lys Leu Leu Ile Tyr Trp Ala Ser Thr Arg His Thr Gly Val Pro Ser
50                  55                  60

Arg Phe Ser Gly Ser Gly Ser Gly Thr Asp Phe Thr Leu Lys Ile Ser
65                  70                  75                  80

Ser Val Gln Pro Glu Asp Phe Ala Thr Tyr Tyr Cys Gln Gln Ser Ser
                85                  90                  95

Ser Tyr Pro Leu Thr Phe Gly Gln Gly Thr Arg Val Glu Ile Lys Arg
            100                 105                 110

<210> SEQ ID NO 79
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: misc_feature
<222> LOCATION: (1)..(4)
<223> OTHER INFORMATION: /note="Residues given in the sequence have no
      preference with respect to those in the annotations for said
      position"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: misc_feature
<222> LOCATION: (7)..(7)
<223> OTHER INFORMATION: /note="Residue given in the sequence has no
      preference with respect to the annotation for said position"
```

```
<220> FEATURE:
<221> NAME/KEY: VARIANT
<222> LOCATION: (9)..(9)
<223> OTHER INFORMATION: /replace="Asp" or "Ala" or "Leu"
<220> FEATURE:
<221> NAME/KEY: VARIANT
<222> LOCATION: (10)..(10)
<223> OTHER INFORMATION: /replace="Thr" or "Phe"
<220> FEATURE:
<221> NAME/KEY: VARIANT
<222> LOCATION: (11)..(11)
<223> OTHER INFORMATION: /replace="Gln"
<220> FEATURE:
<221> NAME/KEY: VARIANT
<222> LOCATION: (12)..(12)
<223> OTHER INFORMATION: /replace="Ser" or "Pro"
<220> FEATURE:
<221> NAME/KEY: VARIANT
<222> LOCATION: (13)..(13)
<223> OTHER INFORMATION: /replace="Ala"
<220> FEATURE:
<221> NAME/KEY: VARIANT
<222> LOCATION: (14)..(14)
<223> OTHER INFORMATION: /replace="Thr"
<220> FEATURE:
<221> NAME/KEY: VARIANT
<222> LOCATION: (15)..(15)
<223> OTHER INFORMATION: /replace="Leu" or "Val"
<220> FEATURE:
<221> NAME/KEY: VARIANT
<222> LOCATION: (16)..(16)
<223> OTHER INFORMATION: /replace="Lys"
<220> FEATURE:
<221> NAME/KEY: VARIANT
<222> LOCATION: (17)..(17)
<223> OTHER INFORMATION: /replace="Gln" or "Asp"
<220> FEATURE:
<221> NAME/KEY: VARIANT
<222> LOCATION: (18)..(18)
<223> OTHER INFORMATION: /replace="Lys" or "Pro"
<220> FEATURE:
<221> NAME/KEY: VARIANT
<222> LOCATION: (19)..(19)
<223> OTHER INFORMATION: /replace="Val"
<220> FEATURE:
<221> NAME/KEY: VARIANT
<222> LOCATION: (20)..(20)
<223> OTHER INFORMATION: /replace="Ser"
<220> FEATURE:
<221> NAME/KEY: VARIANT
<222> LOCATION: (21)..(21)
<223> OTHER INFORMATION: /replace="Leu"
<220> FEATURE:
<221> NAME/KEY: VARIANT
<222> LOCATION: (22)..(22)
<223> OTHER INFORMATION: /replace="Thr" or "Asn"
<220> FEATURE:
<221> NAME/KEY: misc_feature
<222> LOCATION: (9)..(22)
<223> OTHER INFORMATION: /note="Residues given in the sequence have no
      preference with respect to those in the annotations for said
      position"
<220> FEATURE:
<221> NAME/KEY: VARIANT
<222> LOCATION: (24)..(24)
<223> OTHER INFORMATION: /replace="Arg"
<220> FEATURE:
<221> NAME/KEY: VARIANT
<222> LOCATION: (25)..(25)
<223> OTHER INFORMATION: /replace="Ser"
<220> FEATURE:
<221> NAME/KEY: misc_feature
<222> LOCATION: (24)..(25)
<223> OTHER INFORMATION: /note="Residues given in the sequence have no
      preference with respect to those in the annotations for said
      position"
<220> FEATURE:
<221> NAME/KEY: VARIANT
<222> LOCATION: (27)..(27)
<223> OTHER INFORMATION: /replace="Lys"
```

```
-continued

<220> FEATURE:
<221> NAME/KEY: VARIANT
<222> LOCATION: (28)..(28)
<223> OTHER INFORMATION: /replace="Ser" or "Asn"
<220> FEATURE:
<221> NAME/KEY: VARIANT
<222> LOCATION: (29)..(29)
<223> OTHER INFORMATION: /replace="Ile" or "Leu"
<220> FEATURE:
<221> NAME/KEY: VARIANT
<222> LOCATION: (30)..(30)
<223> OTHER INFORMATION: /replace="Ser" or "Val" or "Leu"
<220> FEATURE:
<221> NAME/KEY: VARIANT
<222> LOCATION: (31)..(31)
<223> OTHER INFORMATION: /replace="Asn" or "His"
<220> FEATURE:
<221> NAME/KEY: VARIANT
<222> LOCATION: (32)..(32)
<223> OTHER INFORMATION: /replace="Asn" or "Ser"
<220> FEATURE:
<221> NAME/KEY: VARIANT
<222> LOCATION: (33)..(33)
<223> OTHER INFORMATION: /replace="Leu" or "Asn" or "Gly"
<220> FEATURE:
<221> NAME/KEY: VARIANT
<222> LOCATION: (34)..(34)
<223> OTHER INFORMATION: /replace="His" or "Gly" or "Tyr"
<220> FEATURE:
<221> NAME/KEY: VARIANT
<222> LOCATION: (35)..(35)
<223> OTHER INFORMATION: /replace="Thr"
<220> FEATURE:
<221> NAME/KEY: VARIANT
<222> LOCATION: (36)..(36)
<223> OTHER INFORMATION: /replace="Tyr"
<220> FEATURE:
<221> NAME/KEY: VARIANT
<222> LOCATION: (37)..(37)
<223> OTHER INFORMATION: /replace="Met"
<220> FEATURE:
<221> NAME/KEY: VARIANT
<222> LOCATION: (38)..(38)
<223> OTHER INFORMATION: /replace="His"
<220> FEATURE:
<221> NAME/KEY: misc_feature
<222> LOCATION: (27)..(38)
<223> OTHER INFORMATION: /note="Residues given in the sequence have no
      preference with respect to those in the annotations for said
      position"
<220> FEATURE:
<221> NAME/KEY: VARIANT
<222> LOCATION: (41)..(41)
<223> OTHER INFORMATION: /replace="Tyr"
<220> FEATURE:
<221> NAME/KEY: VARIANT
<222> LOCATION: (42)..(42)
<223> OTHER INFORMATION: /replace="Leu"
<220> FEATURE:
<221> NAME/KEY: misc_feature
<222> LOCATION: (41)..(42)
<223> OTHER INFORMATION: /note="Residues given in the sequence have no
      preference with respect to those in the annotations for said
      position"
<220> FEATURE:
<221> NAME/KEY: VARIANT
<222> LOCATION: (44)..(44)
<223> OTHER INFORMATION: /replace="Arg"
<220> FEATURE:
<221> NAME/KEY: misc_feature
<222> LOCATION: (44)..(44)
<223> OTHER INFORMATION: /note="Residue given in the sequence has no
      preference with respect to the annotation for said position"
<220> FEATURE:
<221> NAME/KEY: VARIANT
<222> LOCATION: (46)..(46)
<223> OTHER INFORMATION: /replace="Asp"
<220> FEATURE:
<221> NAME/KEY: VARIANT
<222> LOCATION: (47)..(47)
```

```
<223> OTHER INFORMATION: /replace="Lys"
<220> FEATURE:
<221> NAME/KEY: VARIANT
<222> LOCATION: (48)..(48)
<223> OTHER INFORMATION: /replace="Ser" or "Pro"
<220> FEATURE:
<221> NAME/KEY: misc_feature
<222> LOCATION: (46)..(48)
<223> OTHER INFORMATION: /note="Residues given in the sequence have no
      preference with respect to those in the annotations for said
      position"
<220> FEATURE:
<221> NAME/KEY: VARIANT
<222> LOCATION: (50)..(50)
<223> OTHER INFORMATION: /replace="Arg" or "Gln"
<220> FEATURE:
<221> NAME/KEY: VARIANT
<222> LOCATION: (51)..(51)
<223> OTHER INFORMATION: /replace="Arg"
<220> FEATURE:
<221> NAME/KEY: misc_feature
<222> LOCATION: (50)..(51)
<223> OTHER INFORMATION: /note="Residues given in the sequence have no
      preference with respect to those in the annotations for said
      position"
<220> FEATURE:
<221> NAME/KEY: VARIANT
<222> LOCATION: (54)..(54)
<223> OTHER INFORMATION: /replace="Lys"
<220> FEATURE:
<221> NAME/KEY: VARIANT
<222> LOCATION: (55)..(55)
<223> OTHER INFORMATION: /replace="Tyr" or "Lys" or "Ile"
<220> FEATURE:
<221> NAME/KEY: VARIANT
<222> LOCATION: (56)..(56)
<223> OTHER INFORMATION: /replace="Thr" or "Val"
<220> FEATURE:
<221> NAME/KEY: VARIANT
<222> LOCATION: (57)..(57)
<223> OTHER INFORMATION: /replace="Tyr"
<220> FEATURE:
<221> NAME/KEY: VARIANT
<222> LOCATION: (58)..(58)
<223> OTHER INFORMATION: /replace="Gln" or "Asn"
<220> FEATURE:
<221> NAME/KEY: VARIANT
<222> LOCATION: (59)..(59)
<223> OTHER INFORMATION: /replace="Ser" or "Leu"
<220> FEATURE:
<221> NAME/KEY: VARIANT
<222> LOCATION: (60)..(60)
<223> OTHER INFORMATION: /replace="Ile" or "Phe" or "Glu"
<220> FEATURE:
<221> NAME/KEY: VARIANT
<222> LOCATION: (61)..(61)
<223> OTHER INFORMATION: /replace="Ser"
<220> FEATURE:
<221> NAME/KEY: misc_feature
<222> LOCATION: (54)..(61)
<223> OTHER INFORMATION: /note="Residues given in the sequence have no
      preference with respect to those in the annotations for said
      position"
<220> FEATURE:
<221> NAME/KEY: VARIANT
<222> LOCATION: (63)..(63)
<223> OTHER INFORMATION: /replace="Ile"
<220> FEATURE:
<221> NAME/KEY: misc_feature
<222> LOCATION: (63)..(63)
<223> OTHER INFORMATION: /note="Residue given in the sequence has no
      preference with respect to the annotation for said position"
<220> FEATURE:
<221> NAME/KEY: VARIANT
<222> LOCATION: (65)..(65)
<223> OTHER INFORMATION: /replace="Ala" or "Asp"
<220> FEATURE:
<221> NAME/KEY: misc_feature
<222> LOCATION: (65)..(65)
<223> OTHER INFORMATION: /note="Residue given in the sequence has no
```

```
      preference with respect to those in the annotations for said
      position"
<220> FEATURE:
<221> NAME/KEY: VARIANT
<222> LOCATION: (75)..(75)
<223> OTHER INFORMATION: /replace="Glu"
<220> FEATURE:
<221> NAME/KEY: misc_feature
<222> LOCATION: (75)..(75)
<223> OTHER INFORMATION: /note="Residue given in the sequence has no
      preference with respect to the annotation for said position"
<220> FEATURE:
<221> NAME/KEY: VARIANT
<222> LOCATION: (79)..(79)
<223> OTHER INFORMATION: /replace="Thr"
<220> FEATURE:
<221> NAME/KEY: misc_feature
<222> LOCATION: (79)..(79)
<223> OTHER INFORMATION: /note="Residue given in the sequence has no
      preference with respect to the annotation for said position"
<220> FEATURE:
<221> NAME/KEY: VARIANT
<222> LOCATION: (81)..(81)
<223> OTHER INFORMATION: /replace="Asn"
<220> FEATURE:
<221> NAME/KEY: VARIANT
<222> LOCATION: (82)..(82)
<223> OTHER INFORMATION: /replace="Arg"
<220> FEATURE:
<221> NAME/KEY: VARIANT
<222> LOCATION: (83)..(83)
<223> OTHER INFORMATION: /replace="Leu"
<220> FEATURE:
<221> NAME/KEY: VARIANT
<222> LOCATION: (84)..(84)
<223> OTHER INFORMATION: /replace="Glu"
<220> FEATURE:
<221> NAME/KEY: VARIANT
<222> LOCATION: (85)..(85)
<223> OTHER INFORMATION: /replace="Ala" or "Ser"
<220> FEATURE:
<221> NAME/KEY: misc_feature
<222> LOCATION: (81)..(85)
<223> OTHER INFORMATION: /note="Residues given in the sequence have no
      preference with respect to those in the annotations for said
      position"
<220> FEATURE:
<221> NAME/KEY: VARIANT
<222> LOCATION: (88)..(88)
<223> OTHER INFORMATION: /replace="Ala" or "Val"
<220> FEATURE:
<221> NAME/KEY: VARIANT
<222> LOCATION: (89)..(89)
<223> OTHER INFORMATION: /replace="Gly"
<220> FEATURE:
<221> NAME/KEY: VARIANT
<222> LOCATION: (90)..(90)
<223> OTHER INFORMATION: /replace="Val"
<220> FEATURE:
<221> NAME/KEY: misc_feature
<222> LOCATION: (88)..(90)
<223> OTHER INFORMATION: /note="Residues given in the sequence have no
      preference with respect to those in the annotations for said
      position"
<220> FEATURE:
<221> NAME/KEY: VARIANT
<222> LOCATION: (94)..(94)
<223> OTHER INFORMATION: /replace="Ser"
<220> FEATURE:
<221> NAME/KEY: VARIANT
<222> LOCATION: (95)..(95)
<223> OTHER INFORMATION: /replace="His"
<220> FEATURE:
<221> NAME/KEY: VARIANT
<222> LOCATION: (96)..(96)
<223> OTHER INFORMATION: /replace="Tyr"
<220> FEATURE:
<221> NAME/KEY: VARIANT
<222> LOCATION: (97)..(97)
<223> OTHER INFORMATION: /replace="Asn" or "Thr" or "Arg"
```

```
<220> FEATURE:
<221> NAME/KEY: VARIANT
<222> LOCATION: (98)..(98)
<223> OTHER INFORMATION: /replace="Arg" or "His" or "Glu"
<220> FEATURE:
<221> NAME/KEY: VARIANT
<222> LOCATION: (99)..(99)
<223> OTHER INFORMATION: /replace="Trp" or "Val" or "Leu"
<220> FEATURE:
<221> NAME/KEY: misc_feature
<222> LOCATION: (94)..(99)
<223> OTHER INFORMATION: /note="Residues given in the sequence have no
      preference with respect to those in the annotations for said
      position"
<220> FEATURE:
<221> NAME/KEY: VARIANT
<222> LOCATION: (101)..(101)
<223> OTHER INFORMATION: /replace="Tyr"
<220> FEATURE:
<221> NAME/KEY: misc_feature
<222> LOCATION: (101)..(101)
<223> OTHER INFORMATION: /note="Residue given in the sequence has no
      preference with respect to the annotation for said position"
<220> FEATURE:
<221> NAME/KEY: VARIANT
<222> LOCATION: (108)..(108)
<223> OTHER INFORMATION: /replace="Lys"
<220> FEATURE:
<221> NAME/KEY: misc_feature
<222> LOCATION: (108)..(108)
<223> OTHER INFORMATION: /note="Residue given in the sequence has no
      preference with respect to the annotation for said position"

<400> SEQUENCE: 79

Asp Ile Val Met Thr Gln Ser Pro Ser Ser Leu Ala Val Ser Pro Gly
1               5                   10                  15

Glu Arg Ala Thr Ile Ser Cys Lys Ala Ser Gln Asp Val Gly Thr Ala
            20                  25                  30

Val Ala Asn Thr Tyr Phe His Trp Phe Gln Gln Lys Pro Gly Gln Ala
        35                  40                  45

Pro Lys Leu Leu Ile Tyr Trp Ala Ser Thr Arg His Thr Gly Val Pro
    50                  55                  60

Ser Arg Phe Ser Gly Ser Gly Ser Gly Thr Asp Phe Thr Leu Lys Ile
65                  70                  75                  80

Ser Ser Val Gln Pro Glu Asp Phe Ala Thr Tyr Tyr Cys Gln Gln Ser
                85                  90                  95

Ser Ser Tyr Pro Leu Thr Phe Gly Gln Gly Thr Arg Val Glu Ile Lys
            100                 105                 110

Arg

<210> SEQ ID NO 80
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 80

His His His His His His
1               5
```